(12) United States Patent
Weiner et al.

(10) Patent No.: US 6,335,178 B1
(45) Date of Patent: Jan. 1, 2002

(54) COMPOSITIONS AND METHODS FOR PROTEIN SECRETION

(75) Inventors: Joel Hirsch Weiner, Edmonton; Raymond Joseph Turner, Calgary, both of (CA)

(73) Assignee: University of Alberta, Alberta (CA)

( * ) Notice: Subject to any disclaimer, the term of this patent is extended or adjusted under 35 U.S.C. 154(b) by 0 days.

(21) Appl. No.: 09/085,761

(22) Filed: May 28, 1998

Related U.S. Application Data

(63) Continuation-in-part of application No. 09/053,197, filed on Apr. 1, 1998, now Pat. No. 6,022,952.

(51) Int. Cl.$^7$ .......................... C12P 21/06; C12N 1/20; C12N 15/63; C07K 14/00; C07H 21/04

(52) U.S. Cl. .................. 435/69.1; 435/69.7; 435/252.3; 435/320.1; 530/350; 530/300; 536/23.1; 536/23.4; 536/23.7

(58) Field of Search ............................. 435/69.1, 69.7, 435/252.3, 320.1; 536/23.1, 23.4, 23.7, 24.32, 6; 530/350, 329, 324, 300

(56) References Cited

U.S. PATENT DOCUMENTS

| | | | |
|---|---|---|---|
| 4,683,195 A | 7/1987 | Mullis | 435/6 |
| 4,683,202 A | 7/1987 | Mullis et al. | 435/91 |

OTHER PUBLICATIONS

Database GenBank on STN, Accession No. H65188. "yigU protein—*Escherichia coli* (strain K12)" Blattner et al. (1997).*
Database GenBank on STN, Accession No. P27857. "YigU_*E. coli*" Daniels et al. (1997).*
Database GenBank on STN, Accession No. A65189. "yigW protein—*Escherichia coli*" Blattner et al. (1997).*
Database GenBank on STN, Accession No. P27859. "YigW_*E. coli*" Daniels et al. (1997).*
Database GenBank on STn, Accession No. G65188. "hypothetical 15.6 kD protein in udp–rfaH intergenic region—*Escherichia coli* (strain K–12)" Blattner et al. (1997).*
Database GenBank on STN, Accession No. E65188. "hypothetical 11.3 kD protein in udp–rfaH intergenic region—*Escherichia coli* (strain K–12)" Blattner et al. (1997).*
Weiner et al. (Apr. 13, 1998) A Novel Ubiquitous System for Membrane Targeting and Secretion of Cofactor–Containing Proteins. Cell, vol. 93, pp. 93–101.*
Daniels et al. (1992) Analysis of the *Escherichia coli* Genome: DNA Sequence of the Region from 84.5 to 86.5 Minutes. Science, vol. 257, pp. 771–778.*
Blattner et al. (1997) The Complete Genome Sequence of *Escherichia coli* K–12. Science, vol. 277, pp. 1453–1462.*
George et al. (1988) "Current Methods in Sequence Comparison and Analysis" In, Macromolecular Sequencing and Synthesis, Selected Methods and Applications., D.H. Schlesinger (Ed.) Alan R. Liss, Inc. New York, NY. pp. 127–149.*
Barton (1996) "Protein Sequence Alignment and Database Scanning" In, Protein Structure Prediction, A Practical Approach. IRL Press at Oxford Univ. Press. Oxford, UK. pp. 31–63.*
Maniatis et al. (1982) Molecular Cloning A Laboratory Manual. Cold Spring Harbor Laboratory. pp. 403–409.*
Stryer et al. (1981) Biochemistry, 2nd Edition. W.H. Freeman and Co.*
Marston (1986) "The purification of eukaryotic polypeptides synthesized in *Escherichia coli*," Biochem. J. 240:1–12.
Schein (1989) "Production of Soluble Recombinant Proteins in Bacteria," Biotechnology 7:1141–1149.
Maniatis et al. (1987) "Regulation of Inducible and Tissue–Specific Gene Expression," Science 236:1237–1244.
Voss et al. (1986) "The role of enhancers in the regulation of cell–type–specific transcriptional control," Trends Biochem. Sci. 11:287–289.
Sambasivarao et al. (1991) "Dimethyl Sulfoxide Reductase of *Escherichia coli*: an Investigation of Function and Assembly by Use of In Vivo Complementation," J. Bacteriol. 5935–5943.
Jasin et al. (1984) "Deletion of an Essential Gene in *Escherichia coli* by Site–Specific Recombination with Linear DNA Fragments," J. Bacteriol. 159:783–786.
Bowe and Heffron (1994) "Isolation of Salmonella Mutants Defective for Intracellular Survival," Meth. in Enzymology 236:509–526.
Taylor et al. (1994) "Location of a Potassium Tellurite Resistance Operon (tehA tehB) within the Terminus of *Escherichia coli* K–12," J. Bacteriol. 176:2740–2742.
Barany (1991) "Genetic disease detection and DNA amplification using cloned thermostable ligase," Proc. Natl. Acad. Sci. 88:189–193.
Barany (1991) "The Ligase Chain Reaction in a PCR World," PCR Methods and Applic. 1:5–14.
Wu and Wallace (1989) "The Ligation Amplfiication Reaction (LAR)—Amplification of Specific DNA Sequences Using Sequential Rounds of Template–Dependent Ligation," Genomics 4:560–569.

(List continued on next page.)

*Primary Examiner*—Karen Cochrane Carlson
*Assistant Examiner*—Rita Mitra
(74) *Attorney, Agent, or Firm*—Medlen & Carroll, LLP

(57) ABSTRACT

The present invention relates to compositions and methods for secretion of functional proteins in a soluble form by host cells. In particular, the invention relates to membrane targeting and translocation proteins, MttA, MttB and MttC and to variants and homologs thereof. The membrane targeting and translocation proteins are useful in targeting protein expression to the periplasm of gram negative bacteria and to extracellular media of other host cells. Such expression allows secretion of expressed proteins of interest in a functional and soluble form, thus facilitating purification and increasing the yield of functional proteins of interest.

14 Claims, 32 Drawing Sheets

OTHER PUBLICATIONS

Latour and Weiner (1987) "Investigation of *Escherichia coli* Fumarate Reductase Subunit Function Using Transposon Tn5," J. Gen. Microbiol. 133:597–607.

Lemire et al. (1983) "Structure of Fumarate Reductase on the Cytoplasmic Membrane of *Escherichia coli*," J. Bacteriol. 155:391–397.

McEwan (1994) "Photosynthetic electron transport and anaerobic metabolism in purple non–sulfur phototrophic bacteria," Antonie van Leeuwenhoek 66:151–164.

McEwan et al. (1991) "Purification and properties of dimethyl sulphoxide reductase from *Rhodobacter capsulatus*," Biochem. J. 274:305–307.

Settles et al. (1997) "Sec–Independent Protein Translocation by the Maize Hcf106 Protein," Science 278:1467–1470.

Berks (1996) "A common export pathway for proteins binding complex redox cofactors?" Mol. Microbiol. 22:393–404.

von Heijne (1987) "SIGPEP: a sequence database for secretory signal peptides," Protein Seq. Data Anal. 1:41–42.

van der Palen et al. (1995) "Mutational analysis of mau genes involved in methylamine metabolism in *Paracoccus denitrificans*," Eur. J. Biochem. 230:860–871.

Richterich et al. (1993) "DNA Sequencing with Direct Transfer Electrophoresis and Nonradioactive Detection," Meth. in Enzymol. 218:187–222.

Hussain et al. (1994) "A seven–gene operon essential for formate–dependent nitrite reduction to ammonia by enteric bacteria," Mol. Microbiol. 12:153–163.

Rossi et al. (1993) "The hmc Operon of *Desulfovibrio vulgaris* subsp. *vulgaris* Hildenborough Encodes a Potential Transmembrane Redox Protein Complex," J. Bacteriol. 175:4699–471.

Kusano et al. (1992) "Molecular Cloning of the Gene Encoding *Thiobacillus ferrooxidans* Fe(II) Oxidase," J. Biol. Chem. 267:11242–11247.

Voordouw et al. (1989) "Organization of the Genes Encoding [Fe] Hydrogenase in *Desulfovibrio vulgaris* subsp. *oxamicus* Monticello," J. Bacteriol. 171:3881–3889.

Voordouw et al. (1989) "Analysis and Comparison of Nucleotide Sequences Encoding the Genes for [NiFe] and [NiFeSe] Hydrogenases from *Desulfovibrio gigas* and *Desulfovibrio baculatus*," J. Bacteriol. 171:2894–2899.

Menon et al. (1990) "Cloning and Sequencing of a Putative *Escherichia coli* [NiFe] Hydrogenase–1 Operon Containing Six Open Reading Frames," J. Bacteriol. 172:1969–1977.

Deppenmeier et al. (1995) "Different structure and expression of the operons encoding the membrane–bound hydrogenases from *Methanosarcina mazei* Göl," Arch. Microbiol. 164:370–376.

Deppenmeier et al (1995) "Analysis of the vhoGAC and vhtGAC operons from *Methanosarcina mazei* strain Go 1, both encoding a membrane–bound hydrogenase and a cytochrome b," Eur. J. Biochem. 227:261–269.

Li et al. (1987) "Cloning, Chracterization, and Sequencing of the Genes Encoding the Large and Small Subunits of the Periplasmic [NiFe] hydrogenase of *Desulfovibrio gigas*," DNA 6:539–551.

Menon et al. (1994) In Vivo and In Vitro Nickel–Dependent Processing of the [NiFe] Hydrogenase in *Azotobacter vinelandii*, J. Bacteriol. 176:291–295.

Kurowski and Ludwig (1987) "The Genes of the *Paracoccus denitrificans* $bc_1$ Complex," J. Biol. Chem. 262:13805–13811.

Mayes and Barber (1991) "Primary structure of the psb-N–psbH–petC–petA gene cluster of the cyanobacterium Synechocystis PCC 6803," Plant Molec. Biol. 17:289–293.

Castresana et al. (1995) "New Archaebacterial Genes Coding for Redox Proteins: Implications for the Evolution of Aerobic Metabolism," J. Mol. Biol. 250:202–210.

Hilton and Rajagopalan (1996) "Molecular cloning of dimethyl sulfoxide reductase from *Rhodobacter sphaeroides*," Biochim. Biophys. Acta 1294:111–114.

Campbell and Campbell (1996) "Alternative Gene for Biotin Sulfoxide Reduction in *Escherichia colia* K–12," J. Mol. Evol. 42:85–90.

Berks et al. (1995) "The napEDABC gene cluster encoding the periplasmic nitrate reductase system of *Thiosphaera pantotropha*," Biochem. J. 309:983–992.

Bokranz et al. (1991) "Cloning and nucleotide sequence of the structural genes encoding the formate dehydrogenase of *Wolinella succinogenes*," Arch. Microbiol. 156:119–128.

Bilous et al. (1988) "Nucleotide sequence of the dmsABC operon encoding the anaerobic dimethylsulphoxide reductase of *Escherichia coli*," Molec Microbiol. 2:785–795.

Fleischmann et al. (1995) "Whole–Genome Random Sequencing and Assembly of *Haemophilus influenzae* Rd," Science 269:496–512.

Heinzinger et al. (1995) "Sequence Analysis of the phs Operon in *Salmonella thypimurium* and the Contribution of Thiosulfate Reduction to Anaerobic Energy Metabolism" J. Bacteriol. 177:2813–2820.

Lehmann et al. (1995) "Molecular Cloning of the Isoquinoline 1–Oxidoreductase Genes from *Pseudomonas diminuta* 7, Structural Analysis of IorA and IorB, and Sequence Comparisons with Other Molybdenum–containing Hydroxylases," J. Biol. Chem. 270:14420–14429.

Tamaki et al. (1989) "Nucleotide Sequence of the Membrane–Bound Aldehyde Dehydrogenase Gene from *Acetobacter polyoxogenes*," J. Biochem. 106:5441–5444.

Viebrock and Zumft (1988) "Molecular Cloning, Heterologous Expression, and Primary Structure of the Structural Gene for the Copper Enzyme Nitrous Oxide Reductase from Denitrifying *Pseudomonas stutzeri*," J. Bacteriol. 170:4658–4668.

Mellano and Cooksey (1988) "Nucleotide Sequence and Organization of Copper Resistance Genes from *Pseudomonas syringae* pv. *tomato*," J. Bacteriol. 170:2879–2883.

Chistoserdov and Lidstrom (1991) "The Small–Subunit Polypeptide of Methylamine Dehydrogenase from *Methylobacterium extorquens* AM1 Has An Unusual Leader Sequence," J. Bacteriol. 173:5909–5913.

Dolata et al. (1993) "Nucleotide Sequence of the Heme Subunit of Flavocytochrome c from the Purple Phototrophic Bacterium, *Chromatium vinosum*," J. Biol. Chem. 268:14426–14431.

Ohta et al. (1991) "Sequence of gene choB encoding cholesterol oxidase of *Brevibacterium sterolicum*: comparison with choA of Streptomyces sp. SA–COO," Gene 103:93–96.

Keon and Voordouw (1996) "Identification of the HmcF and Topology of the HmcB Subunit of the Hmc Complex of *Desulfovibrio vulgaris*," Anaerobe 2:231–238.

Nivière et al. (1992) "Site–directed mutagenesis of the hydrogenase signal peptide consensus box prevents export of a β–lactamase fusion protein," J. Gen. Microbiol. 138:2173–2183.

Bishop et al. (1995) "Stationary Phase Expression of a Novel *Escherichia coli* Outer Membrane Lipoprotein and Its Relationship with Mammalian Apolipoprotein D," J. Biol. Chem. 270:23097–23103.

Rothery and Weiner (1996) "Interaction of an Engineered [3Fe–4S] Cluster with a Menaquinol Binding Site of *Escherichia coli* DMSO Reductase," Biochem. 35:3247–3257.

Rothery and Weiner (1993) "Topological Characterization of *Escherichia coli* DMSO Reductase by Electron Paramagnetic Resonance Spectroscopy of an Engineered [3Fe–4S] Cluster," Biochem. 32:5855–5861.

Sambasivarao et al. (1990) "Organization of Dimethyl Sulfoxide Reductase in the Plasma Membrane of *Escherichia coli*," J. Bacteriol. 172:5938–5948.

Weiner et al. (1992) "Molecular analysis of dimethylsulfoxide reductase: a complex iron–sulfur molybdoenzyme of *Escherichia coli*," Biochem. Biophys. Acta 1102:1–18.

Weiner et al. (1993) "The Topology of the Anchor Subunit of Dimethyl Sulfoxide Reductase of *Escherichia coli*," J. Biol. Chem. 268:3238–3244.

Rothery and Weiner (1991) "Alteration of the Iron–Sulfur Cluster Composition of *Escherichia coli* Dimethyl Sulfoxide Reductase by Site–Directed Mutagenesis," Biochem. 30:8296–8305.

Bilous and Weiner (1985) "Dimethyl Sulfoxide Reductase Activity by Anaerobically Grown *Escherichia coli* HB101," J. Bacteriol. 162:1151–1155.

Simala–Grant and Weiner (1996) "Kinetic analysis and substrate specificity of *Escherichia coli* dimethyl sulfoxide reductase," Microbiology 142:3231–3239.

Weiner and Heppel (1971) "A Binding Protein for Glutamine and Its Relation to Active Transport in *Escherichia coli*," J. Biol. Chem. 246:6933–6941.

Turner et al. (1997) "Expression and epitope tagging of the membrane anchor subunit (DmsC) of *Escherichia coli* dimethyl sulfoxide reductase," Protein Engineering 10:285–290.

Grove et al. (1996) "*Escherichia coli* K–12 genes essential for the synthesis of c–type cytochromes and a third nitrate reductase located in the periplasm," Mol. Microbiol. 19:467–481.

Cole (1996) "Nitrate reduction to ammonia by enteric bacteria: redundancy, or a strategy for survival during oxygen starvation?" FEMS Microbiol. Letts. 136:1–11.

McEwan et al. (1984) "Rationalization of properties of nitrate reductases in *Rhodopseudomonas capsulata*," Arch. Microbiol. 137:344–349.

Newman and Cole (1978) "The Chromosomal Location and Pleiotropic Effects of Mutations of the nirA[+] Gene of *Escherichia coli* K12: The Essential Role of nirA+ in Nitrite Reduction and in Other Anaerobic Redox Reactions," J. Gen. Microbiol. 106:1–12.

Thöny–Meyer and Kunzler (1997) "Translocation to the periplasm and signal sequence cleavage of preapocytochrome c depend on sec and lep, but not on the ccm gene products," Eur. J. Biochem. 246:794–799.

Darwin et al. (1993) "Identification of the formate dehydrogenases and genetic determinants of formate–dependent nitrite reduction by *Escherichia coli* K12," J. Gen. Microbiol. 139:1829–1840.

Méjean et al. (1994) "TMAO anaerobic respiration in *Escherichia coli*: involvement of the tor operon," Mol. Microbiol. 11:1169–1179.

Dickie and Weiner (1979) "Purification and characterization of membrane–bound fumarate reductase from anaerobically grown *Escherichia coli*," Can. J. Biochem. 57:813–821

Lemire and Weiner (1986) "Fumarate Reductase of *Escherichia coli*," Meth. Enzymol. 126:377–386.

Lemire et al. (1982) "Identification of Membrane Anchor Polypeptides of *Escherichia coli* Fumarate Reductase," J. Bacteriol. 152:1126–1131.

Berlyn et al. (1996) Edition 9 in *Escherichia coli and Salmonella* 2:1715–1902, ASM Press, Washington DC.

Blattner et al. (1997) "The Complete Genome Sequence of *Escherichia coli* K–12," Science 277:1453–1462.

Laemmli (1970) "Cleavage of Structural Proteins during the Assembly of the Head of Bacteriophage T4," Nature 227:680–685.

Cole et al. (1988) "Nucleotide Sequence and Gene–Polypeptide Relationships of the glpABC Operon Encoding the Anaerobic sn–Glycerol–3–Phosphate Dehydrogenase of *Escherichia coli* K–12," J. Bacteriol. 170:2448–2456.

Brown (1997) "Amyotrophic Lateral Sclerosis," Arch. Neurol. 54:1246–1250.

\* cited by examiner

FIG. 6A

```
                              α-helix
              160              170              180
MttA_ECOLI  L R S L A T T V Q N E L T Q E L K L Q E F Q D S L K K V E K
YIGT_HAEIN  I R G L A A N V Q N E L K Q E L K L Q E L Q D S I K K A E S α-helix
              190              200              210
MttA_ECOLI  A S L T N L T P E L K A S M D E L R Q A A E S M K R S Y V A
YIGT_HAEIN  N L N L Q A L S P E L S K T V E E L K A Q A D K M K A E L E D
            b→

220              230              240
MttA_ECOLI  N D P E K - - - A S D E A H T I H N P V V K D N E A A H E G
YIGT_HAEIN  K A A Q A G T T V E D Q I K E I K S A A E N A E K S Q N A I 250              260              270
MttA_ECOLI  V T P A A A Q T Q A S S P - - - - - - - - E Q K P E
YIGT_HAEIN  S V E E A A E T L S E A E R T P T D L T A L E T H E D V E L
                    TMS2

280              290              300
MttA_ECOLI  T T P E P V V K P A A D A E P K T A A P S P S S S D K P
YIGT_HAEIN  N T H L S S Y Y P P D D I E I A P A S K S Q S S K T K S
```

FIG. 6B

SEQUENCE RANGE: 5000 TO 9000

```
5000      5010      5020      5030      5040      5050
     TTCTGGGCTGGGTGCCACCAGATACCAACGTTGAAGAGTTCGAATTTGCCATTCGTACGGT 5060      5070      5080      5090      5100      5110
     CTGTGAACCTATCTTTGAGAAACCGCTGGCCCGAAATTTCGTTTGGACATGTACTGTTAAA 5120      5130      5140      5150      5160      5170
     TCTGTTTAATACGGCGCGTCGCTTCAATATGGAAGTGCAGCCGCAACTGGTGTTACTCCA 5180      5190      5200      5210      5220      5230
     GAAAACCCTGCTCTACGTCGAAGGGGTAGGACGCCAGCTTTATCCGCAACTCGATTTATG 5240      5250      5260      5270      5280      5290
     GAAAACGGCCAAGCCTTTCCTGGAGTCGTGGATTAAAGATCAGGTCGGTATTCCTCCGCT 5300      5310      5320      5330      5340      5350
     GCTGACAGCATTTAAAGAAAAAGCGCCGTTCTGGGTCCAAAAAATGCCAGAACTGCCTGA 5360      5370      5380      5390      5400      5410
     ATTGGTTTACGACAGTTTGCGCCAGGGCAAGTATTTACAGCACAGTGTTGATAAGATTGC 5420      5430      5440      5450      5460      5470
     CCGCCAGCTTCAGTCAAATCATGTACGTCAGGGACAATCCCGTTATTTTCTCGGAATTGG 5480      5490      5500      5510      5520      5530
     CGCTACGTTAGTATTAAGTGGCACATTCTTGTTGGTCAGCCGACCTGAATGGGGGCTGAT
```

FIG. 7A

```
5540         5550        5560         5570        5580        5590
GCCCGGCTGGTTAATGGCAGGTGGTCTGATCGCCTCCTTTGTCGGTTGGCGCAAAACACG 5600         5610        5620         5630        5640        5650
CTGATTTTTCATCGCTCAAGGCGGGCCGTGTAACGTATAATGCGGCTTTGTTAATCAT
                                                  M  R  L  C  L  I  I>
                                                  ORF RF(3)          >

5660         5670        5680         5690        5700        5710
CATCTACCACAGAGGAACATGTATGGGTGCTATCAGTATTGGCAGTTATTGATTATTGC
 I  Y  H  R  G  T  C  M  G  G  I  S  I  W  Q  L  L  I  I  A>
                ORF RF(3)                                    >

5720         5730        5740         5750        5760        5770
CGTCATCGTTGTTGTACTGCTTTTTGGCACCAAAAAGCTCGGCTCCATCGGTTCCGATCTTGG
 V  I  V  V  L  L  F  G  T  K  K  L  G  S  I  G  S  D  L  G>
                ORF RF(3)                                    >

5780         5790        5800         5810        5820        5830
TGCGTCGATCAAAGGCTTTAAAAAGCAAGCAATGAGCGATGATGAACCAAAGCAGGATAAAAC
 A  S  I  K  G  F  K  K  A  M  S  D  D  E  P  K  Q  D  K  T>
                ORF RF(3)                                    >

5840         5850        5860         5870        5880        5890
CAGTCAGGATGCTGATTTTACTGCGAAAACTATCGCCGATAAGCAGGCGGATACGAATCA
 S  Q  D  A  D  F  T  A  K  T  I  A  D  K  Q  A  D  T  N  Q>
                ORF RF(3)                                    >
```

FIG. 7B

```
5900         5910        5920        5930        5940        5950
GGAACAGGCTAAAACAGAAGAGCGGAAGCGCCACGATAAAGAGAGCAGGTGAATCCGTGTTT
  E  Q  A  K  T  E  D  A  K  R  H  D  K  E  Q  V  N  P  C  L>
                          ORF RF(3)                             >

5960         5970        5980        5990        6000        6010
GATATCGGTTTTAGCGAACTTGCTATTGGTGTTCATCATCGGCCTCGTCGTTCTGGGCC
  I  S  V  L  A  N  L  L  V  F  I  I  G  L  V  V  L  G  P>
                          ORF RF(3)                             >

6020         6030        6040        6050        6060        6070
GCAACGACTGCCTGTGGCGGTAAAAAACGGTAGCGGCTGGATTCGCGCGTTGCGTTCACT
  Q  R  L  P  V  A  V  K  T  V  A  G  W  I  R  A  L  R  S  L>
                          ORF RF(3)                             >

6080         6090        6100        6110        6120        6130
GGCGACAACGGTGCAGAACGAACTGACCCAGGAGTTAAAACTCCAGGAGTTTCAGGACAG
  A  T  T  V  Q  N  E  L  T  Q  E  L  K  L  Q  E  F  Q  D  S>
                          ORF RF(3)                             >

6140         6150        6160        6170        6180        6190
TCTGAAAAGGTTGAAAAGGCGAGCCTCACTAACCTGACGCCCGAACTGAAAGCGTCGAT
  L  K  K  V  E  K  A  S  L  T  N  L  T  P  E  L  K  A  S  M>
                          ORF RF(3)                             >

6200         6210        6220        6230        6240        6250
GGATGAACTACGCCAGGCCGCGAGTGCGATGAAGCGTTCCTACGTTGCAAACGATCCTGA
  D  E  L  R  Q  A  A  E  S  M  K  R  S  Y  V  A  N  D  P  E>
                          ORF RF(3)                             >
```

FIG. 7C

```
6260                 6270                 6280                 6290                 6300                 6310
     AAAGGCGAGGCGATGAAGCGCACACCATCCATAACCCGGTCCTGAAACATAATGAAGCTGC
      K  A  S  D  E  A  H  T  I  H  N  P  V  V  K  D  N  E  A  A >
                              ORF RF(3)

6320                 6330                 6340                 6350                 6360                 6370
     GCATGAGGGCGTAACGCCTGCCGCTGCACAAACGCAGGCCAGTTCGCCGGAACAGAAGCC
      H  E  G  V  T  P  A  A  A  Q  T  Q  A  S  S  P  E  Q  K  P >
                              ORF RF(3)

6380                 6390                 6400                 6410                 6420                 6430
     AGAAACCACGCCAGAGCCGGTGTAAAACCTGCTGCGGACGCTGAACCGAAAACCGCTGC
      E  T  T  P  E  P  V  V  K  P  A  A  D  A  E  P  K  T  A  A >
                              ORF RF(3)

6440                 6450                 6460                 6470                 6480                 6490
     ACCTTCCCCCTTCGTCGAGTGATAAACCGTAAACATGTCTGTAGAAGATACTCAACCGCTT
      P  S  S  S  S  D  K  P >               M  S  V  E  D  T  Q  P  L >
           ORF RF(3)                                ORF RF(2)

6500                 6510                 6520                 6530                 6540                 6550
     ATCACGCATCTGATTGAGCTGCGTAAGCGTCTGCTGAACTGCATTATCGCGGTGATCGTG
      I  T  H  L  I  E  L  R  K  R  L  L  N  C  I  I  A  V  I  V >
                              ORF RF(2)
```

FIG. 7D

```
6560      6570      6580      6590      6600      6610
ATATTCCTGTGTCTGGTCTCTATTTCGCCAATGACATCTATCACCTGGTATCCGCCATTG
  I   F   L   C   L   V   Y   F   A   N   D   I   Y   H   L   V   S   A   P   L>
                          ORF RF(2)

6620      6630      6640      6650      6660      6670
ATCAAGCAGTTGCCGCAAGGTTCAACGATGATCGCCACCGACGTGGCCTCGCCGTTCTTT
  I   K   Q   L   P   Q   G   S   T   M   I   A   T   D   V   A   S   P   F   F>
                          ORF RF(2)

6680      6690      6700      6710      6720      6730
ACGCCGATCAACCTCACCTTTATGGTGTCGCTGATTCTGTCAGCGCCGGTGATTCTCTAT
  T   P   I   K   L   T   F   M   V   S   L   I   L   S   A   P   V   I   L   Y>
                          ORF RF(2)

6740      6750      6760      6770      6780      6790
CAGGTGTCCCCATTTATCGCCCCAGCGCTGTATAAGCATGAACGTCGCCTGGTGGTGCCG
  Q   V   W   A   F   I   A   P   A   L   Y   K   H   E   R   R   L   V   V   P>
                          ORF RF(2)

6800      6810      6820      6830      6840      6850
CTGCTGGTTCCAGCTCTGCTCTGTTTTATATCGGCATGGCATTCGCCTACTTTGTGGTC
  L   L   V   S   S   L   L   F   Y   I   G   M   A   F   A   Y   F   V   V>
                          ORF RF(2)

6860      6870      6880      6890      6900      6910
TTTCCGCTGGCATTTGGCTTCCTTGCCAATACCGCCGGAAGGGGTGCAGGTATCCACC
  F   P   L   A   F   G   F   L   A   N   T   A   P   E   G   V   Q   V   S   T>
                          ORF RF(2)
```

FIG. 7E

```
6920      6930      6940      6950      6960      6970
GACATCGCCAGCTATTTAAGCTTCGTTATGGCGTTTATGGCCGTTTGGTGTCTCCTTT
 D   I   A   S   Y   L   S   F   V   M   A   L   F   M   A   F   G   V   S   F>
                                ORF RF(2)

6980      6990      7000      7010      7020      7030
GAAGTGCCGGTAGCAATTGTGCTGCTGTGCTGGATGGGAATTACCTCGCCAGAAGACTTA
 E   V   P   V   A   I   V   L   L   C   W   M   G   I   T   S   P   E   D   L>
                                ORF RF(2)

7040      7050      7060      7070      7080      7090
CGCAAAAAACGCCCCGTATGTGCTGGTTGGTGCATTCGTTGTCGGGATGTTGCTGACGCCG
 R   K   K   R   P   Y   V   L   V   G   A   F   V   V   G   M   L   L   T   P>
                                ORF RF(2)

7100      7110      7120      7130      7140      7150
CCGGATGTCTTCTCGCAAACGCTGTTGGCGCATCCCGATGTACTCGTGTCTGTTGAAATCGGT
 P   D   V   F   S   Q   T   L   L   A   I   P   M   Y   C   L   F   E   I   G>
                                ORF RF(2)

7160      7170      7180      7190      7200      7210
GTCTTCTTCTCCACGCTTTTACGTTGGTAAAGGGCGAAATCGGGAAGAGGAAAACGACGCT
 V   F   F   S   R   F   Y   V   G   K   G   R   N   R   E   E   N   D   A>
                                ORF RF(2)

7220      7230      7240      7250      7260      7270
GAAGCAGAAAGCGAAAAACTGAAGAATAAATTCAACCGCCCCGTCAGGGGCGGTTGTCATA
 E   A   E   S   E   K   T   E   E>
         ORF RF(2)
```

FIG. 7F

```
7280          7290         7300         7310         7320          7330
TGGAGTACAGGATGTTTGATATCGGCGTTAATTTGACCAGTTCGAATTTGCGAAAGACC
 M  E  Y  R  M  F  D  I  G  V  N  L  T  S  S  Q  F  A  K  D >
                      ORF RF(1)

7340          7350         7360         7370         7380          7390
GTGATGATGTTGTAGCGTGCCGCTTTGACGCGGGAGTTAATGGCTACTCATCACCGGCA
 R  D  D  V  V  A  C  A  F  D  A  G  V  N  G  L  L  I  T  G >
                      ORF RF(1)

7400          7410         7420         7430         7440          7450
CTAACCTGCGTGAAAGCCAGCAGCCCAAAAGCTGGCGCGTCAGTATTCGTCCTGTTGGT
 T  N  L  R  E  S  Q  Q  Q  A  Q  K  L  A  R  Q  Y  S  S  C  W >
                      ORF RF(1)

7460          7470         7480         7490         7500          7510
CAACGGGCGGGGCTACATCCTCACGACAGCCAGTGGCAAGCTGCGACTGAAGAAGCGA
 S  T  A  G  C  H  P  H  D  S  S  Q  W  Q  A  A  T  E  E  A >
                      ORF RF(1)

7520          7530         7540         7550         7560          7570
TTATTGAGCTGGCCGCGCAGCCAGAAGTGGCGGATTGGTGAATGTGTCTCGACTTTA
 I  I  E  L  A  A  Q  P  E  V  A  I  G  E  C  G  L  D  F >
                      ORF RF(1)

7580          7590         7600         7610         7620          7630
ACCGCAACTTTTCGACGCCGGAAGAGCAGGAAACGCGCTTTGTTGCCCAGCTACGCATTG
 N  R  N  F  S  T  P  E  E  Q  E  R  A  F  V  A  Q  L  R  I >
                      ORF RF(2)
```

FIG. 7G

```
7640                 7650                 7660                 7670                 7680                 7690
CCGCAGATTTAAACATGCCGGTATTTATGCACTGTCGCGATGCCCACGAGCGGGTTTATGA
 A  A  D  L  N  M  P  V  F  M  H  C  R  D  A  H  E  R  F  M>
                                  ORF RF(1)

7700                 7710                 7720                 7730                 7740                 7750
CATTGCTGGAGCCGTGGCTGGATAAACTGCCTGGTGCGGTTCTTCATTGCTTTACCGGCA
 T  L  L  E  P  W  L  D  K  L  P  G  A  V  L  H  C  F  T  G>
                                  ORF RF(1)

7760                 7770                 7780                 7790                 7800                 7810
CACGCGAAGAGATGCAGGCGTGCCGTGGCCATGGAATTTATATCGGCATTACCGGTTGGG
 T  R  E  E  M  Q  A  C  V  A  H  G  I  Y  I  G  I  T  G  W>
                                  ORF RF(1)

7820                 7830                 7840                 7850                 7860                 7870
TTTGCGATGAACGACGCGGACTGGGAGCTGCGGGAACTTTTGCCGTTGATTCCGGCGAAA
 V  C  D  E  R  R  G  L  E  L  R  E  L  L  P  L  I  P  A  E>
                                  ORF RF(1)

7880                 7890                 7900                 7910                 7920                 7930
AATTACTGATCGAAACTGATGCGCCGTATCTGCTCCCTCGCGATCTCACGCCAAAGCCAT
 K  L  I  E  T  D  A  P  Y  L  L  P  R  D  L  T  P  K  P>
                                  ORF RF(1)

7940                 7950                 7960                 7970                 7980                 7990
CATCCCGGCCAACGAGCCAGCCCATCTGCCCCATATTTTGCAACGTATTGCCCACTGGC
 S  S  R  R  N  E  P  A  H  L  P  H  I  L  Q  R  I  A  H  W>
                                  ORF RF(1)
```

FIG. 7H

```
8000        8010        8020        8030        8040        8050
GTGGAGAAGATGCCGCATGGCTGCTGGCTGCCACCACGGATGCTAATGTCAAAACACTGTTTG
 R   G   E   D   A   A   W   L   A   A   T   D   A   N   V   K   T   L   F >
                        ORF RF(1)

8060        8070        8080        8090        8100        8110
GGATTGCGTTTTAGAGTTTGCGGAACTCGGTATTCTTCACACTGTGCTTAATCTCTTTAT
 G   I   A   F >

8120        8130        8140        8150        8160        8170
TAATAAGATTAAGCAATAGCATGGAGCCTCACCATCGGGTTCGGTGAAAATGGCCT 8240        8250        8260        8270        8280        8290
GATCGACAATGTCTTTCGGTTTATATACCGATAGCTGATGAATAACCGCCGATGGGACTA 8300        8310        8320        8330        8340        8350
TCGCTGGCGACGCGCCAAAGCGCACGAAGTGGCTGACACCGCGGGTCGCGTTGATAGTCG 8360        8370        8380        8390        8400        8410
TGGTATGAATCACTTCTGGGTCAAATTCCACAAACAGTAGTTGGGAACAATGGCTCAC 8420        8430        8440        8450        8460        8470
TGACTGCAGTACGTTTTCCACGCACGATTTTTTCCAGGGTCATCATCGGTGCCAGGCAAT 8480        8490        8500        8510        8520        8530
TCACAGCCCTGTCTCTTTCGAGGTGTTCCTGGGCACGTTGAAGTTGCCCGCGCTTGCAGTACA
```

FIG. 71

```
8540        8550        8560        8570        8580        8590
GTAAATACCAGGATTGCATAATGACTCTTATCCGTTTAATCGGGGCGCAAGGATAGCAAA 8600        8610        8620        8630        8640        8650
AGCTTTACGCTAAGTTAATTATATTCCCCGGTTTCCGTTATACCGTCACAGTTCACCCTA 8660        8670        8680        8690        8700        8710
ATTTAACAAATTTACAGCATCGCAAAGATGAACGCCGTATAATGGGCGCAGATTAAGAGG 8720        8730        8740        8750        8760        8770
CTACAATGGACGCGCCATGAAATATAACCATTTACCCCCACTTCTTCACCCTCCTTGAACAGC 8780        8790        8800        8810        8820        8830
AGGGTGAGCTAAAACGTATCACGCTCCCGGTGATCCGCATCTGGAAATCACTGAAATTG 8840        8850        8860        8870        8880        8890
CTGACCGCACTTTGCGTGCCGGTGGGCCTGCGCTGTGTTCGAAAACCCTAAAGGCTACT 8900        8910        8920        8930        8940        8950
CAATGCCGGTGCTGTGCAACCTGTTCCCTACGCCAAAGCGCGTCCCCATGGGCATGGGGC 8960        8970        8980        8990        9000
AGGAAGATGTTTCGCCCGCTGCCGTGAAGTTGGTAAATTATTG
```

```
                         10                  20                  30
MttA
Hcf106_ZEAMA   M T F T A N L L L P A P P F V P I S D V R R L Q L P P R V R
YBEC_ECOLI                                              M A L T L V M
SYNEC
ORF13_RHOER
PSEST_ORF57
YY34_MYCLE
HELPY
HAEIN
BACSU
ORF4_AZOCH 40                  50                  60
MttA                                              M R L C L I I I
Hcf106_ZEAMA   H C P R P C W K C V E W C S I Q T R M V S S F V A V G S R T
YBEC_ECOLI
SYNEC          G A I A S P W V S V G T K L C Y S R L N E S F Y P S N P L T
ORF13_RHOER
PSEST_ORF57
YY34_MYCLE
HELPY
HAEIN
BACSU
ORF4_AZOCH                                    M A K K S I F R A K F F L F
```

|  | | | | | 130 | | | | | | | | 140 | | | | | 150 | | | |
|---|---|---|---|---|---|---|---|---|---|---|---|---|---|---|---|---|---|---|---|---|---|
| MttA | K | T | S | Q | D | – | A | – | D | F | T | A | K | T | I | A | D | K | Q | A | D | T | N | Q | E | Q | A | K |
| Hcf106_ZEAMA | E | F | R | S | T | L | E | – | I | D | G | V | S | K | H | Q | S | K | Y | R | P | T | M | N | N | Q |
| YBEC_ECOLI | K | K | G | A | D | – | V | R | E | – | D | L | Q | A | E | L | S | H | E | E | S | T | P | E | S | S | T | T | A |
| SYNEC | R | E | A | Q | N | L | E | – | I | – | K | S | V | Q | I | K | A | E | A | P | A | D | S | S | A | Q | R |
| ORF13_RHOER | T | P | A | P | T | A | Q | – | I | – | S | A | P | P | P | Q | S | L | P | A | E | L | P | V | A | D | T | T | A |
| PSEST_ORF57 | – | – | – | – | – | – | – | – | – | A | Q | A | S | A | L | E | – | G | E | T | N | P | T | V | S | Q | R |
| YY34_MYCLE | K | N | E | P | – | – | – | – | T | L | D | D | N | E | T | P | M | Q | N | P | T | Y | S | K | K | S | K |
| HELPY | K | D | A | E | F | – | K | – | S | I | D | N | E | T | A | K | V | H | E | S | E | K | R | E | N | R |
| HAEIN | – | – | – | – | – | – | – | – | I | – | – | – | – | – | L | T | D | E | K | K | G | K | K | E | D | Q |
| BACSU | – | – | – | – | – | – | – | – | – | – | – | – | – | – | – | – | – | – | – | – | – | – | – | – | – | – | – | – |
| ORF4_AZOCH | P | V | E | E | Q | – | K | – | G | Q | D | H | R | G | P | P | S | D | P | Q | G | R | G | T | G | Q | E | R | L | S |

|  | | | | 160 | | | | | 170 | | | | | 180 |
|---|---|---|---|---|---|---|---|---|---|---|---|---|---|---|---|
| MttA | T | E | D | A | K | R | H | D | K | E | Q | G | V | N | P | C | L | I | S | V | L | A | N | L | L | V | F | I | I |
| Hcf106_ZEAMA | Q | – | – | – | – | – | – | – | – | – | – | – | – | – | – | – | – | – | – | – | – | – | – | – | – | – | – | – | – |
| YBEC_ECOLI | – | – | – | – | – | – | – | – | – | – | – | – | – | – | – | – | – | – | – | – | – | – | – | – | – | – | – | – | – |
| SYNEC | P | – | – | – | – | – | – | – | – | – | – | – | – | – | – | – | – | – | – | – | – | – | – | – | – | – | – | – | – |
| ORF13_RHOER | – | – | – | – | – | – | – | – | – | – | – | – | – | – | – | – | – | – | – | – | – | – | – | – | – | – | – | – | – |
| PSEST_ORF57 | – | – | – | – | – | – | – | – | – | – | – | – | – | – | – | – | – | – | – | – | – | – | – | – | – | – | – | – | – |
| YY34_MYCLE | – | – | – | – | – | – | – | – | – | – | – | – | – | – | – | – | – | – | – | – | – | – | – | – | – | – | – | – | – |
| HELPY | – | – | – | – | – | – | – | – | – | – | – | – | – | – | – | – | – | – | – | – | – | – | – | – | – | – | – | – | – |
| HAEIN | – | – | – | – | – | – | – | – | – | – | – | – | – | – | – | – | – | – | – | – | – | – | – | – | – | – | – | – | – |
| BACSU | – | – | – | – | – | – | – | – | – | – | – | – | – | – | – | – | – | – | – | – | – | – | – | – | – | – | – | – | – |
| ORF4_AZOCH | M | D | F | I | G | – | – | – | – | – | F | S | E | L | L | V | G | L | V |

FIG. 8D

|  | | | 190 | | | | | | | | 200 | | | | | | | 210 | | | |
|---|---|---|---|---|---|---|---|---|---|---|---|---|---|---|---|---|---|---|---|---|---|
| MttA | G | L | V | V | L | G | P | Q | R | L | P | V | A | V | K | T | V | A | G | W | I | R | A | L | R | S | L | A | T | T | P |
| Hcf106_ZEAMA | - | - | - | - | - | - | - | - | - | - | - | - | - | - | - | - | - | P | A | A | D | P | N | V | K | P | E | R | A | P |
| YBEC_ECOLI | - | - | - | - | - | - | - | - | - | - | - | - | - | - | - | - | - | - | - | - | - | - | - | - | - | - | - | - | - | - |
| SYNEC | - | - | - | - | - | - | - | - | - | - | - | - | - | - | - | - | - | - | - | - | - | - | - | - | - | - | - | - | - | - |
| ORF13_RHOER | - | - | - | - | - | - | - | - | - | - | - | - | - | - | - | - | - | - | - | - | - | - | - | - | - | - | - | - | - | - |
| PSEST_ORF57 | - | - | - | - | - | - | - | - | - | - | - | - | - | - | - | - | - | - | - | - | - | - | - | - | - | - | - | - | - | - |
| YY34_MYCLE | - | - | - | - | - | - | - | - | - | - | - | - | - | - | - | - | - | - | - | - | - | - | - | - | - | - | - | - | - | - |
| HELPY | - | - | - | - | - | - | - | - | - | - | - | - | - | - | - | - | - | - | - | - | - | - | - | - | - | - | - | - | - | - |
| HAEIN | - | - | - | - | - | - | - | - | - | - | - | - | - | - | - | - | - | - | - | - | - | - | - | - | - | - | - | - | - | - |
| BACSU | - | - | - | - | - | - | - | - | - | - | - | - | - | - | - | - | - | - | - | - | - | - | - | - | - | - | - | - | - | - |

|  | | | | | | | | | 220 | | | | | | | 230 | | | | | | | 240 | |
|---|---|---|---|---|---|---|---|---|---|---|---|---|---|---|---|---|---|---|---|---|---|---|---|---|
| MttA | A | L | L | V | L | G | P | E | R | L | P | V | A | A | R | M | A | G | L | W | I | G | R | L | K | R | S | F | N | T |
| Hcf106_ZEAMA | V | Q | N | E | L | T | Q | E | L | K | L | Q | E | F | Q | D | S | L | K | K | V | E | K | A | S | L | T | N | L | T |
| YBEC_ECOLI | Y | T | S | E | E | L | M | K | V | T | E | E | Q | I | A | A | S | A | A | A | A | W | N | P | Q | Q | R | A | T | S |
| SYNEC | - | - | S | E | K | A | S | - | - | - | - | - | - | - | - | - | - | - | - | - | - | - | - | - | - | - | - | - | - | - |
| ORF13_RHOER | Q | P | Q | S | Q | H | T | E | P | K | S | A | - | - | - | - | - | - | - | - | - | - | - | - | - | - | - | - | - | - |
| PSEST_ORF57 | - | - | E | Q | D | H | T | E | A | R | P | A | - | - | - | - | - | - | - | - | - | - | - | - | - | - | - | - | - | - |
| YY34_MYCLE | - | - | Q | E | S | - | - | - | - | - | - | - | - | - | - | - | - | - | - | - | - | - | - | - | - | - | - | - | - | - |
| HELPY | V | F | Q | N | L | F | Y | - | - | - | - | - | - | - | - | - | - | - | - | - | - | - | - | - | - | - | - | - | - | - |
| HAEIN | - | - | - | - | - | - | - | - | - | - | - | - | - | - | - | - | - | - | - | - | - | - | - | - | - | - | - | - | - | - |
| BACSU | - | - | - | - | - | - | - | - | - | - | - | - | - | - | - | - | - | - | - | - | - | - | - | - | - | - | - | - | - | - |
| ORF4_AZOCH | L | K | T | E | V | E | R | E | I | G | A | D | E | I | R | R | - | - | - | Q | L | H | N | E | R | I | L | B | L | E |

```
                           250               260                270
MttA
Hcf106_ZEAMA    P E L K A S M D E L R Q A A A E S M K R S Y V A N D P E K A S
YBEC_ECOLI      Q Q Q E E A P T T F R - S E D A P T S G G S S G P A A P A R
SYNEC
ORF13_RHOER
PSEST_ORF57
YY34_MYCLE
HELPY
HAEIN
BACSU
ORF4_AZOCH 280               290                300
MttA            R E M K Q S L Q P P A P S A P D E T A A S P A T P P Q P P A S
Hcf106_ZEAMA    D E A H T I H N P V V K D N E A A H E G V T P A A A Q T Q A
YBEC_ECOLI      A E S D S D P N Q V N K S Q K A E G E R
SYNEC
ORF13_RHOER
PSEST_ORF57
YY34_MYCLE
HELPY
HAEIN
BACSU
ORF4_AZOCH      P A A H S D K T P S P
```

FIG. 8E

```
                              310              320              330
MttA            S S P E Q K P E T T P E P V V K P A A D A S P K T A A P S P
Hcf106_ZEAMA
YBEC_ECOLI
SYNEC
ORF13_RHOER
PSEST_ORF57
YY34_MYCLE
HELPY
HAEIN
BACSU
ORF4_AZOCH 340              350              360
MttA            S S S D K P
Hcf106_ZEAMA
YBEC_ECOLI
SYNEC
ORF13_RHOER
PSEST_ORF57
YY34_MYCLE
HELPY
HAEIN
BACSU
ORF4_AZOCH
```

| | | | | | | | | | | | | | | | | | | | | | |
|---|---|---|---|---|---|---|---|---|---|---|---|---|---|---|---|---|---|---|---|---|---|
| MttC | E | R | R | - | G | L | E | L | R | E | L | L | P | L | I | P | A | E | K | L | L | I | E | T | D | A | P | Y | L | L | P | 213 |
| YCFH_ECOLI | R | N | - | - | A | E | Q | L | R | D | D | A | A | R | Y | L | V | P | L | D | R | L | L | V | E | T | D | S | P | A | P | 209 |
| YJJV_ECOLI | P | R | - | - | A | S | K | T | H | L | R | D | V | I | A | K | A | H | P | L | A | S | L | L | E | T | D | A | P | M | L | 213 |
| METTH | S | - | I | - | - | E | H | H | M | E | L | V | R | S | V | L | M | P | L | E | G | M | L | V | E | T | D | S | P | Y | L | S | 212 |
| Y009_MYCPN | K | N | - | - | A | K | N | L | Q | A | A | L | S | V | P | L | H | P | L | E | T | L | L | V | E | T | D | A | P | Y | L | A | 217 |
| YcfH_Myctu | R | T | - | - | A | R | R | E | L | R | E | A | V | P | L | R | Y | L | M | P | V | L | L | V | E | T | D | S | P | Y | L | T | 214 |
| HELPY | K | N | - | - | A | K | R | L | V | E | I | H | V | L | P | K | Y | V | P | M | E | R | L | L | I | H | T | D | C | P | F | L | 208 |
| YCFH_HAEIN | K | N | - | - | A | K | E | A | R | K | E | V | V | K | E | R | Y | V | P | M | H | K | K | E | T | D | S | P | Y | L | S | 212 |
| YABD_BACSU | K | N | - | - | A | K | K | P | K | E | E | V | V | K | E | A | U | O | K | E | J | N | K | L | L | E | T | D | P | F | L | T | 209 |
| SCHPO | - | - | - | - | - | E | E | T | Q | L | L | H | E | S | I | P | H | P | L | S | Q | L | L | I | H | T | D | C | E | V | - | - | 187 |
| CAEEL | S | - | - | - | - | E | E | T | E | E | E | T | T | Q | L | L | H | E | S | I | P | H | P | L | S | Q | L | L | I | H | T | D | S | P | A | L | G | 330 |
| Y218_HUMAN | S | S | - | - | A | W | E | A | R | E | A | L | R | Q | I | P | L | E | R | I | V | E | T | D | A | P | Y | F | L | P | 713 |

FIG. 10B

```
            10         20         30         40         50         60
     ATTCTGGCTGGGTGCCACCAGATACCAACGTTGAAGAGTTCGAATTTGCCATTCGTACGG 70         80         90        100        110        120
     TCTGTGAACCTATCTTTGAGAAACCGCTGGCCGAAATTTCGTTTGGACATGTACTGTTAA 130        140        150        160        170        180
     ATCTGTTTAATACGGCGCGTCCCTTCAATATGGAAGTGCAGCCGCAACTGGTGTTACTCC 190        200        210        220        230        240
     AGAAAACCCTGCTCTACGTCGAAGGGGTAGGACGCCAGCTTTATCCGCAACTCGATTTAT 250        260        270        280        290        300
     GGAAAACGGCGAAGCCTTTCCTGGAGTCGTGGATTAAAGATCAGGTCGGTATTCCTGCGC 310        320        330        340        350        360
     TGGTGAGAGCATTTAAAGAAAAGCGCCGTTCTGGGTCGAAAAAATGCCAGAACTGCCTG 370        380        390        400        410        420
     AATTGGTTTACGACAGTTTGCGCCAGGGCAAGTATTTACAGCACAGTGTTGATAAGATTG 430        440        450        460        470        480
     CCCGCGAGCTTCAGTCAAATCATGTACGTCAGGGACAATCGCGTTATTTTCTCGGAATTG 490        500        510        520        530        540
     GCGCTACGTTAGTATTAAGTGGCACATTCTTGTTGGTCAGCCGACCTGAATGGGGCTGA 550        560        570        580        590        600
     TGCCCGGCTGGTTAATGGCAGGTGGTCTGATCGCCTGGTTTGTCGGTTGGCGCAAAACAC 610        620        630        640        650        660
     GCTGATTTTTTCATCGCTCAAGGCGGGCCGTGTAACGTATAATGCGGCTTTGTTTAATCA
                                              M   R   L   C   L   I>
                                             _____
                                                                  >

670        680        690        700        710        720
     TCATCTACCACAGAGGAACATGTATGGGTGGTATCAGTATTTGGCAGTTATTGATTATTG
      I   I   Y   M   R   G   T   C   M   C   C   I   S   I   W   Q   L   I   I   I>
     _____
                                                                                    >

730        740        750        760        770        780
     CCGTCATCGTTGTACTGCTTTTTGGCACCAAAAAGCTCGGCTCCATCGGTTCCGATCTTG
      A   V   I   V   V   L   L   F   G   T   K   K   L   G   S   I   G   S   D   L>
     _____
                                                                                    >

790        800        810        820        830        840
     GTGCGTCGATCAAAGGCTTTAAAAAAGCAATGAGCGATGATGAACCAAAGCAGGATAAAA
      G   A   S   I   K   G   F   K   K   A   M   S   D   D   E   P   K   Q   D   K>
     _____
                                                                                    >

850        860        870        880        890        900
     CCAGTCAGGATGCTGATTTTACTGCGAAAACTATCGCCGATAAGCAGGCGGATACGAATC
      T   S   Q   D   A   D   F   T   A   K   T   I   A   D   K   Q   A   D   T   N>
     _____
                                                                                    >
```

FIG. 11(A)

```
           910       920       930       940       950       960
     AGGAACAGGCTAAAACAGAAGACGCGAAGCGCCACGATAAAGAGCAGGTGTAATCCGTGT
      Q  E  Q  A  K  T  E  D  A  K  R  H  D  K  E  Q  V>       V>
                                                         ———
     ————————————————————————————————————————————————————     ——>
           970       980       990      1000      1010      1020
     TTGATATCGGTTTTAGCGAACTGCTATTGGTGTTCATCATCGGCCTCGTCGTTCTGGGGC
      F  D  I  G  F  S  E  L  L  L  V  F  I  I  G  L  V  V  L  G>
     ——————————————————————————————————————————————————————————>
          1030      1040      1050      1060      1070      1080
     CGCAACGACTGCCTGTGGCGGTAAAAACGCTAGCGGGCTGGATTCGCGCGTTGCGTTCAC
      P  Q  R  L  P  V  A  V  K  T  V  A  G  W  I  R  A  L  R  S
     ——————————————————————————————————————————————————————————>
          1090      1100      1110      1120      1130      1140
     TGGCGACAACGGTGCAGAACGAACTGACCCAGGAGTTAAAACTCCAGGAGTTTCAGGACA
      L  A  T  T  V  Q  N  E  L  T  Q  E  L  K  L  Q  E  F  Q  D>
     ——————————————————————————————————————————————————————————>
          1150      1160      1170      1180      1190      1200
     GTCTGAAAAAGGTTGAAAAGGCGAGCCTCACTAACCTGACGCCCGAACTGAAAGCGTCGA
      S  L  K  K  V  E  K  A  S  L  T  N  L  T  P  E  L  K  A  S>
     ——————————————————————————————————————————————————————————>
          1210      1220      1230      1240      1250      1260
     TGGATGAACTACGCCAGGCCGCGGAGTCGATGAAGCGTTCCTACGTTGCAAACGATCCTG
      M  D  E  L  R  Q  A  A  E  S  M  K  R  S  Y  V  A  N  D  P>
     ——————————————————————————————————————————————————————————>
          1270      1280      1290      1300      1310      1320
     AAAAGGCGAGCGATGAAGCGCACACCATCCATAACCCGGTGGTGAAAGATAATGAAGCTG
      E  K  A  S  D  E  A  H  T  I  H  N  P  V  V  K  D  N  E  A>
     ——————————————————————————————————————————————————————————>
          1330      1340      1350      1360      1370      1380
     CGCATGAGGGCGTAACGCCTGCCGCTGCACAAACGCAGGCCAGTTCGCCGGAACAGAAGC
      A  H  E  G  V  T  P  A  A  A  Q  T  Q  A  S  S  P  E  Q  K>
     ——————————————————————————————————————————————————————————>
          1390      1400      1410      1420      1430      1440
     CAGAAACCACGCCAGAGCCGGTGGTAAAACCTGCTGCGGACGCTGAACCGAAAACCGCTG
      P  E  T  T  P  E  P  V  V  K  P  A  A  D  A  E  P  K  T  A>
     ——————————————————————————————————————————————————————————>
          1450      1460      1470      1480      1490      1500
     CACCTTCCCCTTCGTCGAGTGATAAACCGTAAACATGTCTGTAGAAGATACTCAACCGCT
                                        M  S  V  E  D  T  Q  P  L>
                                        —————————————————————————>
      A  P  S  P  S  S  S  D  K  P>
     ——————————————————————>
          1510      1520      1530      1540      1550      1560
     TATCACGCATCTGATTGAGCTGCGTAAGCGTCTGCTGAACTGCATTATCGCGGTGATCGT
        I  T  H  L  I  E  L  R  K  R  L  L  N  C  I  I  A  V  I  V>
     ——————————————————————————————————————————————————————————>
```

FIG. 11(B)

```
      1570        1580        1590        1600        1610        1620
GATATTCCTGTGTCTGGTCTATTTCGCCAATGACATCTATCACCTGGTATCCGCGCCATT
  I   F   L   C   L   V   T   F   A   N   D   I   Y   H   L   V   S   A   P   L>
                                                                              >

1630        1640        1650        1660        1670        1680
GATCAAGCAGTTGCCGCAAGGTTCAACGATGATCGCCACCGACGTGGCCTCGCCGTTCTT
  I   K   Q   L   P   Q   G   S   T   M   I   A   T   D   V   A   S   P   F   F>
                                                                              >

1690        1700        1710        1720        1730        1740
TACGCCGATCAAGCTGACCTTTATGGTGTCGCTGATTCTGTCAGCGCCGGTGATTCTCTA
  T   P   I   K   L   T   F   M   V   S   L   I   L   S   A   P   V   I   L   Y>
                                                                              >

1750        1760        1770        1780        1790        1800
TCAGGTGTGGGCATTTATCGCCCCAGCGCTGTATAAGCATGAACGTCGCCTGGTGGTGCC
  Q   V   W   A   F   I   A   P   A   L   Y   K   H   E   R   R   L   V   V   P>
                                                                              >

1810        1820        1830        1840        1850        1860
GCTGCTGGTTTCCAGCTCTCTGCTGTTTTATATCGGCATGGCATTCGCCTACTTTGTGGT
  L   L   V   S   S   S   L   L   P   Y   J   C   M   A   F   A   Y   F   V   V>
                                                                              >

1870        1880        1890        1900        1910        1920
CTTTCCGCTGGCATTTGGCTTCCTTGCCAATACCGCGCCGGAAGGGGTGCAGGTATCCAC
  F   P   L   A   F   G   F   L   A   N   T   A   P   E   G   V   Q   V   S   T>
                                                                              >

1930        1940        1950        1960        1970        1980
CGACATCGCCAGCTATTTAAGCTTCGTTATGGCGCTGTTTATGGCGTTTGGTGTCTCCTT
  D   I   A   S   Y   L   S   F   V   M   A   L   F   M   A   F   G   V   S   F>
                                                                              >

1990        2000        2010        2020        2030        2040
TGAAGTGCCGGTAGCAATTGTGCTGCTGTGCTGGATGGGGATTACCTCGCCAGAAGACTT
  E   V   P   V   A   I   V   L   L   C   W   M   G   I   T   S   P   E   D   L>
                                                                              >

2050        2060        2070        2080        2090        2100
ACGCAAAAAACGCCCGTATGTGCTGGTTGGTGCATTCGTTGTCGGGATGTTGCTGACGCC
  R   K   K   R   P   Y   V   L   V   G   A   F   V   V   G   M   L   L   T   P>
                                                                              >

2110        2120        2130        2140        2150        2160
GCCGGATGTCTTCTCGCAAACGCTGTTGGCGATCCCGATGTACTGTCTGTTTGAAATCGG
  P   D   V   F   S   Q   T   L   L   A   I   P   M   Y   C   L   F   E   I   G>
                                                                              >

2170        2180        2190        2200        2210        2220
TGTCTTCTTCTCACGCTTTTACGTTGGTAAAGGGCGAAATCGGGAAGAGGAAAACGACGC
  V   F   F   S   R   F   Y   V   G   K   C   R   N   R   E   E   E   N   D   A>
                                                                              >
```

FIG. 11(C)

```
      2230      2240      2250      2260      2270      2280
TGAAGCAGAAAGCGAAAAAACTGAAGAATAAATTCAACCGCCCGTCAGGGCGGTTGTCAT
   E  A  E  S  E  K  T  E  E>
━━━━━━━━━━━━━━━━━━━━━━━━━━━━>

2290      2300      2310      2320      2330      2340
ATGGAGTACAGGATGTTTGATATCGGCGTTAATTTGACCAGTTCGCAATTTGCGAAAGAC
 M  E  Y  R  M  F  D  I  G  V  N  L  T  S  S  Q  P  A  K  D>
━━━━━━━━━━━━━━━━━━━━━━━━━━━━>

2350      2360      2370      2380      2390      2400
CGTGATGATGTTGTAGCGTGCGCTTTTGACGCGGGAGTTAATGGGCTACTCATCACCGGC
 R  D  D  V  V  A  C  A  P  D  A  C  V  N  G  L  L  I  T  G>
━━━━━━━━━━━━━━━━━━━━━━━━━━━━>

2410      2420      2430      2440      2450      2460
ACTAACCTGCGTGAAAGCCAGCAGGCGCAAAAGCTGGCGCGTCAGTATTCGTCCTGTTGG
 T  N  L  R  E  S  Q  Q  A  Q  K  L  A  R  Q  Y  S  S  C  W>
━━━━━━━━━━━━━━━━━━━━━━━━━━━━>

2470      2480      2490      2500      2510      2520
TCAACGGCGGGCGTACATCCTCACGACAGCAGCCAGTGGCAAGCTGCGACTGAAGAAGCG
 S  T  A  G  V  H  P  H  D  S  S  Q  W  Q  A  A  T  E  E  A>
━━━━━━━━━━━━━━━━━━━━━━━━━━━━>

2530      2540      2550      2560      2570      2580
ATTATTGAGCTGGCCGCGCAGCCAGAAGTGGTGGCGATTGGTGAATGTGGTCTCGACTTT
 I  I  E  L  A  A  Q  P  E  V  V  A  I  G  E  C  G  L  D  F>
━━━━━━━━━━━━━━━━━━━━━━━━━━━━>

2590      2600      2610      2620      2630      2640
AACCGCAACTTTTCGACGCCGGAAGAGCAGGAACGCGCTTTTGTTGCCCAGCTACGCATT
 N  R  N  F  S  T  P  E  E  Q  E  R  A  F  V  A  Q  L  R  I>
━━━━━━━━━━━━━━━━━━━━━━━━━━━━>

2650      2660      2670      2680      2690      2700
GCCGCAGATTTAAACATGCCGGTATTTATGCACTGTCGCGATGCCCACGAGCGGTTTATG
 A  A  D  L  N  M  P  V  F  M  H  C  R  D  A  H  E  R  F  M>
━━━━━━━━━━━━━━━━━━━━━━━━━━━━>

2710      2720      2730      2740      2750      2760
ACATTGCTGGAGCCGTGGCTGGATAAACTGCCTGGTGCGGTTCTTCATTGCTTTACCGGC
 T  L  L  E  P  W  L  D  K  L  P  G  A  V  L  H  C  F  T  G>
━━━━━━━━━━━━━━━━━━━━━━━━━━━━>

2770      2780      2790      2800      2810      2820
ACACGCGAAGAGATGCAGGCGTGCGTGGCGCATGGAATTTATATCGGCATTACCGGTTGG
 T  R  E  E  M  Q  A  C  V  A  H  G  I  T  I  G  I  T  G  W>
━━━━━━━━━━━━━━━━━━━━━━━━━━━━>

2830      2840      2850      2860      2870      2880
GTTTGCGATGAACGACGCGGACTGGAGCTGCGGGAACTTTTGCCGTTGATTCCGGCGGAA
 V  C  D  E  R  R  G  L  E  L  R  E  L  L  P  L  I  P  A  E>
━━━━━━━━━━━━━━━━━━━━━━━━━━━━>
```

FIG. 11(D)

```
          2890        2900        2910        2920        2930        2940
AAATTACTGATCGAAACTGATGCGCCGTATCTGCTCCCTCGCGATCTCACGCCAAAGCCA
  K   L   L   I   E   T   D   A   P   T   L   L   P   R   D   L   T   P   K   P>
                                                                              ────────>

2950        2960        2970        2980        2990        3000
TCATCCCGGCGCAACGAGCCAGCCCATCTGCCCCATATTTTGCAACGTATTGCGCACTGG
  S   S   R   R   N   E   P   A   H   L   P   H   I   L   Q   R   I   A   M   W>
                                                                              ────────>

3010        3020        3030        3040        3050        3060
CGTGGAGAAGATGCCGCATGGCTGGCTGCCACCACGGATGCTAATGCCAAAACACTGTTT
  R   G   E   D   A   A   W   L   A   A   T   T   D   A   N   A   K   T   L   F>
                                                                              ────────>

3070        3080        3090        3100        3110        3120
GGGATTGCGTTTTAGAGTTTGCGGAACTCGGTATTCTTCACACTGTGCTTAATCTCTTTA
  G   I   A   F>
  ────────>
```

FIG. 11(E)

SEQUENCE LISTING (1) GENERAL INFORMATION:

(iii) NUMBER OF SEQUENCES: 77

(2) INFORMATION FOR SEQ ID NO:1:

(i) SEQUENCE CHARACTERISTICS:
      (A) LENGTH: 277 amino acids
      (B) TYPE: amino acid
      (C) STRANDEDNESS: Not Relevant
      (D) TOPOLOGY: unknown (ii) MOLECULE TYPE: protein (xi) SEQUENCE DESCRIPTION: SEQ ID NO:1:

```
Met Arg Leu Cys Leu Ile Ile Ile Tyr His Arg Gly Thr Cys Met Gly
 1               5                  10                  15

Gly Ile Ser Ile Trp Gln Leu Leu Ile Ile Ala Val Ile Val Val Leu
            20                  25                  30

Leu Phe Gly Thr Lys Lys Leu Gly Ser Ile Gly Ser Asp Leu Gly Ala
        35                  40                  45

Ser Ile Lys Gly Phe Lys Lys Ala Met Ser Asp Asp Glu Pro Lys Gln
    50                  55                  60

Asp Lys Thr Ser Gln Asp Ala Asp Phe Thr Ala Lys Thr Ile Ala Asp
65                  70                  75                  80

Lys Gln Ala Asp Thr Asn Gln Glu Gln Ala Lys Thr Glu Asp Ala Lys
                85                  90                  95

Arg His Asp Lys Glu Gln Gly Val Asn Pro Cys Leu Ile Ser Val Leu
                100                 105                 110

Ala Asn Leu Leu Leu Val Phe Ile Ile Gly Leu Val Val Leu Gly Pro
            115                 120                 125

Gln Arg Leu Pro Val Ala Val Lys Thr Val Ala Gly Trp Ile Arg Ala
        130                 135                 140

Leu Arg Ser Leu Ala Thr Thr Val Gln Asn Glu Leu Thr Gln Glu Leu
145                 150                 155                 160

Lys Leu Gln Glu Phe Gln Asp Ser Leu Lys Lys Val Glu Lys Ala Ser
                165                 170                 175
```

```
Leu Thr Asn Leu Thr Pro Glu Leu Lys Ala Ser Met Asp Glu Leu Arg
            180                 185                 190

Gln Ala Ala Glu Ser Met Lys Arg Ser Tyr Val Ala Asn Asp Pro Glu
        195                 200                 205

Lys Ala Ser Asp Glu Ala His Thr Ile His Asn Pro Val Val Lys Asp
        210                 215                 220

Asn Glu Ala Ala His Glu Gly Val Thr Pro Ala Ala Gln Thr Gln
225                 230                 235                 240

Ala Ser Ser Pro Glu Gln Lys Pro Glu Thr Thr Pro Glu Pro Val Val
            245                 250                 255

Lys Pro Ala Ala Asp Ala Glu Pro Lys Thr Ala Ala Pro Ser Pro Ser
            260                 265                 270

Ser Ser Asp Lys Pro
            275

(2) INFORMATION FOR SEQ ID NO:2:

(i) SEQUENCE CHARACTERISTICS:
        (A) LENGTH: 284 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:2:

Met Ala Lys Lys Ser Ile Phe Arg Ala Lys Phe Phe Leu Phe Tyr Arg
1               5                   10                  15

Thr Glu Phe Ile Met Phe Gly Leu Ser Pro Ala Gln Leu Ile Ile Leu
            20                  25                  30

Leu Val Val Ile Leu Leu Ile Phe Gly Thr Lys Lys Leu Arg Asn Ala
            35                  40                  45

Gly Ser Asp Leu Gly Ala Ala Val Lys Gly Phe Lys Lys Ala Met Lys
        50                  55                  60

Glu Asp Glu Lys Val Lys Asp Ala Glu Phe Lys Ser Ile Asp Asn Glu
65                  70                  75                  80

Thr Ala Ser Ala Lys Lys Gly Lys Tyr Lys Arg Glu Arg Asn Arg Leu
            85                  90                  95

Asn Pro Cys Leu Ile Leu Val Phe Gln Asn Leu Phe Tyr Xaa Met Val
            100                 105                 110

Leu Gly Leu Val Val Leu Gly Pro Lys Arg Leu Pro Ile Ala Ile Arg
            115                 120                 125

Thr Val Met Asp Trp Val Lys Thr Ile Arg Gly Leu Ala Ala Asn Val
130                 135                 140

Gln Asn Glu Leu Lys Gln Glu Leu Lys Leu Gln Glu Leu Gln Asp Ser
145                 150                 155                 160

Ile Lys Lys Ala Glu Ser Leu Asn Leu Gln Ala Leu Ser Pro Glu Leu
            165                 170                 175

Ser Lys Thr Val Glu Glu Leu Lys Ala Gln Ala Asp Lys Met Lys Ala
            180                 185                 190

Glu Leu Glu Asp Lys Ala Ala Gln Ala Gly Thr Thr Val Glu Asp Gln
            195                 200                 205

Ile Lys Glu Ile Lys Ser Ala Ala Glu Asn Ala Glu Lys Ser Gln Asn
        210                 215                 220

Ala Ile Ser Val Glu Glu Ala Ala Glu Thr Leu Ser Glu Ala Glu Arg
225                 230                 235                 240
```

```
Thr Pro Thr Asp Leu Thr Ala Leu Glu Thr His Glu Lys Val Glu Leu
            245                 250                 255

Asn Thr His Leu Ser Ser Tyr Tyr Pro Pro Asp Asp Ile Glu Ile Ala
            260                 265                 270

Pro Ala Ser Lys Ser Gln Ser Ser Lys Thr Lys Ser
            275                 280

(2) INFORMATION FOR SEQ ID NO:3:

(i) SEQUENCE CHARACTERISTICS:
        (A) LENGTH: 22108 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:3:

AGTCCTGCAG AATGAAGGGT GATTTATGTG ATTTGCATCA CTTTTGGTGG GTAAATTTAT      60

GCAACGCATT TGCGTCATGG TGATGAGTAT CACGAAAAAA TGTTAAACCC TTCGGTAAAG     120

TGTCTTTTTG CTTCTTCTGA CTAAACCGAT TCACAGAGGA GTTGTATATG TCCAAGTCTG     180

ATGTTTTTCA TCTCGGCCTC ACTAAAAACG ATTTACAAGG GGCTACGCTT GCCATCGTCC     240

CTGGCGACCC GGATCGTGTG GAAAAGATCG CCGCGCTGAT GGATAAGCCG GTTAAGCTGG     300

CATCTCACCG CGAATTCACT ACCTGGCGTG CAGAGCTGGA TGGTAAACCT GTTATCGTCT     360

GCTCTACCGG TATCGGCGGC CCGTCTACCT CTATTGCTGT TGAAGAGCTG GCACAGCTGG     420

GCATTCGCAC CTTCCTGCGT ATCGGTACAA CGGGCGCTAT TCAGCCGCAT ATTAATGTGG     480

GTGATGTCCT GGTTACCACG GCGTCTGTCC GTCTGGATGG CGCGAGCCTG CACTTCGCAC     540

CGCTGGAATT CCCGGCTGTC GCTGATTTCG AATGTACGAC TGCGCTGGTT GAAGCTGCGA     600

AATCCATTGG CGCGACAACT CACGTTGGCG TGACAGCTTC TTCTGATACC TTCTACCCAG     660

GTCAGGAACG TTACGATACT TACTCTGGTC GCGTAGTTCG TCACTTTAAA GGTTCTATGG     720

AAGAGTGGCA GGCGATGGGC GTAATGAACT ATGAAATGGA ATCTGCAACC CTGCTGACCA     780

TGTGTGCAAG TCAGGGCCTG CGTGCCGGTA TGGTAGCGGG TGTTATCGTT AACCGCACCC     840

AGCAAGAGAT CCCGAATGCT GAGACGATGA AACAAACCGA AAGCCATGCG GTGAAAATCG     900

TGGTGGAAGC GGCGCGTCGT CTGCTGTAAT TCTCTTCTCC TGTCTGAAGG CCGACGCGTT     960

CGGCCTTTTG TATTTTTGCG TAGCGCCTCG CAGGAAATGC CTTTCCAACT GGACGTTTGT    1020

ACAGCACAAT TCTATTTTGT GCGGGTAAGT TGTTGCGTCA GGAGGCGTTG TGGATTTCTC    1080

AATCATGGTT TACGCAGTTA TTGCGTTGGT GGGTGTGGCA ATTGGCTGGC TGTTTGCCAG    1140

TTATCAACAT GCGCAGCAAA AAGCCGAGCA ATTAGCTGAA CGTGAAGAGA TGGTCGCGGA    1200

GTTAAGCGCG GCAAAACAAC AAATTACCCA AAGCGAGCAC TGGCGTGCAG AGTGCGAGTT    1260

ACTCAATAAC GAAGTGCGCA GCCTGCAAAG TATTAACACC TCTCTGGAGG CCGATCTGCG    1320

TGAAGTAACC ACGCGGATGG AAGCCGCACA GCAACATGCT GACGATAAAA TTCGCCAGAT    1380

GATTAACAGC GAGCAGCGCC TCAGTGAGCA GTTTGAAAAC CTCGCCAACC GTATTTTTGA    1440

GCACAGCAAT CGCCGGGTTG ATGAGCAAAA CCGTCAGAGT CTGAACAGCC TGTTGTCGCC    1500

GCTACGTGAA CAACTGGACG GTTTCCGCCG TCAGGTTCAG GACAGCTTCG GTAAAGAAGC    1560

ACAAGAACGC CATACCCTGA CCCACGAAAT TCGCAATCTC CAGCAACTCA ACGCGCAAAT    1620

GGCCCAGGAA GCGATCAACC TGACGCGCGC GCTGAAAGGC GACAATAAAA CCCAGGGCAA    1680

CTGGGGCGAG GTAGTATTGA CGCGGGTGCT GGAGGCTTCC GGTCTGCGTG AAGGGTATGA    1740
```

-continued

```
ATATGAAACC CAGGTCAGCA TCGAAAATGA CGCCCGCTCG CGGATGCAGC CGGATGTCAT    1800

CGTGCGCCTG CCGCAGGGAA AAGATGTGGT GATCGACGCC AAAATGACGC TGGTCGCCTA    1860

TGAACGCTAT TTTAACGCCG AAGACGACTA CACCCGCGAA AGCGCGCTAC AGGAACATAT    1920

CGCGTCGGTG CGTAACCATA TCCGTTTGCT GGGACGCAAA GATTATCAAC AGCTGCCGGG    1980

GCTGCGAACT CTGGATTACG TGCTGATGTT TATTCCCGTT GAACCCGCTT TTTTACTGGC    2040

GCTTGACCGC CAGCCGGAGC TGATCACCGA AGCGTTGAAA AACAACATCA TGCTGGTTAG    2100

CCCGACTACG CTGCTGGTGG CGCTGCGCAC TATCGCCAAC CTGTGGCGTT ATGAGCATCA    2160

AAGCCGCAAC GCCCAGCAAA TCGCCGATCG TGCCAGCAAG CTGTACGACA AGATGCGTTT    2220

GTTCATCGAT GACATGTCCG CGATTGGTCA AAGTCTCGAC AAAGCGCAGG ATAATTATCG    2280

GCAGGCAATG AAAAAACTCT CTTCAGGGCG CGGAAATGTG CTGGCGCAGG CAGAAGCGTT    2340

TCGCGGTTTA GGAGTAGAAA TTAAACGCGA GATTAATCCG GATTTGGCTG AACAGGCGGT    2400

GAGCCAGGAT GAAGAGTATC GACTTCGGTC GGTTCCGGAG CAGCCGAATG ATGAAGCTTA    2460

TCAACGCGAT GATGAATATA ATCAGCAGTC GCGCTAGCCC ATTGGGAGTA GTTAAGCCGG    2520

GTAGAAATCT AGGGCATCGA CGCCCAATCT GTTACACTTC TGGAACAATT TTTTGATGAG    2580

CAGGCATTGA GATGGTGGAT AAGTCACAAG AAACGACGCA CTTTGGTTTT CAGACCGTCG    2640

CGAAGGAACA AAAAGCGGAT ATGGTCGCCC ACGTTTTCCA TTCCGTGGCA TCAAAATACG    2700

ATGTCATGAA TGATTTGATG TCATTTGGTA TTCATCGTTT GTGGAAGCGA TTCACGATTG    2760

ATTGCAGCGG CGTACGCCGT GGGCAGACCG TGCTGGATCT GGCTGGTGGC ACCGGCGACC    2820

TGACAGCGAA ATTCTCCCGC CTGGTCGGAG AAACTGGCAA AGTGGTCCTT GCTGATATCA    2880

ATGAATCCAT GCCCAAAATG GGCCGCGAGA AGCTGCGTAA TATCGGTGTG ATTGGCAACG    2940

TTGAGTATGT TCAGGCGAAC GCTGAGGCGC TGCCGTTCCC GGATAACACC TTTGATTGCA    3000

TCACCATTTC GTTTGGTCTG CGTAACGTCA CCGACAAAGA TAAAGCACTG CGTTCAATGT    3060

ATCGCGTGCT GAAACCCGGC GGCCGCCTGC TGGTGCTTGA GTTCTCGAAG CCAATTATCG    3120

AGCCGCTGAG CAAAGCCTAT GATGCATACT CCTTCCATGT GCTGCCGCGT ATTGGCTCAC    3180

TGGTCGCGAA CGACGCCGAC AGCTACCGTT ATCTGGCAGA ATCCATCCGT ATGCATCCCG    3240

ATCAGGATAC CCTGAAAGCC ATGATGCAGG ATGCCGGATT CGAAAGTGTC GACTACTACA    3300

ATCTGACGGC AGGGGTTGTG GCGCTGCATC GTGGTTATAA GTTCTGACAG GAGACCGGAA    3360

ATGCCTTTTA AACCTTTAGT GACGGCAGGA ATTGAAAGTC TGCTCAACAC CTTCCTGTAT    3420

CGCTCACCCG CGCTGAAAAC GGCCCGCTCG CGTCTGCTGG GTAAAGTATT GCGCGTGGAG    3480

GTAAAAGGCT TTTCGACGTC ATTGATTCTG GTGTTCAGCG AACGCCAGGT TGATGTACTG    3540

GGCGAATGGG CAGGCGATGC TGACTGCACC GTTATCGCCT ACGCCAGTGT GTTGCCGAAA    3600

CTTCGCGATC GCCAGCAGCT TACCGCACTG ATTCGCAGTG GTGAGCTGGA AGTGCAGGGC    3660

GATATTCAGG TGGTGCAAAA CTTCGTTGCG CTGGCAGATC TGGCAGAGTT CGACCCTGCG    3720

GAACTGCTGG CCCCTTATAC CGGTGATATC GCCGCTGAAG GAATCAGCAA AGCCATGCGC    3780

GGAGGCGCAA AGTTCCTGCA TCACGGCATT AAGCGCCAGC AACGTTATGT GGCGGAAGCC    3840

ATTACTGAAG AGTGGCGTAT GGCACCCGGT CCGCTTGAAG TGGCCTGGTT TGCGGAAGAG    3900

ACGGCTGCCG TCGAGCGTGC TGTTGATGCC CTGACCAAAC GGCTGGAAAA ACTGGAGGCT    3960

AAATGACGCC AGGTGAAGTA CGGCGCCTAT ATTTCATCAT TCGCACTTTT TTAAGCTACG    4020

GACTTGATGA ACTGATCCCC AAAATGCGTA TCACCCTGCC GCTACGGCTA TGGCGATACT    4080
```

```
CATTATTCTG GATGCCAAAT CGGCATAAAG ACAAACTTTT AGGTGAGCGA CTACGACTGG    4140

CCCTGCAAGA ACTGGGGCCG GTTTGGATCA AGTTCGGGCA AATGTTATCA ACCCGCCGCG    4200

ATCTTTTTCC ACCGCATATT GCCGATCAGC TGGCGTTATT GCAGGACAAA GTTGCTCCGT    4260

TTGATGGCAA GCTGGCGAAG CAGCAGATTG AAGCTGCAAT GGGCGGCTTG CCGGTAGAAG    4320

CGTGGTTTGA CGATTTTGAA ATCAAGCCGC TGGCTTCTGC TTCTATCGCC CAGGTTCATA    4380

CCGCGCGATT GAAATCGAAT GGTAAAGAGG TGGTGATTAA AGTCATCCGC CCGGATATTT    4440

TGCCGGTTAT TAAAGCGGAT CTGAAACTTA TCTACCGTCT GGCTCGCTGG GTGCCGCGTT    4500

TGCTGCCGGA TGGTCGCCGT CTGCGCCCAA CCGAAGTGGT GCGCGAGTAC GAAAAGACAT    4560

TGATTGATGA ACTGAATTTG CTGCGGGAAT CTGCCAACGC CATTCAGCTT CGGCGCAATT    4620

TTGAAGACAG CCCGATGCTC TACATCCCGG AAGTTTACCC TGACTATTGT AGTGAAGGGA    4680

TGATGGTGAT GGAGCGCATT TACGGCATTC CGGTGTCTGA TGTTGCGGCG CTGGAGAAAA    4740

ACGGCACTAA CATGAAATTG CTGGCGGAAC GCGGCGTGCA GGTGTTCTTC ACTCAGGTCT    4800

TTCGCGACAG CTTTTTCCAT GCCGATATGC ACCCTGGCAA CATCTTCGTA AGCTATGAAC    4860

ACCCGGAAAA CCCGAAATAT ATCGGCATTG ATTGCGGGAT TGTTGGCTCG CTAAACAAAG    4920

AAGATAAACG CTATCTGGCA GAAAACTTTA TCGCCTTCTT TAATCGCGAC TATCGCAAAG    4980

TGGCAGAGCT ACACGTCGAT TCTGGCTGGG TGCCACCAGA TACCAACGTT GAAGAGTTCG    5040

AATTTGCCAT TCGTACGGTC TGTGAACCTA TCTTTGAGAA ACCGCTGGCC GAAATTTCGT    5100

TTGGACATGT ACTGTTAAAT CTGTTTAATA CGGCGCGTCG CTTCAATATG GAAGTGCAGC    5160

CGCAACTGGT GTTACTCCAG AAAACCCTGC TCTACGTCGA AGGGGTAGGA CGCCAGCTTT    5220

ATCCGCAACT CGATTTATGG AAAACGGCGA AGCCTTTCCT GGAGTCGTGG ATTAAAGATC    5280

AGGTCGGTAT TCCTGCGCTG GTGAGAGCAT TTAAAGAAAA AGCGCCGTTC TGGGTCGAAA    5340

AAATGCCAGA ACTGCCTGAA TTGGTTTACG ACAGTTTGCG CCAGGGCAAG TATTTACAGC    5400

ACAGTGTTGA TAAGATTGCC CGCGAGCTTC AGTCAAATCA TGTACGTCAG GACAATCGC    5460

GTTATTTTCT CGGAATTGGC GCTACGTTAG TATTAAGTGG CACATTCTTG TTGGTCAGCC    5520

GACCTGAATG GGGGCTGATG CCCGGCTGGT TAATGGCAGG TGGTCTGATC GCCTGGTTTG    5580

TCGGTTGGCG CAAAACACGC TGATTTTTTC ATCGCTCAAG GCGGGCCGTG TAACGTATAA    5640

TGCGGCTTTG TTTAATCATC ATCTACCACA GAGGAACATG TATGGGTGGT ATCAGTATTT    5700

GGCAGTTATT GATTATTGCC GTCATCGTTG TACTGCTTTT TGGCACCAAA AAGCTCGGCT    5760

CCATCGGTTC CGATCTTGGT GCGTCGATCA AAGGCTTTAA AAAAGCAATG AGCGATGATG    5820

AACCAAAGCA GGATAAAACC AGTCAGGATG CTGATTTTAC TGCGAAAACT ATCGCCGATA    5880

AGCAGGCGGA TACGAATCAG GAACAGGCTA AAACAGAAGA CGCGAAGCGC CACGATAAAG    5940

AGCAGGTGAA TCCGTGTTTG ATATCGGTTT TAGCGAACTT GCTATTGGTG TTCATCATCG    6000

GCCTCGTCGT TCTGGGGCCG CAACGACTGC CTGTGGCGGT AAAAACGGTA GCGGGCTGGA    6060

TTCGCGCGTT GCGTTCACTG GCGACAACGG TGCAGAACGA ACTGACCCAG GAGTTAAAAC    6120

TCCAGGAGTT TCAGGACAGT CTGAAAAAGG TTGAAAAGGC GAGCCTCACT AACCTGACGC    6180

CCGAACTGAA AGCGTCGATG GATGAACTAC GCCAGGCCGC GGAGTCGATG AAGCGTTCCT    6240

ACGTTGCAAA CGATCCTGAA AAGGCGAGCG ATGAAGCGCA CCATCCAT AACCCGGTGG    6300

TGAAAGATAA TGAAGCTGCG CATGAGGGCG TAACGCCTGC CGCTGCACAA ACGCAGGCCA    6360

GTTCGCCGGA ACAGAAGCCA GAAACCACGC CAGAGCCGGT GGTAAAACCT GCTGCGGACG    6420

CTGAACCGAA AACCGCTGCA CCTTCCCCTT CGTCGAGTGA TAAACCGTAA ACATGTCTGT    6480
```

```
AGAAGATACT CAACCGCTTA TCACGCATCT GATTGAGCTG CGTAAGCGTC TGCTGAACTG    6540

CATTATCGCG GTGATCGTGA TATTCCTGTG TCTGGTCTAT TTCGCCAATG ACATCTATCA    6600

CCTGGTATCC GCGCCATTGA TCAAGCAGTT GCCGCAAGGT TCAACGATGA TCGCCACCGA    6660

CGTGGCCTCG CCGTTCTTTA CGCCGATCAA GCTGACCTTT ATGGTGTCGC TGATTCTGTC    6720

AGCGCCGGTG ATTCTCTATC AGGTGTGGGC ATTTATCGCC CCAGCGCTGT ATAAGCATGA    6780

ACGTCGCCTG GTGGTGCCGC TGCTGGTTTC CAGCTCTCTG CTGTTTTATA TCGGCATGGC    6840

ATTCGCCTAC TTTGTGGTCT TTCCGCTGGC ATTTGGCTTC CTTGCCAATA CCGCGCCGGA    6900

AGGGGTGCAG GTATCCACCG ACATCGCCAG CTATTTAAGC TTCGTTATGG CGCTGTTTAT    6960

GGCGTTTGGT GTCTCCTTTG AAGTGCCGGT AGCAATTGTG CTGCTGTGCT GGATGGGGAT    7020

TACCTCGCCA GAAGACTTAC GCAAAAAACG CCCGTATGTG CTGGTTGGTG CATTCGTTGT    7080

CGGGATGTTG CTGACGCCGC CGGATGTCTT CTCGCAAACG CTGTTGGCGA TCCCGATGTA    7140

CTGTCTGTTT GAAATCGGTG TCTTCTTCTC ACGCTTTTAC GTTGGTAAAG GCGAAATCG    7200

GGAAGAGGAA AACGACGCTG AAGCAGAAAG CGAAAAAACT GAAGAATAAA TTCAACCGCC    7260

CGTCAGGGCG GTTGTCATAT GGAGTACAGG ATGTTTGATA TCGGCGTTAA TTTGACCAGT    7320

TCGCAATTTG CGAAAGACCG TGATGATGTT GTAGCGTGCG CTTTTGACGC GGGAGTTAAT    7380

GGGCTACTCA TCACCGGCAC TAACCTGCGT GAAAGCCAGC AGGCGCAAAA GCTGGCGCGT    7440

CAGTATTCGT CCTGTTGGTC AACGGCGGGC GTACATCCTC ACGACAGCAG CCAGTGGCAA    7500

GCTGCGACTG AAGAAGCGAT TATTGAGCTG GCCGCGCAGC CAGAAGTGGT GGCGATTGGT    7560

GAATGTGGTC TCGACTTTAA CCGCAACTTT TCGACGCCGG AAGAGCAGGA ACGCGCTTTT    7620

GTTGCCCAGC TACGCATTGC CGCAGATTTA AACATGCCGG TATTTATGCA CTGTCGCGAT    7680

GCCCACGAGC GGTTTATGAC ATTGCTGGAG CCGTGGCTGG ATAAACTGCC TGGTGCGGTT    7740

CTTCATTGCT TTACCGGCAC ACGCGAAGAG ATGCAGGCGT GCGTGGCGCA TGGAATTTAT    7800

ATCGGCATTA CCGGTTGGGT TTGCGATGAA CGACGCGGAC TGGAGCTGCG GGAACTTTTG    7860

CCGTTGATTC CGGCGGAAAA ATTACTGATC GAAACTGATG CGCCGTATCT GCTCCCTCGC    7920

GATCTCACGC CAAAGCCATC ATCCCGGCGC AACGAGCCAG CCCATCTGCC CCATATTTTG    7980

CAACGTATTG CGCACTGGCG TGGAGAAGAT GCCGCATGGC TGGCTGCCAC CACGGATGCT    8040

AATGTCAAAA CACTGTTTGG GATTGCGTTT TAGAGTTTGC GGAACTCGGT ATTCTTCACA    8100

CTGTGCTTAA TCTCTTTATT AATAAGATTA AGCAATAGCA TGGAGCGAGC CTCACCATCG    8160

GGTTCGGTGA AAATGGCCTG AAAGCCTTCG AACGCGCCTT CGGTAATAAT CACCTTATCA    8220

CCCGGATAAG GGGTTGCCGG ATCGACAATG TCTTTCGGTT TATATACCGA TAGCTGATGA    8280

ATAACCGCCG ATGGGACTAT CGCTGGCGAC GCGCCAAAGC GCACGAAGTG GCTGACACCG    8340

CGGGTCGCGT TGATAGTCGT GGTATGAATC ACTTCTGGGT CAAATTCCAC AAACAGGTAG    8400

TTGGGGAACA ATGGCTCACT GACTGCAGTA CGTTTTCCAC GCACGATTTT TCCAGGGTG    8460

ATCATCGGTG CCAGGCAATT CACAGCCTGT CTTTCGAGGT GTTCCTGGGC ACGTTGAAGT    8520

TGCCCGCGCT TGCAGTACAG TAAATACCAG GATTGCATAA TGACTCTTAT CCGTTTAATC    8580

GGGGCGCAAG GATAGCAAAA GCTTTACGCT AAGTTAATTA TATTCCCCGG TTTGCGTTAT    8640

ACCGTCAGAG TTCACGCTAA TTTAACAAAT TTACAGCATC GCAAAGATGA ACGCCGTATA    8700

ATGGGCGCAG ATTAAGAGGC TACAATGGAC GCCATGAAAT ATAACGATTT ACGCGACTTC    8760

TTGACGCTGC TTGAACAGCA GGGTGAGCTA AAACGTATCA CGCTCCCGGT GGATCCGCAT    8820
```

-continued

| | |
|---|---|
| CTGGAAATCA CTGAAATTGC TGACCGCACT TTGCGTGCCG GTGGGCCTGC GCTGTTGTTC | 8880 |
| GAAAACCCTA AAGGCTACTC AATGCCGGTG CTGTGCAACC TGTTCGGTAC GCCAAAGCGC | 8940 |
| GTGGCGATGG GCATGGGGCA GGAAGATGTT TCGGCGCTGC GTGAAGTTGG TAAATTATTG | 9000 |
| GCGTTTCTGA AAGAGCCGGA GCCGCCAAAA GGTTTCCGCG ACCTGTTTGA TAAACTGCCG | 9060 |
| CAGTTTAAGC AAGTATTGAA CATGCCGACA AAGCGGCTGC GTGGTGCGCC CTGCCAACAA | 9120 |
| AAAATCGTCT CTGGCGATGA CGTCGATCTC AATCGCATTC CCATTATGAC CTGCTGGCCG | 9180 |
| GAAGATGCCG CGCCGCTGAT TACCTGGGGG CTGACAGTGA CGCGCGGCCC ACATAAAGAG | 9240 |
| CGGCAGAATC TGGGCATTTA TCGCCAGCAG CTGATTGGTA AAAACAAACT GATTATGCGC | 9300 |
| TGGCTGTCGC ATCGCGGCGG CGCGCTGGAT TATCAGGAGT GGTGTGCGGC GCATCCGGGC | 9360 |
| GAACGTTTCC CGGTTTCTGT GGCGCTGGGT GCCGATCCCG CCACGATTCT CGGTGCAGTC | 9420 |
| ACTCCCGTTC CGGATACGCT TTCAGAGTAT GCGTTTGCCG GATTGCTACG TGGCACCAAG | 9480 |
| ACCGAAGTGG TGAAGTGTAT CTCCAATGAT CTTGAAGTGC CCGCCAGTGC GGAGATTGTG | 9540 |
| CTGGAAGGGT ATATCGAACA AGGCGAAACT GCGCCGGAAG GGCCGTATGG CGACCACACC | 9600 |
| GGTTACTATA ATGAAGTCGA TAGTTTCCCG GTATTTACCG TGACGCATAT TACCCAGCGT | 9660 |
| GAAGATGCGA TTTACCATTC CACCTATACC GGGCGTCCGC CAGATGAGCC CGCGGTGCTG | 9720 |
| GGTGTCGCAC TGAACGAAGT GTTTGTGCCG ATTCTGCAAA ACAGTTCCC GGAAATTGTC | 9780 |
| GATTTTTACC TGCCGCCGGA AGGCTGCTCT TATCGCCTGG CGGTAGTGAC AATCAAAAAA | 9840 |
| CAGTACGCCG GACACGCGAA GCGCGTCATG ATGGGCGTCT GGTCGTTCTT ACGCCAGTTT | 9900 |
| ATGTACACTA AATTTGTGAT CGTTTGCGAT GATGACGTTA ACGACGCGA CTGGAACGAT | 9960 |
| GTGATTTGGG CGATTACCAC CCGTATGGAC CCGGCGCGGG ATACTGTTCT GGTAGAAAAT | 10020 |
| ACGCCTATTG ATTATCTGGA TTTTGCCTCG CCTGTCTCCG GCTGGGTTC AAAAATGGGG | 10080 |
| CTGGATGCCA CGAATAAATG GCCGGGGGAA ACCCAGCGTG AATGGGGACG TCCCATCAAA | 10140 |
| AAAGATCCAG ATGTTGTCGC GCATATTGAC GCCATCTGGG ATGAACTGGC TATTTTTAAC | 10200 |
| AACGGTAAAA GCGCCTGATG CGCGTTTGTT TTGCCCTATT TATCGATCCG ACAGAGAAAG | 10260 |
| CGCATGACAA CCTTAAGCTG TAAAGTGACC TCGGTAGAAG CTATCACGGA TACCGTATAT | 10320 |
| CGTGTCCGCA TCGTGCCAGA CGCGGCCTTT TCTTTTCGTG CTGGTCAGTA TTTGATGGTA | 10380 |
| GTGATGGATG AGCGCGACAA ACGTCCGTTC TCAATGGCTT CGACGCCGGA TGAAAAAGGG | 10440 |
| TTTATCGAGC TGCATATTGG CGCTTCTGAA ATCAACCTTT ACGCGAAAGC AGTCATGGAC | 10500 |
| CGCATCCTCA AGATCATCA AATCGTGGTC GACATTCCCC ACGGAGAAGC GTGGCTGCGC | 10560 |
| GATGATGAAG AGCGTCCGAT GATTTTGATT GCGGGCGGCA CCGGGTTCTC TTATGCCCGC | 10620 |
| TCGATTTTGC TGACAGCGTT GGCGCGTAAC CCAAACCGTG ATATCACCAT TTACTGGGGC | 10680 |
| GGGCGTGAAG AGCAGCATCT GTATGATCTC TGCGAGCTTG AGGCGCTTTC GTTGAAGCAT | 10740 |
| CCTGGTCTGC AAGTGGTGCC GGTGGTTGAA CAACCGGAAG CGGGCTGGCG TGGGCGTACT | 10800 |
| GGCACCGTGT TAACGGCGGT ATTGCAGGAT CACGGTACGC TGGCAGAGCA TGATATCTAT | 10860 |
| ATTGCCGGAC GTTTTGAGAT GGCGAAAATT GCCCGCGATC TGTTTTGCAG TGAGCGTAAT | 10920 |
| GCGCGGGAAG ATCGCCTGTT TGGCGATGCG TTTGCATTTA TCTGAGATAT AAAAAAACCC | 10980 |
| GCCCCTGACA GGCGGGAAGA ACGGCAACTA AACTGTTATT CAGTGGCATT TAGATCTATG | 11040 |
| ACGTATCTGG CAAAAGTCCT GCAGAATGAA GGGTGATTTA TGTGATTTGC ATCACTTTTG | 11100 |
| GTGGGTAAAT TTATGCAACG CATTTGCGTC ATGGTGATGA GTATCACGAA AAAATGTTAA | 11160 |
| ACCCTTCGGT AAAGTGTCTT TTTGCTTCTT CTGACTAAAC CGATTCACAG AGGAGTTGTA | 11220 |

```
TATGTCCAAG TCTGATGTTT TTCATCTCGG CCTCACTAAA AACGATTTAC AAGGGGCTAC   11280

GCTTGCCATC GTCCCTGGCG ACCCGGATCG TGTGGAAAAG ATCGCCGCGC TGATGGATAA   11340

GCCGGTTAAG CTGGCATCTC ACCGCGAATT CACTACCTGG CGTGCAGAGC TGGATGGTAA   11400

ACCTGTTATC GTCTGCTCTA CCGGTATCGG CGGCCCGTCT ACCTCTATTG CTGTTGAAGA   11460

GCTGGCACAG CTGGGCATTC GCACCTTCCT GCGTATCGGT ACAACGGGCG CTATTCAGCC   11520

GCATATTAAT GTGGGTGATG TCCTGGTTAC CACGGCGTCT GTCCGTCTGG ATGGCGCGAG   11580

CCTGCACTTC GCACCGCTGG AATTCCCGGC TGTCGCTGAT TTCGAATGTA CGACTGCGCT   11640

GGTTGAAGCT GCGAAATCCA TTGGCGCGAC AACTCACGTT GGCGTGACAG CTTCTTCTGA   11700

TACCTTCTAC CCAGGTCAGG AACGTTACGA TACTTACTCT GGTCGCGTAG TTCGTCACTT   11760

TAAAGGTTCT ATGGAAGAGT GGCAGGCGAT GGGCGTAATG AACTATGAAA TGGAATCTGC   11820

AACCCTGCTG ACCATGTGTG CAAGTCAGGG CCTGCGTGCC GGTATGGTAG CGGGTGTTAT   11880

CGTTAACCGC ACCCAGCAAG AGATCCCGAA TGCTGAGACG ATGAAACAAA CCGAAAGCCA   11940

TGCGGTGAAA ATCGTGGTGG AAGCGGCGCG TCGTCTGCTG TAATTCTCTT CTCCTGTCTG   12000

AAGGCCGACG CGTTCGGCCT TTTGTATTTT TGCGTAGCGC CTCGCAGGAA ATGCCTTTCC   12060

AACTGGACGT TTGTACAGCA CAATTCTATT TTGTGCGGGT AAGTTGTTGC GTCAGGAGGC   12120

GTTGTGGATT TCTCAATCAT GGTTTACGCA GTTATTGCGT TGGTGGGTGT GGCAATTGGC   12180

TGGCTGTTTG CCAGTTATCA ACATGCGCAG CAAAAAGCCG AGCAATTAGC TGAACGTGAA   12240

GAGATGGTCG CGGAGTTAAG CGCGGCAAAA CAACAAATTA CCCAAAGCGA GCACTGGCGT   12300

GCAGAGTGCG AGTTACTCAA TAACGAAGTG CGCAGCCTGC AAAGTATTAA CACCTCTCTG   12360

GAGGCCGATC TGCGTGAAGT AACCACGCGG ATGGAAGCCG CACAGCAACA TGCTGACGAT   12420

AAAATTCGCC AGATGATTAA CAGCGAGCAG CGCCTCAGTG AGCAGTTTGA AAACCTCGCC   12480

AACCGTATTT TTGAGCACAG CAATCGCCGG GTTGATGAGC AAAACCGTCA GAGTCTGAAC   12540

AGCCTGTTGT CGCCGCTACG TGAACAACTG GACGGTTTCC GCCGTCAGGT TCAGGACAGC   12600

TTCGGTAAAG AAGCACAAGA ACGCCATACC CTGACCCACG AAATTCGCAA TCTCCAGCAA   12660

CTCAACGCGC AAATGGCCCA GGAAGCGATC AACCTGACGC GCGCGCTGAA AGGCGACAAT   12720

AAAACCCAGG GCAACTGGGG CGAGGTAGTA TTGACGCGGG TGCTGGAGGC TTCCGGTCTG   12780

CGTGAAGGGT ATGAATATGA AACCCAGGTC AGCATCGAAA ATGACGCCCG CTCGCGGATG   12840

CAGCCGGATG TCATCGTGCG CCTGCCGCAG GGAAAAGATG TGGTGATCGA CGCCAAAATG   12900

ACGCTGGTCG CCTATGAACG CTATTTTAAC GCCGAAGACG ACTACACCCG CGAAAGCGCG   12960

CTACAGGAAC ATATCGCGTC GGTGCGTAAC CATATCCGTT TGCTGGGACG CAAAGATTAT   13020

CAACAGCTGC CGGGGCTGCG AACTCTGGAT TACGTGCTGA TGTTTATTCC CGTTGAACCC   13080

GCTTTTTTAC TGGCGCTTGA CCGCCAGCCG GAGCTGATCA CCGAAGCGTT GAAAAACAAC   13140

ATCATGCTGG TTAGCCCGAC TACGCTGCTG GTGGCGCTGC GCACTATCGC CAACCTGTGG   13200

CGTTATGAGC ATCAAAGCCG CAACGCCCAG CAAATCGCCG ATCGTGCCAG CAAGCTGTAC   13260

GACAAGATGC GTTTGTTCAT CGATGACATG TCCGCGATTG GTCAAAGTCT CGACAAAGCG   13320

CAGGATAATT ATCGGCAGGC AATGAAAAAA CTCTCTTCAG GGCGCGGAAA TGTGCTGGCG   13380

CAGGCAGAAG CGTTTCGCGG TTTAGGAGTA GAAATTAAAC GCGAGATTAA TCCGGATTTG   13440

GCTGAACAGG CGGTGAGCCA GGATGAAGAG TATCGACTTC GGTCGGTTCC GGAGCAGCCG   13500

AATGATGAAG CTTATCAACG CGATGATGAA TATAATCAGC AGTCGCGCTA GCCCATTGGG   13560
```

-continued

```
AGTAGTTAAG CCGGGTAGAA ATCTAGGGCA TCGACGCCCA ATCTGTTACA CTTCTGGAAC    13620
AATTTTTTGA TGAGCAGGCA TTGAGATGGT GGATAAGTCA CAAGAAACGA CGCACTTTGG    13680
TTTTCAGACC GTCGCGAAGG AACAAAAAGC GGATATGGTC GCCCACGTTT TCCATTCCGT    13740
GGCATCAAAA TACGATGTCA TGAATGATTT GATGTCATTT GGTATTCATC GTTTGTGGAA    13800
GCGATTCACG ATTGATTGCA GCGGCGTACG CCGTGGGCAG ACCGTGCTGG ATCTGGCTGG    13860
TGGCACCGGC GACCTGACAG CGAAATTCTC CCGCCTGGTC GGAGAAACTG GCAAAGTGGT    13920
CCTTGCTGAT ATCAATGAAT CCATGCCCAA AATGGGCCGC GAGAAGCTGC GTAATATCGG    13980
TGTGATTGGC AACGTTGAGT ATGTTCAGGC GAACGCTGAG GCGCTGCCGT TCCCGGATAA    14040
CACCTTTGAT TGCATCACCA TTTCGTTTGG TCTGCGTAAC GTCACCGACA AGATAAAGC    14100
ACTGCGTTCA ATGTATCGCG TGCTGAAACC CGGCGGCCGC CTGCTGGTGC TTGAGTTCTC    14160
GAAGCCAATT ATCGAGCCGC TGAGCAAAGC CTATGATGCA TACTCCTTCC ATGTGCTGCC    14220
GCGTATTGGC TCACTGGTCG CGAACGACGC CGACAGCTAC CGTTATCTGG CAGAATCCAT    14280
CCGTATGCAT CCCGATCAGG ATACCCTGAA AGCCATGATG CAGGATGCCG GATTCGAAAG    14340
TGTCGACTAC TACAATCTGA CGGCAGGGGT TGTGGCGCTG CATCGTGGTT ATAAGTTCTG    14400
ACAGGAGACC GGAAATGCCT TTTAAACCTT TAGTGACGGC AGGAATTGAA AGTCTGCTCA    14460
ACACCTTCCT GTATCGCTCA CCCGCGCTGA AAACGGCCCG CTCGCGTCTG CTGGGTAAAG    14520
TATTGCGCGT GGAGGTAAAA GGCTTTTCGA CGTCATTGAT TCTGGTGTTC AGCGAACGCC    14580
AGGTTGATGT ACTGGGCGAA TGGGCAGGCG ATGCTGACTG CACCGTTATC GCCTACGCCA    14640
GTGTGTTGCC GAAACTTCGC GATCGCCAGC AGCTTACCGC ACTGATTCGC AGTGGTGAGC    14700
TGGAAGTGCA GGGCGATATT CAGGTGGTGC AAAACTTCGT TGCGCTGGCA GATCTGGCAG    14760
AGTTCGACCC TGCGGAACTG CTGGCCCCTT ATACCGGTGA TATCGCCGCT GAAGGAATCA    14820
GCAAAGCCAT GCGCGGAGGC GCAAAGTTCC TGCATCACGG CATTAAGCGC CAGCAACGTT    14880
ATGTGGCGGA AGCCATTACT GAAGAGTGGC GTATGGCACC CGGTCCGCTT GAAGTGGCCT    14940
GGTTTGCGGA AGAGACGGCT GCCGTCGAGC GTGCTGTTGA TGCCCTGACC AAACGGCTGG    15000
AAAAACTGGA GGCTAAATGA CGCCAGGTGA AGTACGGCGC CTATATTTCA TCATTCGCAC    15060
TTTTTTAAGC TACGGACTTG ATGAACTGAT CCCCAAAATG CGTATCACCC TGCCGCTACG    15120
GCTATGGCGA TACTCATTAT TCTGGATGCC AAATCGGCAT AAAGACAAAC TTTTAGGTGA    15180
GCGACTACGA CTGCCCTGC AAGAACTGGG GCCGGTTTGG ATCAAGTTCG GGCAAATGTT    15240
ATCAACCCGC CGCGATCTTT TTCCACCGCA TATTGCCGAT CAGCTGGCGT TATTGCAGGA    15300
CAAAGTTGCT CCGTTTGATG GCAAGCTGGC GAAGCAGCAG ATTGAAGCTG CAATGGGCGG    15360
CTTGCCGGTA GAAGCGTGGT TGACGATTTT TGAAATCAAG CCGCTGGCTT CTGCTTCTAT    15420
CGCCCAGGTT CATACCGCGC GATTGAAATC GAATGGTAAA GAGGTGGTGA TTAAAGTCAT    15480
CCGCCCGGAT ATTTTGCCGG TTATTAAAGC GGATCTGAAA CTTATCTACC GTCTGGCTCG    15540
CTGGGTGCCG CGTTTGCTGC CGGATGGTCG CCGTCTGCGC CAACCGAAG TGGTGCGCGA    15600
GTACGAAAAG ACATTGATTG ATGAACTGAA TTTGCTGCGG GAATCTGCCA ACGCCATTCA    15660
GCTTCGGCGC AATTTTGAAG ACAGCCCGAT GCTCTACATC CCGGAAGTTT ACCCTGACTA    15720
TTGTAGTGAA GGGATGATGG TGATGGAGCG CATTTACGGC ATTCCGGTGT CTGATGTTGC    15780
GGCGCTGGAG AAAAACGGCA CTAACATGAA ATTGCTGGCG GAACGCGGCG TGCAGGTGTT    15840
CTTCACTCAG GTCTTTCGCG ACAGCTTTTT CCATGCCGAT ATGCACCCTG GCAACATCTT    15900
CGTAAGCTAT GAACACCCGG AAAACCCGAA ATATATCGGC ATTGATTGCG GGATTGTTGG    15960
```

-continued

```
CTCGCTAAAC AAAGAAGATA AACGCTATCT GGCAGAAAAC TTTATCGCCT TCTTTAATCG     16020

CGACTATCGC AAAGTGGCAG AGCTACACGT CGATTCTGGC TGGGTGCCAC CAGATACCAA     16080

CGTTGAAGAG TTCGAATTTG CCATTCGTAC GGTCTGTGAA CCTATCTTTG AGAAACCGCT     16140

GGCCGAAATT TCGTTTGGAC ATGTACTGTT AAATCTGTTT AATACGGCGC GTCGCTTCAA     16200

TATGGAAGTG CAGCCGCAAC TGGTGTTACT CCAGAAAACC CTGCTCTACG TCGAAGGGGT     16260

AGGACGCCAG CTTTATCCGC AACTCGATTT ATGGAAAACG GCGAAGCCTT TCCTGGAGTC     16320

GTGGATTAAA GATCAGGTCG GTATTCCTGC GCTGGTGAGA GCATTTAAAG AAAAAGCGCC     16380

GTTCTGGGTC GAAAAAATGC CAGAACTGCC TGAATTGGTT TACGACAGTT TGCGCCAGGG     16440

CAAGTATTTA CAGCACAGTG TTGATAAGAT TGCCCGCGAG CTTCAGTCAA ATCATGTACG     16500

TCAGGGACAA TCGCGTTATT TTCTCGGAAT TGGCGCTACG TTAGTATTAA GTGGCACATT     16560

CTTGTTGGTC AGCCGACCTG AATGGGGGCT GATGCCCGGC TGGTTAATGG CAGGTGGTCT     16620

GATCGCCTGG TTTGTCGGTT GGCGCAAAAC ACGCTGATTT TTTCATCGCT CAAGGCGGGC     16680

CGTGTAACGT ATAATGCGGC TTTGTTTAAT CATCATCTAC CACAGAGGAA CATGTATGGG     16740

TGGTATCAGT ATTTGGCAGT TATTGATTAT TGCCGTCATC GTTGTACTGC TTTTTGGCAC     16800

CAAAAAGCTC GGCTCCATCG GTTCCGATCT TGGTGCGTCG ATCAAAGGCT TTAAAAAAGC     16860

AATGAGCGAT GATGAACCAA AGCAGGATAA AACCAGTCAG GATGCTGATT TTACTGCGAA     16920

AACTATCGCC GATAAGCAGG CGGATACGAA TCAGGAACAG GCTAAAACAG AAGACGCGAA     16980

GCGCCACGAT AAAGAGCAGG TGAATCCGTG TTTGATATCG GTTTTAGCGA ACTTGCTATT     17040

GGTGTTCATC ATCGGCCTCG TCGTTCTGGG GCCGCAACGA CTGCCTGTGG CGGTAAAAAC     17100

GGTAGCGGGC TGGATTCGCG CGTTGCGTTC ACTGGCGACA ACGGTGCAGA ACGAACTGAC     17160

CCAGGAGTTA AAACTCCAGG AGTTTCAGGA CAGTCTGAAA AAGGTTGAAA AGGCGAGCCT     17220

CACTAACCTG ACGCCCGAAC TGAAAGCGTC GATGGATGAA CTACGCCAGG CCGCGGAGTC     17280

GATGAAGCGT TCCTACGTTG CAAACGATCC TGAAAAGGCG AGCGATGAAG CGCACACCAT     17340

CCATAACCCG GTGGTGAAAG ATAATGAAGC TGCGCATGAG GGCGTAACGC CTGCCGCTGC     17400

ACAAACGCAG GCCAGTTCGC CGGAACAGAA GCCAGAAACC ACGCCAGAGC CGGTGGTAAA     17460

ACCTGCTGCG GACGCTGAAC CGAAAACCGC TGCACCTTCC CCTTCGTCGA GTGATAAACC     17520

GTAAACATGT CTGTAGAAGA TACTCAACCG CTTATCACGC ATCTGATTGA GCTGCGTAAG     17580

CGTCTGCTGA ACTGCATTAT CGCGGTGATC GTGATATTCC TGTGTCTGGT CTATTTCGCC     17640

AATGACATCT ATCACCTGGT ATCCGCGCCA TTGATCAAGC AGTTGCCGCA AGGTTCAACG     17700

ATGATCGCCA CCGACGTGGC CTCGCCGTTC TTTACGCCGA TCAAGCTGAC CTTTATGGTG     17760

TCGCTGATTC TGTCAGCGCC GGTGATTCTC TATCAGGTGT GGGCATTTAT CGCCCCAGCG     17820

CTGTATAAGC ATGAACGTCG CCTGGTGGTG CCGCTGCTGG TTTCCAGCTC TCTGCTGTTT     17880

TATATCGGCA TGGCATTCGC CTACTTTGTG GTCTTTCCGC TGGCATTTGG CTTCCTTGCC     17940

AATACCGCGC CGGAAGGGGT GCAGGTATCC ACCGACATCG CCAGCTATTT AAGCTTCGTT     18000

ATGGCGCTGT TTATGGCGTT TGGTGTCTCC TTTGAAGTGC CGGTAGCAAT TGTGCTGCTG     18060

TGCTGGATGG GGATTACCTC GCCAGAAGAC TTACGCAAAA AACGCCCGTA TGTGCTGGTT     18120

GGTGCATTCG TTGTCGGGAT GTTGCTGACG CCGCCGGATG TCTTCTCGCA AACGCTGTTG     18180

GCGATCCCGA TGTACTGTCT GTTTGAAATC GGTGTCTTCT TCTCACGCTT TTACGTTGGT     18240

AAAGGGCGAA ATCGGGAAGA GGAAAACGAC GCTGAAGCAG AAAGCGAAAA AACTGAAGAA     18300
```

-continued

```
TAAATTCAAC CGCCCGTCAG GGCGGTTGTC ATATGGAGTA CAGGATGTTT GATATCGGCG    18360
TTAATTTGAC CAGTTCGCAA TTTGCGAAAG ACCGTGATGA TGTTGTAGCG TGCGCTTTTG    18420
ACGCGGGAGT TAATGGGCTA CTCATCACCG GCACTAACCT GCGTGAAAGC CAGCAGGCGC    18480
AAAAGCTGGC GCGTCAGTAT TCGTCCTGTT GGTCAACGGC GGGCGTACAT CCTCACGACA    18540
GCAGCCAGTG GCAAGCTGCG ACTGAAGAAG CGATTATTGA GCTGGCCGCG CAGCCAGAAG    18600
TGGTGGCGAT TGGTGAATGT GGTCTCGACT TTAACCGCAA CTTTTCGACG CCGGAAGAGC    18660
AGGAACGCGC TTTTGTTGCC CAGCTACGCA TTGCCGCAGA TTTAAACATG CCGGTATTTA    18720
TGCACTGTCG CGATGCCCAC GAGCGGTTTA TGACATTGCT GGAGCCGTGG CTGGATAAAC    18780
TGCCTGGTGC GGTTCTTCAT TGCTTTACCG GCACACGCGA AGAGATGCAG GCGTGCGTGG    18840
CGCATGGAAT TTATATCGGC ATTACCGGTT GGGTTTGCGA TGAACGACGC GGACTGGAGC    18900
TGCGGGAACT TTTGCCGTTG ATTCCGGCGG AAAAATTACT GATCGAAACT GATGCGCCGT    18960
ATCTGCTCCC TCGCGATCTC ACGCCAAAGC CATCATCCCG GCGCAACGAG CCAGCCCATC    19020
TGCCCCATAT TTTGCAACGT ATTGCGCACT GGCGTGGAGA AGATGCCGCA TGGCTGGCTG    19080
CCACCACGGA TGCTAATGTC AAAACACTGT TTGGGATTGC GTTTTAGAGT TTGCGGAACT    19140
CGGTATTCTT CACACTGTGC TTAATCTCTT TATTAATAAG ATTAAGCAAT AGCATGGAGC    19200
GAGCCTCACC ATCGGGTTCG GTGAAAATGG CCTGAAAGCC TTCGAACGCG CCTTCGGTAA    19260
TAATCACCTT ATCACCCGGA TAAGGGGTTG CCGGATCGAC AATGTCTTTC GGTTTATATA    19320
CCGATAGCTG ATGAATAACC GCCGATGGGA CTATCGCTGG CGACGCGCCA AAGCGCACGA    19380
AGTGGCTGAC ACCGCGGGTC GCGTTGATAG TCGTGGTATG AATCACTTCT GGGTCAAATT    19440
CCACAAACAG GTAGTTGGGG AACAATGGCT CACTGACTGC AGTACGTTTT CCACGCACGA    19500
TTTTTTCCAG GGTGATCATC GGTGCCAGGC AATTCACAGC CTGTCTTTCG AGGTGTTCCT    19560
GGGCACGTTG AAGTTGCCCG CGCTTGCAGT ACAGTAAATA CCAGGATTGC ATAATGACTC    19620
TTATCCGTTT AATCGGGGCG CAAGGATAGC AAAAGCTTTA CGCTAAGTTA ATTATATTCC    19680
CCGGTTTGCG TTATACCGTC AGAGTTCACG CTAATTTAAC AAATTTACAG CATCGCAAAG    19740
ATGAACGCCG TATAATGGGC GCAGATTAAG AGGCTACAAT GGACGCCATG AAATATAACG    19800
ATTTACGCGA CTTCTTGACG CTGCTTGAAC AGCAGGGTGA GCTAAAACGT ATCACGCTCC    19860
CGGTGGATCC GCATCTGGAA ATCACTGAAA TTGCTGACCG CACTTTGCGT GCCGGTGGGC    19920
CTGCGCTGTT GTTCGAAAAC CCTAAAGGCT ACTCAATGCC GGTGCTGTGC AACCTGTTCG    19980
GTACGCCAAA GCGCGTGGCG ATGGGCATGG GCAGGAAGA TGTTTCGGCG CTGCGTGAAG    20040
TTGGTAAATT ATTGGCGTTT CTGAAAGAGC CGGAGCCGCC AAAAGGTTTC CGCGACCTGT    20100
TTGATAAACT GCCGCAGTTT AAGCAAGTAT TGAACATGCC GACAAAGCGG CTGCGTGGTG    20160
CGCCCTGCCA ACAAAAAATC GTCTCTGGCG ATGACGTCGA TCTCAATCGC ATTCCCATTA    20220
TGACCTGCTG GCCGGAAGAT GCCGCGCCGC TGATTACCTG GGGGCTGACA GTGACGCGCG    20280
GCCCACATAA AGAGCGGCAG AATCTGGCA TTTATCGCCA GCAGCTGATT GGTAAAAACA    20340
AACTGATTAT GCGCTGGCTG TCGCATCGCG GCGGCGCGCT GGATTATCAG GAGTGGTGTG    20400
CGGCGCATCC GGGCGAACGT TTCCCGGTTT CTGTGGCGCT GGGTGCCGAT CCCGCCACGA    20460
TTCTCGGTGC AGTCACTCCC GTTCCGGATA CGCTTTCAGA GTATGCGTTT GCCGGATTGC    20520
TACGTGGCAC CAAGACCGAA GTGGTGAAGT GTATCTCCAA TGATCTTGAA GTGCCCGCCA    20580
GTGCGGAGAT TGTGCTGGAA GGGTATATCG AACAAGGCGA AACTGCGCCG GAAGGGCCGT    20640
ATGGCGACCA CACCGGTTAC TATAATGAAG TCGATAGTTT CCCGGTATTT ACCGTGACGC    20700
```

| | | | | | |
|---|---|---|---|---|---|
|ATATTACCCA|GCGTGAAGAT|GCGATTTACC|ATTCCACCTA|TACCGGGCGT|CCGCCAGATG 20760|
|AGCCCGCGGT|GCTGGGTGTC|GCACTGAACG|AAGTGTTTGT|GCCGATTCTG|CAAAAACAGT 20820|
|TCCCGGAAAT|TGTCGATTTT|TACCTGCCGC|CGGAAGGCTG|CTCTTATCGC|CTGGCGGTAG 20880|
|TGACAATCAA|AAAACAGTAC|GCCGGACACG|CGAAGCGCGT|CATGATGGGC|GTCTGGTCGT 20940|
|TCTTACGCCA|GTTTATGTAC|ACTAAATTTG|TGATCGTTTG|CGATGATGAC|GTTAACGCAC 21000|
|GCGACTGGAA|CGATGTGATT|TGGGCGATTA|CCACCCGTAT|GGACCCGGCG|CGGGATACTG 21060|
|TTCTGGTAGA|AAATACGCCT|ATTGATTATC|TGGATTTTGC|CTCGCCTGTC|TCCGGGCTGG 21120|
|GTTCAAAAAT|GGGGCTGGAT|GCCACGAATA|AATGGCCGGG|GGAAACCCAG|CGTGAATGGG 21180|
|GACGTCCCAT|CAAAAAAGAT|CCAGATGTTG|TCGCGCATAT|TGACGCCATC|TGGGATGAAC 21240|
|TGGCTATTTT|TAACAACGGT|AAAAGCGCCT|GATGCGCGTT|TGTTTTGCCC|TATTTATCGA 21300|
|TCCGACAGAG|AAAGCGCATG|ACAACCTTAA|GCTGTAAAGT|GACCTCGGTA|GAAGCTATCA 21360|
|CGGATACCGT|ATATCGTGTC|CGCATCGTGC|CAGACGCGGC|CTTTTCTTTT|CGTGCTGGTC 21420|
|AGTATTTGAT|GGTAGTGATG|GATGAGCGCG|ACAAACGTCC|GTTCTCAATG|GCTTCGACGC 21480|
|CGGATGAAAA|AGGGTTTATC|GAGCTGCATA|TTGGCGCTTC|TGAAATCAAC|CTTTACGCGA 21540|
|AAGCAGTCAT|GGACCGCATC|CTCAAAGATC|ATCAAATCGT|GGTCGACATT|CCCCACGGAG 21600|
|AAGCGTGGCT|GCGCGATGAT|GAAGAGCGTC|CGATGATTTT|GATTGCGGGC|GGCACCGGGT 21660|
|TCTCTTATGC|CCGCTCGATT|TGCTGACAG|CGTTGGCGCG|TAACCCAAAC|CGTGATATCA 21720|
|CCATTTACTG|GGGCGGGCGT|GAAGAGCAGC|ATCTGTATGA|TCTCTGCGAG|CTTGAGGCGC 21780|
|TTTCGTTGAA|GCATCCTGGT|CTGCAAGTGG|TGCCGGTGGT|TGAACAACCG|GAAGCGGGCT 21840|
|GGCGTGGGCG|TACTGGCACC|GTGTTAACGG|CGGTATTGCA|GGATCACGGT|ACGCTGGCAG 21900|
|AGCATGTATAT|CTATATTGCC|GGACGTTTTG|AGATGGCGAA|AATTGCCCGC|GATCTGTTTT 21960|
|GCAGTGAGCG|TAATGCGCGG|GAAGATCGCC|TGTTTGGCGA|TGCGTTTGCA|TTTATCTGAG 22020|
|ATATAAAAAA|ACCCGCCCCT|GACAGGCGGG|AAGAACGGCA|ACTAAACTGT|TATTCAGTGG 22080|
|CATTTAGATC|TATGACGTAT|CTGGCAAA| | |22108|

(2) INFORMATION FOR SEQ ID NO:4:

(i) SEQUENCE CHARACTERISTICS:
        (A) LENGTH: 831 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:4:

| | | | | | |
|---|---|---|---|---|---|
|ATGCGGCTTT|GTTTAATCAT|CATCTACCAC|AGAGGAACAT|GTATGGGTGG|TATCAGTATT 60|
|TGGCAGTTAT|TGATTATTGC|CGTCATCGTT|GTACTGCTTT|TTGGCACCAA|AAAGCTCGGC 120|
|TCCATCGGTT|CCGATCTTGG|TGCGTCGATC|AAAGGCTTTA|AAAAAGCAAT|GAGCGATGAT 180|
|GAACCAAAGC|AGGATAAAAC|CAGTCAGGAT|GCTGATTTTA|CTGCGAAAAC|TATCGCCGAT 240|
|AAGCAGGCGG|ATACGAATCA|GGAACAGGCT|AAAACAGAAG|ACGCGAAGCG|CCACGATAAA 300|
|GAGCAGGTGA|ATCCGTGTTT|GATATCGGTT|TTAGCGAACT|TGCTATTGGT|GTTCATCATC 360|
|GGCCTCGTCG|TTCTGGGGCC|GCAACGACTG|CCTGTGGCGG|TAAAAACGGT|AGCGGGCTGG 420|
|ATTCGCGCGT|TGCGTTCACT|GGCGACAACG|GTGCAGAACG|AACTGACCCA|GGAGTTAAAA 480|
|CTCCAGGAGT|TTCAGGACAG|TCTGAAAAAG|GTTGAAAAGG|CGAGCCTCAC|TAACCTGACG 540|

```
CCCGAACTGA AAGCGTCGAT GGATGAACTA CGCCAGGCCG CGGAGTCGAT GAAGCGTTCC    600

TACGTTGCAA ACGATCCTGA AAAGGCGAGC GATGAAGCGC ACACCATCCA TAACCCGGTG    660

GTGAAAGATA ATGAAGCTGC GCATGAGGGC GTAACGCCTG CCGCTGCACA AACGCAGGCC    720

AGTTCGCCGG AACAGAAGCC AGAAACCACG CCAGAGCCGG TGGTAAAACC TGCTGCGGAC    780

GCTGAACCGA AAACCGCTGC ACCTTCCCCT TCGTCGAGTG ATAAACCGTA A            831
```

(2) INFORMATION FOR SEQ ID NO:5:

(i) SEQUENCE CHARACTERISTICS:
        (A) LENGTH: 778 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:5:

```
ATGTCTGTAG AAGATACTCA ACCGCTTATC ACGCATCTGA TTGAGCTGCG TAAGCGTCTG     60

CTGAACTGCA TTATCGCGGT GATCGTGATA TTCCTGTGTC TGGTCTATTT CGCCAATGAC    120

ATCTATCACC TGGTATCCGC GCCATTGATC AAGCAGTTGC CGCAAGGTTC AACGATGATC    180

GCCACCGACG TGGCCTCGCC GTTCTTTACG CCGATCAAGC TGACCTTTAT GGTGTCGCTG    240

ATTCTGTCAG CGCCGGTGAT TCTCTATCAG GTGTGGGCAT TTATCGCCCC AGCGCTGTAT    300

AAGCATGAAC GTCGCCTGGT GGTGCCGCTG CTGGTTTCCA GCTCTCTGCT GTTTTATATC    360

GGCATGGCAT TCGCCTACTT TGTGGTCTTT CCGCTGGCAT TTGGCTTCCT TGCCAATACC    420

GCGCCGGAAG GGGTGCAGGT ATCCACCGAC ATCGCCAGCT ATTTAAGCTT CGTTATGGCG    480

CTGTTTATGG CGTTTGGTGT CTCCTTTGAA GTGCCGGTAG CAATTGTGCT GCTGTGCTGG    540

ATGGGGATTA CCTCGCCAGA AGACTTACGC AAAAAACGCC CGTATGTGCT GGTTGGTGCA    600

TTCGTTGTCG GGATGTTGCT GACGCCGCCG GATGTCTTCT CGCAAACGCT GTTGGCGATC    660

CCGATGTACT GTCTGTTTGA AATCGGTGTC TTCTTCTCAC GCTTTTACGT TGGTAAAGGG    720

CGAAATCGGG AAGAGGAAAA CGACGCTGAA GCAGAAAGCG AAAAAACTGA AGAATAAA     778
```

(2) INFORMATION FOR SEQ ID NO:6:

(i) SEQUENCE CHARACTERISTICS:
        (A) LENGTH: 795 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:6:

```
ATGGAGTACA GGATGTTTGA TATCGGCGTT AATTTGACCA GTTCGCAATT TGCGAAAGAC     60

CGTGATGATG TTGTAGCGTG CGCTTTTGAC GCGGGAGTTA ATGGGCTACT CATCACCGGC    120

ACTAACCTGC GTGAAAGCCA GCAGGCGCAA AAGCTGGCGC GTCAGTATTC GTCCTGTTGG    180

TCAACGGCGG GCGTACATCC TCACGACAGC AGCCAGTGGC AAGCTGCGAC TGAAGAAGCG    240

ATTATTGAGC TGGCCGCGCA GCCAGAAGTG GTGGCGATTG TGAATGTGG TCTCGACTTT    300

AACCGCAACT TTTCGACGCC GGAAGAGCAG GAACGCGCTT TGTTGCCCA GCTACGCATT    360

GCCGCAGATT TAAACATGCC GGTATTTATG CACTGTCGCG ATGCCCACGA GCGGTTTATG    420

ACATTGCTGG AGCCGTGGCT GGATAAACTG CCTGGTGCGG TTCTTCATTG CTTTACCGGC    480
```

```
ACACGCGAAG AGATGCAGGC GTGCGTGGCG CATGGAATTT ATATCGGCAT TACCGGTTGG    540

GTTTGCGATG AACGACGCGG ACTGGAGCTG CGGGAACTTT TGCCGTTGAT TCCGGCGGAA    600

AAATTACTGA TCGAAACTGA TGCGCCGTAT CTGCTCCCTC GCGATCTCAC GCCAAAGCCA    660

TCATCCCGGC GCAACGAGCC AGCCCATCTG CCCCATATTT TGCAACGTAT TGCGCACTGG    720

CGTGGAGAAG ATGCCGCATG GCTGGCTGCC ACCACGGATG CTAATGTCAA AACACTGTTT    780

GGGATTGCGT TTTAG                                                     795
```

(2) INFORMATION FOR SEQ ID NO:7:

(i) SEQUENCE CHARACTERISTICS:
        (A) LENGTH: 258 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:7:

```
Met Ser Val Glu Asp Thr Gln Pro Leu Ile Thr His Leu Ile Glu Leu
 1               5                  10                  15

Arg Lys Arg Leu Leu Asn Cys Ile Ile Ala Val Ile Val Ile Phe Leu
                20                  25                  30

Cys Leu Val Tyr Phe Ala Asn Asp Ile Tyr His Leu Val Ser Ala Pro
            35                  40                  45

Leu Ile Lys Gln Leu Pro Gln Gly Ser Thr Met Ile Xaa Xaa Asp Val
        50                  55                  60

Ala Ser Pro Phe Phe Thr Pro Ile Lys Leu Thr Phe Met Val Ser Leu
65                  70                  75                  80

Ile Leu Ser Ala Pro Val Ile Leu Tyr Gln Val Trp Ala Phe Ile Ala
                85                  90                  95

Pro Ala Leu Tyr Lys His Glu Arg Arg Leu Val Val Pro Leu Leu Val
               100                 105                 110

Ser Ser Ser Leu Leu Phe Leu Tyr Arg His Ala Phe Ala Tyr Phe Val
           115                 120                 125

Val Phe Pro Leu Ala Phe Gly Phe Leu Ala Asn Thr Ala Pro Glu Gly
       130                 135                 140

Val Gln Val Ser Thr Asp Ile Ala Ser Tyr Leu Ser Phe Val Met Ala
145                 150                 155                 160

Leu Phe Met Ala Phe Gly Val Ser Phe Glu Val Pro Val Ala Ile Val
               165                 170                 175

Leu Leu Cys Trp Met Gly Ile Thr Ser Pro Glu Asp Leu Arg Lys Lys
           180                 185                 190

Arg Pro Tyr Val Leu Val Gly Ala Phe Val Val Gly Met Leu Leu Thr
       195                 200                 205

Pro Pro Asp Val Phe Ser Gln Thr Leu Leu Ala Ile Pro Met Tyr Cys
210                 215                 220

Leu Phe Glu Ile Gly Val Phe Phe Ser Arg Phe Tyr Val Gly Lys Gly
225                 230                 235                 240

Arg Asn Arg Glu Glu Glu Asn Asp Ala Glu Ala Glu Ser Glu Lys Thr
               245                 250                 255

Glu Glu
```

(2) INFORMATION FOR SEQ ID NO:8:

(i) SEQUENCE CHARACTERISTICS:

(A) LENGTH: 264 amino acids
          (B) TYPE: amino acid
          (C) STRANDEDNESS: Not Relevant
          (D) TOPOLOGY: unknown (ii) MOLECULE TYPE: protein (xi) SEQUENCE DESCRIPTION: SEQ ID NO:8:

```
Met Glu Tyr Arg Met Phe Asp Ile Gly Val Asn Leu Thr Ser Ser Gln
1               5                  10                  15

Phe Ala Lys Asp Arg Asp Asp Val Val Ala Cys Ala Phe Asp Ala Gly
                20                  25                  30

Val Asn Gly Leu Leu Ile Thr Gly Thr Asn Leu Arg Glu Ser Gln Gln
                35                  40                  45

Ala Gln Lys Leu Ala Arg Gln Tyr Ser Ser Cys Trp Ser Thr Ala Gly
        50                  55                  60

Val His Pro His Asp Ser Ser Gln Trp Gln Ala Ala Thr Glu Glu Ala
65                  70                  75                  80

Ile Ile Glu Leu Ala Ala Gln Pro Glu Val Val Ala Ile Gly Glu Cys
                85                  90                  95

Gly Leu Asp Phe Asn Arg Asn Phe Ser Thr Pro Glu Glu Gln Glu Arg
                100                 105                 110

Ala Phe Val Ala Gln Leu Arg Ile Ala Ala Asp Leu Asn Met Pro Val
                115                 120                 125

Phe Met His Cys Arg Asp Ala His Glu Arg Phe Met Thr Leu Leu Glu
    130                 135                 140

Pro Trp Leu Asp Lys Leu Pro Gly Ala Val Leu His Cys Phe Thr Gly
145                 150                 155                 160

Thr Arg Glu Glu Met Gln Ala Cys Val Ala His Gly Ile Tyr Ile Gly
                165                 170                 175

Ile Thr Gly Trp Val Cys Asp Gly Arg Arg Gly Leu Glu Leu Arg Glu
                180                 185                 190

Leu Leu Pro Leu Ile Pro Ala Glu Lys Leu Leu Ile Glu Thr Asp Ala
            195                 200                 205

Pro Tyr Leu Leu Pro Arg Asp Leu Thr Pro Lys Pro Ser Ser Arg Arg
    210                 215                 220

Asn Glu Pro Ala His Leu Pro His Ile Leu Gln Arg Ile Ala His Trp
225                 230                 235                 240

Arg Gly Glu Asp Ala Ala Trp Leu Ala Ala Thr Thr Asp Ala Asn Val
                245                 250                 255

Lys Thr Leu Phe Gly Ile Ala Phe
                260
```

(2) INFORMATION FOR SEQ ID NO:9:

(i) SEQUENCE CHARACTERISTICS:
        (A) LENGTH: 243 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:9:

```
Met Thr Pro Thr Ala Asn Leu Leu Leu Pro Ala Pro Pro Phe Val Pro
1               5                   10                  15

Ile Ser Asp Val Arg Arg Leu Gln Leu Pro Pro Arg Val Arg His Gln
                20                  25                  30
```

```
Pro Arg Pro Cys Trp Lys Gly Val Glu Trp Gly Ser Ile Gln Thr Arg
        35                  40                  45

Met Val Ser Ser Phe Val Ala Val Gly Ser Arg Thr Arg Arg Arg Asn
 50                  55                  60

Val Ile Cys Ala Ser Leu Phe Gly Val Gly Ala Pro Glu Ala Leu Val
 65                  70                  75                  80

Ile Gly Val Val Ala Leu Leu Val Phe Gly Pro Lys Gly Leu Ala Glu
                 85                  90                  95

Val Ala Arg Asn Leu Gly Lys Thr Leu Arg Ala Phe Gln Pro Thr Ile
                100                 105                 110

Arg Glu Leu Gln Asp Val Ser Arg Glu Phe Arg Ser Thr Leu Glu Arg
                115                 120                 125

Glu Ile Gly Ile Asp Glu Val Ser Gln Ser Thr Asn Tyr Arg Pro Thr
                130                 135                 140

Thr Met Asn Asn Asn Gln Gln Pro Ala Ala Asp Pro Asn Val Lys Pro
145                 150                 155                 160

Glu Pro Ala Pro Tyr Thr Ser Glu Glu Leu Met Lys Val Thr Glu Glu
                165                 170                 175

Gln Ile Ala Ala Ser Ala Ala Ala Trp Asn Pro Gln Gln Pro Ala
                180                 185                 190

Thr Ser Gln Gln Gln Glu Glu Ala Pro Thr Thr Pro Arg Ser Glu Asp
                195                 200                 205

Ala Pro Thr Ser Gly Gly Ser Asp Gly Pro Ala Ala Pro Ala Arg Ala
                210                 215                 220

Val Ser Asp Ser Asp Pro Asn Gln Val Asn Lys Ser Gln Lys Ala Glu
225                 230                 235                 240

Gly Glu Arg (2) INFORMATION FOR SEQ ID NO:10:

(i) SEQUENCE CHARACTERISTICS:
        (A) LENGTH: 67 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:10:

Met Gly Glu Ile Ser Ile Thr Lys Leu Leu Val Val Ala Ala Leu Val
 1               5                  10                  15

Val Leu Leu Phe Gly Thr Lys Lys Leu Arg Thr Leu Gly Gly Asp Leu
                 20                  25                  30

Gly Ala Ala Ile Lys Gly Phe Lys Lys Ala Met Asn Asp Asp Asp Ala
                 35                  40                  45

Ala Ala Lys Lys Gly Ala Asp Val Asp Leu Gln Ala Glu Lys Leu Ser
     50                  55                  60

His Lys Glu
65

(2) INFORMATION FOR SEQ ID NO:11:

(i) SEQUENCE CHARACTERISTICS:
        (A) LENGTH: 126 amino acids
        (B) TYPE: amino acid
        (C) STRANDEDNESS: Not Relevant
        (D) TOPOLOGY: unknown (ii) MOLECULE TYPE: protein
```

(xi) SEQUENCE DESCRIPTION: SEQ ID NO:11:

Met Ala Leu Thr Leu Val Met Gly Ala Ile Ala Ser Pro Trp Val Ser
1               5                   10                  15

Val Gly Thr Lys Leu Cys Tyr Ser Arg Leu Asn Glu Ser Phe Tyr Pro
                20                  25                  30

Ser Asn Pro Leu Thr Ala Pro Asn Pro Met Asn Ile Phe Gly Ile Gly
                35                  40                  45

Leu Pro Glu Leu Gly Leu Ile Phe Val Ile Ala Leu Leu Val Phe Gly
        50                  55                  60

Pro Lys Lys Leu Pro Glu Val Gly Arg Ser Leu Gly Lys Ala Leu Arg
65                  70                  75                  80

Gly Phe Gln Glu Ala Ser Lys Glu Phe Glu Thr Glu Leu Lys Arg Glu
            85                  90                  95

Ala Gln Asn Leu Glu Lys Ser Val Gln Ile Lys Ala Glu Leu Glu Glu
                100                 105                 110

Ser Lys Thr Pro Glu Ser Ser Ser Ser Glu Lys Ala Ser
            115                 120                 125

(2) INFORMATION FOR SEQ ID NO:12:

(i) SEQUENCE CHARACTERISTICS:
        (A) LENGTH: 98 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:12:

Met Gly Ala Met Ser Pro Trp His Trp Ala Ile Val Ala Leu Val Val
1               5                   10                  15

Val Ile Leu Phe Gly Ser Lys Lys Leu Pro Asp Ala Ala Arg Gly Leu
                20                  25                  30

Gly Arg Ser Leu Arg Ile Phe Lys Ser Glu Val Lys Glu Met Gln Asn
            35                  40                  45

Asp Asn Ser Thr Pro Ala Pro Thr Ala Gln Ser Ala Pro Pro Pro Gln
50                  55                  60

Ser Ala Pro Ala Glu Leu Pro Val Ala Asp Thr Thr Thr Ala Pro Val
65                  70                  75                  80

Thr Pro Pro Ala Pro Val Gln Pro Gln Ser Gln His Thr Glu Pro Lys
            85                  90                  95

Ser Ala (2) INFORMATION FOR SEQ ID NO:13:

(i) SEQUENCE CHARACTERISTICS:
        (A) LENGTH: 58 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:13:

Met Met Gly Ile Ser Val Trp Gln Leu Leu Ile Ile Leu Leu Ile Val
1               5                   10                  15

Val Met Leu Phe Gly Thr Lys Arg Leu Arg Gly Leu Gly Ser Asp Leu
                20                  25                  30

```
Gly Ser Ala Ile Asn Gly Phe Arg Lys Ser Val Ser Asp Gly Glu Thr
        35                  40                  45

Thr Thr Gln Ala Glu Ala Ser Ser Arg Ser
        50                  55
```

(2) INFORMATION FOR SEQ ID NO:14:

(i) SEQUENCE CHARACTERISTICS:
        (A) LENGTH: 88 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:14:

```
Met Gly Ser Leu Ser Pro Trp His Trp Val Val Leu Val Val Val
1               5                   10                  15

Val Leu Leu Phe Gly Ala Lys Lys Leu Pro Asp Ala Ala Arg Ser Leu
        20                  25                  30

Gly Lys Ser Met Arg Ile Phe Lys Ser Glu Leu Arg Glu Met Gln Thr
        35                  40                  45

Glu Asn Gln Ala Gln Ala Ser Ala Leu Glu Thr Pro Met Gln Asn Pro
        50                  55                  60

Thr Val Val Gln Ser Gln Arg Val Val Pro Pro Trp Ser Thr Glu Gln
65              70                  75                  80

Asp His Thr Glu Ala Arg Pro Ala
                85
```

(2) INFORMATION FOR SEQ ID NO:15:

(i) SEQUENCE CHARACTERISTICS:
        (A) LENGTH: 79 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:15:

```
Met Gly Gly Phe Thr Ser Ile Trp His Trp Val Ile Val Leu Leu Val
1               5                   10                  15

Ile Val Leu Leu Phe Gly Ala Lys Lys Ile Pro Glu Leu Ala Lys Gly
        20                  25                  30

Leu Gly Ser Gly Ile Lys Asn Phe Lys Lys Ala Val Lys Asp Asp Glu
        35                  40                  45

Glu Glu Ala Lys Asn Glu Pro Lys Thr Leu Asp Ala Gln Ala Thr Gln
        50                  55                  60

Thr Lys Val His Glu Ser Ser Glu Ile Lys Ser Lys Gln Glu Ser
65              70                  75
```

(2) INFORMATION FOR SEQ ID NO:16:

(i) SEQUENCE CHARACTERISTICS:
        (A) LENGTH: 109 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:16:

Met Ala Lys Lys Ser Ile Phe Arg Ala Lys Phe Phe Leu Phe Tyr Arg

-continued

```
1               5                   10                  15
Thr Glu Phe Ile Met Phe Gly Leu Ser Pro Ala Gln Leu Ile Ile Leu
                20                  25                  30

Leu Val Val Ile Leu Leu Ile Phe Gly Thr Lys Lys Leu Arg Asn Ala
                35                  40                  45

Gly Ser Asp Leu Gly Ala Ala Val Lys Gly Phe Lys Lys Ala Met Lys
50                      55                  60

Glu Asp Glu Lys Val Lys Asp Ala Glu Phe Lys Ser Ile Asp Asn Glu
65                  70                  75                  80

Thr Ala Ser Ala Lys Lys Gly Lys Tyr Lys Arg Glu Arg Asn Arg Leu
                85                  90                  95

Asn Pro Cys Leu Ile Leu Val Phe Gln Asn Leu Phe Tyr
                100                 105
```

(2) INFORMATION FOR SEQ ID NO:17:

(i) SEQUENCE CHARACTERISTICS:
        (A) LENGTH: 57 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:17:

```
Met Pro Ile Gly Pro Gly Ser Leu Ala Val Ile Ala Ile Val Ala Leu
1               5                   10                  15

Ile Ile Phe Gly Pro Lys Lys Leu Pro Glu Leu Gly Lys Ala Ala Gly
                20                  25                  30

Asp Thr Leu Arg Glu Phe Lys Asn Ala Thr Lys Gly Leu Thr Ser Asp
                35                  40                  45

Glu Glu Glu Lys Lys Lys Glu Asp Gln
50                  55
```

(2) INFORMATION FOR SEQ ID NO:18:

(i) SEQUENCE CHARACTERISTICS:
        (A) LENGTH: 192 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:18:

```
Met Gly Phe Gly Gly Ile Ser Ile Trp Gln Leu Leu Ile Ile Leu Leu
1               5                   10                  15

Ile Val Val Met Leu Phe Gly Thr Lys Arg Leu Lys Ser Leu Gly Ser
                20                  25                  30

Asp Leu Gly Asp Ala Ile Lys Gly Phe Arg Lys Ser Met Asp Asn Glu
                35                  40                  45

Glu Asn Lys Ala Pro Pro Val Glu Glu Gln Lys Gly Gln Asp His Arg
50                  55                  60

Gly Pro Gly Pro Gln Gly Arg Gly Thr Gly Gln Glu Arg Leu Ser Met
65                  70                  75                  80

Phe Asp Ile Gly Phe Ser Glu Leu Leu Leu Val Gly Leu Val Ala Leu
                85                  90                  95

Leu Val Leu Gly Pro Glu Arg Leu Pro Val Ala Ala Arg Met Ala Gly
                100                 105                 110
```

```
Leu Trp Ile Gly Arg Leu Lys Arg Ser Phe Asn Thr Leu Lys Thr Glu
        115                 120                 125

Val Glu Arg Glu Ile Gly Ala Asp Glu Ile Arg Arg Gln Leu His Asn
    130                 135                 140

Glu Arg Ile Leu Glu Leu Glu Arg Glu Met Lys Gln Ser Leu Gln Pro
145                 150                 155                 160

Pro Ala Pro Ser Ala Pro Asp Glu Thr Ala Ala Ser Pro Ala Thr Pro
                165                 170                 175

Pro Gln Pro Ala Ser Pro Ala Ala His Ser Asp Lys Thr Pro Ser Pro
        180                 185                 190
```

(2) INFORMATION FOR SEQ ID NO:19:

(i) SEQUENCE CHARACTERISTICS:
        (A) LENGTH: 158 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:19:

```
Thr Glu His Leu Glu Glu Leu Arg Gln Arg Thr Val Phe Val Phe Ile
1               5                   10                  15

Phe Phe Leu Leu Ala Ala Thr Ile Ser Phe Thr Gln Ile Lys Ile Ile
            20                  25                  30

Val Glu Ile Phe Gln Ala Pro Ala Ile Gly Ile Lys Phe Leu Gln Leu
        35                  40                  45

Ala Pro Gly Glu Tyr Phe Phe Ser Ser Ile Lys Ile Ala Ile Tyr Cys
50                  55                  60

Gly Ile Val Ala Thr Thr Pro Phe Gly Val Tyr Gln Val Ile Leu Tyr
65                  70                  75                  80

Ile Leu Pro Gly Leu Thr Asn Lys Glu Arg Lys Val Ile Leu Pro Ile
                85                  90                  95

Leu Ile Gly Ser Ile Val Leu Phe Ile Val Gly Gly Ile Phe Ala Tyr
            100                 105                 110

Phe Val Leu Ala Pro Ala Ala Leu Asn Phe Leu Ile Ser Tyr Gly Ala
        115                 120                 125

Asp Ile Val Glu Pro Leu Trp Ser Phe Glu Gln Tyr Phe Asp Phe Ile
        130                 135                 140

Leu Leu Leu Leu Phe Ser Thr Gly Leu Ala Phe Glu Ile Pro
145                 150                 155
```

(2) INFORMATION FOR SEQ ID NO:20:

(i) SEQUENCE CHARACTERISTICS:
        (A) LENGTH: 168 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:20:

```
Lys Thr Ile Leu Glu Glu Val Arg Ile Arg Val Phe Trp Ile Leu Ile
1               5                   10                  15

Cys Phe Ser Phe Thr Trp Phe Thr Cys Tyr Trp Phe Ser Glu Glu Phe
            20                  25                  30

Ile Phe Leu Leu Ala Lys Pro Phe Leu Thr Leu Pro Tyr Leu Asp Ser
        35                  40                  45
```

```
Ser Phe Ile Cys Thr Gln Leu Thr Glu Ala Leu Ser Thr Tyr Val Thr
    50                  55                  60

Thr Ser Leu Ile Ser Cys Phe Tyr Phe Leu Phe Pro Phe Leu Ser Tyr
 65                  70                  75                  80

Gln Ile Trp Cys Phe Leu Met Pro Ser Cys Tyr Glu Glu Arg Lys
                 85                  90                  95

Lys Tyr Asn Lys Leu Phe Tyr Leu Ser Gly Phe Cys Phe Phe Leu Phe
            100                 105                 110

Phe Phe Val Thr Phe Val Trp Ile Val Pro Asn Val Trp His Phe Leu
            115                 120                 125

Tyr Lys Leu Ser Thr Thr Ser Thr Asn Leu Leu Ile Ile Lys Leu Gln
            130                 135                 140

Pro Lys Ile Phe Asp Tyr Ile Met Leu Thr Val Arg Ile Leu Phe Ile
145                 150                 155                 160

Ser Ser Ile Cys Ser Gln Val Pro
                165
```

(2) INFORMATION FOR SEQ ID NO:21:

(i) SEQUENCE CHARACTERISTICS:
        (A) LENGTH: 167 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:21:

```
Glu Thr Ile Leu Gly Glu Val Arg Ile Arg Ser Val Arg Ile Leu Ile
 1               5                  10                  15

Gly Leu Gly Leu Thr Trp Phe Thr Cys Tyr Trp Phe Pro Glu Glu Leu
             20                  25                  30

Ile Ser Pro Leu Ala Ser Pro Phe Leu Thr Leu Pro Phe Asp Ser Tyr
             35                  40                  45

Phe Val Cys Thr Gln Leu Thr Glu Ala Phe Ser Thr Phe Val Ala Thr
    50                  55                  60

Ser Ser Ile Ala Cys Ser Tyr Phe Val Phe Pro Leu Ile Ser Tyr Gln
 65                  70                  75                  80

Ile Trp Cys Phe Leu Ile Pro Ser Cys Tyr Gly Glu Gln Arg Thr Lys
                 85                  90                  95

Tyr Asn Arg Phe Leu His Leu Ser Gly Ser Arg Phe Phe Leu Phe Leu
            100                 105                 110

Phe Leu Thr Pro Pro Arg Val Val Pro Asn Val Trp His Phe Pro Tyr
            115                 120                 125

Phe Val Gly Ala Thr Ser Thr Asn Ser Leu Met Ile Lys Leu Gln Pro
            130                 135                 140

Lys Ile Tyr Asp His Ile Met Leu Thr Val Arg Ile Ser Phe Ile Pro
145                 150                 155                 160

Ser Val Cys Ser Gln Val Pro
                165
```

(2) INFORMATION FOR SEQ ID NO:22:

(i) SEQUENCE CHARACTERISTICS:
        (A) LENGTH: 163 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:22:

```
Leu Thr His Leu Tyr Glu Ile Arg Leu Arg Ile Ile Tyr Leu Leu Tyr
 1               5                  10                  15

Ser Ile Phe Leu Thr Cys Phe Cys Ser Tyr Gln Tyr Lys Glu Glu Ile
             20                  25                  30

Phe Tyr Leu Leu Phe Ile Pro Leu Ser Lys Asn Phe Ile Tyr Thr Asp
             35                  40                  45

Leu Ile Glu Ala Phe Ile Thr Tyr Ile Lys Leu Ser Ile Ile Val Gly
 50                  55                  60

Ile Tyr Leu Ser Tyr Pro Ile Phe Leu Tyr Gln Ile Trp Ser Phe Leu
 65              70                  75                      80

Ile Pro Gly Phe Phe Leu Tyr Glu Lys Lys Leu Phe Arg Leu Leu Cys
                 85                  90                  95

Leu Thr Ser Ile Phe Leu Tyr Phe Leu Gly Ser Cys Ile Gly Tyr Tyr
                100                 105                 110

Leu Leu Phe Pro Ile Ala Phe Thr Phe Phe Leu Gly Phe Gln Lys Leu
            115                 120                 125

Gly Lys Asp Gln Leu Phe Thr Ile Glu Leu Gln Ala Lys Ile His Glu
130                 135                 140

Tyr Leu Ile Leu Asn Thr Lys Leu Ile Phe Ser Leu Ser Ile Cys Phe
145                 150                 155                 160

Gln Leu Pro
```

(2) INFORMATION FOR SEQ ID NO:23:

(i) SEQUENCE CHARACTERISTICS:
        (A) LENGTH: 158 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:23:

```
Phe Asp His Leu Asp Glu Leu Arg Thr Arg Ile Phe Leu Ser Leu Gly
 1               5                  10                  15

Ala Val Leu Val Gly Val Val Ala Cys Phe Ile Phe Val Lys Pro Leu
             20                  25                  30

Val Gln Trp Leu Gln Val Pro Ala Gly Thr Val Lys Phe Leu Gln Leu
             35                  40                  45

Ser Pro Gly Glu Phe Phe Val Ser Val Lys Val Ala Gly Tyr Ser
 50                  55                  60

Gly Ile Leu Val Met Ser Pro Phe Ile Leu Tyr Gln Ile Ile Gln Phe
 65              70                  75                      80

Val Leu Pro Gly Leu Thr Arg Arg Glu Arg Arg Leu Leu Gly Pro Val
                 85                  90                  95

Val Leu Gly Ser Ser Val Leu Phe Phe Ala Gly Leu Gly Phe Ala Tyr
                100                 105                 110

Tyr Ala Leu Ile Pro Ala Ala Leu Lys Phe Phe Val Ser Tyr Gly Ala
            115                 120                 125

Asp Val Val Glu Gln Leu Trp Ser Ile Asp Lys Tyr Phe Glu Phe Val
130                 135                 140

Leu Leu Leu Met Phe Ser Thr Gly Leu Ala Phe Gln Ile Pro
145                 150                 155
```

(2) INFORMATION FOR SEQ ID NO:24:

(i) SEQUENCE CHARACTERISTICS:
        (A) LENGTH: 178 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:24:

```
Val Asp His Leu Thr Glu Leu Arg Thr Arg Leu Leu Ile Ser Leu Ala
1               5                   10                  15

Ala Ile Leu Val Thr Thr Ile Phe Gly Phe Val Trp Tyr Ser His Ser
            20                  25                  30

Ile Phe Gly Leu Asp Ser Leu Gly Glu Trp Leu Arg His Pro Tyr Cys
                35                  40                  45

Ala Leu Pro Gln Ser Ala Arg Ala Asp Ile Ser Ala Asp Gly Glu Cys
        50                  55                  60

Arg Leu Leu Ala Thr Ala Pro Phe Asp Gln Phe Met Leu Arg Leu Lys
65                  70                  75                  80

Val Gly Met Ala Ala Gly Ile Val Leu Ala Cys Pro Val Trp Phe Tyr
                85                  90                  95

Gln Leu Trp Ala Phe Ile Thr Pro Gly Leu Tyr Gln Arg Glu Arg Arg
                100                 105                 110

Phe Ala Val Ala Phe Val Ile Pro Ala Ala Val Leu Phe Val Ala Gly
            115                 120                 125

Ala Val Leu Ala Tyr Leu Val Leu Ser Lys Ala Leu Gly Phe Leu Leu
        130                 135                 140

Thr Val Gly Ser Asp Val Gln Val Thr Ala Leu Ser Gly Asp Arg Tyr
145                 150                 155                 160

Phe Gly Phe Leu Leu Asn Leu Val Val Phe Gly Val Ser Phe Glu
                165                 170                 175

Phe Pro
```

(2) INFORMATION FOR SEQ ID NO:25:

(i) SEQUENCE CHARACTERISTICS:
        (A) LENGTH: 155 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:25:

```
His Leu Gln Glu Leu Arg Lys Arg Leu Met Val Ser Val Gly Thr Ile
1               5                   10                  15

Leu Val Ala Phe Leu Gly Cys Phe His Phe Trp Lys Ser Ile Phe Glu
            20                  25                  30

Phe Val Lys Asn Ser Tyr Lys Gly Thr Leu Ile Gln Leu Ser Pro Ile
            35                  40                  45

Glu Gly Val Met Val Ala Val Lys Ile Ser Phe Ser Ala Ala Ile Val
        50                  55                  60

Ile Ser Met Pro Ile Ile Phe Trp Gln Leu Trp Leu Phe Ile Ala Pro
65                  70                  75                  80

Gly Leu Tyr Lys Asn Glu Lys Lys Val Ile Leu Pro Phe Val Phe Phe
                85                  90                  95
```

```
Gly Ser Gly Met Phe Leu Ile Gly Ala Ala Phe Ser Tyr Tyr Val Val
            100                 105                 110

Phe Pro Phe Ile Ile Glu Tyr Leu Ala Thr Phe Gly Ser Asp Val Phe
        115                 120                 125

Ala Ala Asn Ile Ser Ala Ser Ser Tyr Val Ser Phe Phe Thr Arg Leu
        130                 135                 140

Ile Leu Gly Phe Gly Val Ala Phe Glu Leu Pro
145                 150                 155

(2) INFORMATION FOR SEQ ID NO:26:

(i) SEQUENCE CHARACTERISTICS:
        (A) LENGTH: 163 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:26:

Ile Thr His Leu Val Glu Leu Arg Asn Arg Leu Leu Arg Cys Val Ile
1               5                   10                  15

Cys Val Val Leu Val Phe Val Ala Leu Val Tyr Phe Ser Asn Asp Ile
            20                  25                  30

Tyr His Phe Val Ala Ala Pro Leu Thr Ala Val Met Pro Lys Gly Ala
            35                  40                  45

Thr Met Ile Ala Thr Asn Ile Gln Thr Pro Phe Phe Thr Pro Ile Lys
        50                  55                  60

Leu Thr Ala Ile Val Ala Ile Phe Ile Ser Val Pro Tyr Leu Leu Tyr
65                  70                  75                  80

Gln Ile Trp Ala Phe Ile Ala Pro Ala Leu Tyr Gln His Glu Lys Arg
                85                  90                  95

Met Ile Tyr Pro Leu Leu Phe Ser Ser Thr Ile Leu Phe Tyr Cys Gly
            100                 105                 110

Val Ala Phe Ala Tyr Tyr Ile Val Phe Pro Leu Val Phe Ser Phe Phe
            115                 120                 125

Thr Gln Thr Ala Pro Glu Gly Val Thr Ile Ala Thr Asp Ile Ser Ser
        130                 135                 140

Tyr Leu Asp Phe Ala Leu Ala Leu Phe Leu Ala Phe Gly Val Cys Phe
145                 150                 155                 160

Glu Val Pro (2) INFORMATION FOR SEQ ID NO:27:

(i) SEQUENCE CHARACTERISTICS:
        (A) LENGTH: 161 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:27:

Leu Glu His Ile Ala Glu Leu Arg Lys Arg Leu Leu Ile Val Ala Leu
1               5                   10                  15

Ala Phe Val Val Phe Phe Ile Ala Gly Phe Phe Leu Ala Lys Pro Ile
            20                  25                  30

Ile Val Tyr Leu Gln Glu Thr Asp Glu Ala Lys Gln Leu Thr Leu Asn
            35                  40                  45
```

```
Ala Phe Asn Leu Thr Asp Pro Leu Tyr Val Phe Met Gln Phe Ala Phe
 50                  55                  60
Ile Ile Gly Ile Val Leu Thr Ser Pro Val Ile Leu Tyr Gln Leu Trp
 65                  70                  75                  80
Ala Phe Val Ser Pro Gly Leu Tyr Glu Lys Glu Arg Lys Val Thr Leu
                     85                  90                  95
Ser Tyr Ile Pro Val Ser Ile Leu Phe Leu Ala Gly Leu Ser Phe
                    100                 105                 110
Ser Tyr Tyr Ile Leu Phe Pro Phe Val Val Asp Phe Met Lys Arg Ile
                    115                 120                 125
Ser Gln Asp Leu Asn Val Asn Gln Val Ile Gly Ile Asn Glu Tyr Phe
                    130                 135                 140
His Phe Leu Leu Gln Leu Thr Ile Pro Phe Gly Leu Leu Phe Gln Met
145                 150                 155                 160
Pro
```

(2) INFORMATION FOR SEQ ID NO:28:

(i) SEQUENCE CHARACTERISTICS:
        (A) LENGTH: 163 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:28:

```
Val Ala His Leu Thr Glu Leu Arg Ser Arg Leu Leu Arg Ser Val Ala
 1               5                  10                  15
Ala Val Leu Leu Ile Phe Ala Ala Leu Phe Tyr Phe Ala Gln Asp Ile
                 20                  25                  30
Tyr Ala Leu Val Ser Ala Pro Leu Arg Ala Tyr Leu Pro Glu Gly Ala
                 35                  40                  45
Thr Met Ile Ala Thr Gly Val Ala Ser Pro Phe Leu Ala Pro Phe Lys
 50                  55                  60
Leu Thr Leu Met Ile Ser Leu Phe Leu Ala Met Pro Val Val Leu His
 65                  70                  75                  80
Gln Val Trp Gly Phe Ile Ala Pro Gly Leu Tyr Gln His Glu Lys Arg
                     85                  90                  95
Ile Ala Met Pro Leu Met Ala Ser Ser Val Leu Leu Phe Tyr Ala Gly
                    100                 105                 110
Met Ala Phe Ala Tyr Phe Val Val Phe Pro Ile Met Phe Gly Phe Phe
                    115                 120                 125
Ala Ser Val Thr Pro Glu Gly Val Ala Met Met Thr Asp Ile Gly Gln
                    130                 135                 140
Tyr Leu Asp Phe Val Leu Thr Leu Phe Phe Ala Phe Gly Val Ala Phe
145                 150                 155                 160
Glu Val Pro
```

(2) INFORMATION FOR SEQ ID NO:29:

(i) SEQUENCE CHARACTERISTICS:
        (A) LENGTH: 204 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:29:

```
Ile Ala Leu Ile Val Ile Val Ser Ser Leu Phe Phe Thr Phe Gly
1               5                   10                  15

Ala Asn Ile Val Val Gly Lys Ile Ile Gly Asp Leu Phe Pro Gly Glu
            20                  25                  30

Ala Val Ile Glu Asn Arg Asp Lys Ile Leu Ala Ile Ala Glu Glu Leu
            35                  40                  45

Lys Lys Ile Ala Ser Asp Leu Glu Asn Tyr Ala Tyr His Pro Ser Glu
    50                  55                  60

Ala Asn Arg Ser Ile Ala Phe Ala Ala Ser Lys Ser Leu Val Arg Ile
65                  70                  75                  80

Ala Met Gln Leu Ser Thr Ser Pro Val Leu Leu Thr Pro Leu Glu Gly
                85                  90                  95

Leu Leu Leu Tyr Leu Lys Ile Ser Leu Ala Val Gly Ile Ala Ala Ala
                100                 105                 110

Leu Pro Tyr Ile Phe His Leu Val Leu Thr Ala Leu Arg Glu Arg Gly
            115                 120                 125

Val Ile Thr Phe Ser Phe Arg Lys Thr Ser Ala Phe Lys Tyr Gly Met
130                 135                 140

Ala Ala Ile Phe Leu Phe Ala Leu Gly Ile Phe Tyr Gly Tyr Asn Met
145                 150                 155                 160

Met Lys Phe Phe Ile Lys Phe Leu Tyr Leu Met Ala Val Ser Gln Gly
                165                 170                 175

Ala Ile Pro Leu Tyr Ser Leu Ser Glu Phe Val Asn Phe Val Ala Leu
            180                 185                 190

Met Leu Val Leu Phe Gly Ile Val Phe Glu Leu Pro
                195                 200
```

(2) INFORMATION FOR SEQ ID NO:30:

(i) SEQUENCE CHARACTERISTICS:
        (A) LENGTH: 136 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:30:

```
Asp Val Glu Asp Leu Arg Arg Leu Ala Ala Glu Glu Gly Val Val Ala
1               5                   10                  15

Leu Gly Glu Thr Gly Leu Asp Tyr Tyr Tyr Thr Pro Glu Thr Lys Val
            20                  25                  30

Arg Gln Gln Glu Ser Phe Ile His His Ile Gln Ile Gly Arg Glu Leu
            35                  40                  45

Asn Lys Pro Val Ile Val His Thr Arg Asp Ala Arg Ala Asp Thr Leu
    50                  55                  60

Ala Ile Leu Arg Glu Glu Lys Val Thr Asp Cys Gly Gly Val Leu His
65                  70                  75                  80

Cys Phe Thr Glu Asp Arg Glu Thr Ala Gly Lys Leu Leu Asp Leu Gly
                85                  90                  95

Phe Tyr Ile Ser Phe Ser Gly Ile Val Thr Phe Arg Asn Ala Glu Gln
                100                 105                 110

Leu Arg Asp Ala Ala Arg Tyr Val Pro Leu Asp Arg Leu Leu Val Glu
            115                 120                 125
```

```
Thr Asp Ser Pro Tyr Leu Ala Pro
    130                 135
```

(2) INFORMATION FOR SEQ ID NO:31:

(i) SEQUENCE CHARACTERISTICS:
        (A) LENGTH: 137 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:31:

```
Ser Leu Glu Gln Leu Gln Gln Ala Leu Glu Arg Arg Pro Ala Lys Val
1               5                   10                  15

Val Ala Val Gly Glu Ile Gly Leu Asp Leu Phe Gly Asp Asp Pro Gln
            20                  25                  30

Phe Glu Arg Gln Gln Trp Leu Leu Asp Glu Gln Leu Lys Leu Ala Lys
        35                  40                  45

Arg Tyr Asp Leu Pro Val Ile Leu His Ser Arg Thr His Asp Lys
    50                  55                  60

Leu Ala Met His Leu Lys Arg His Asp Leu Pro Arg Thr Gly Val Val
65                  70                  75                  80

His Gly Phe Ser Gly Ser Leu Gln Gln Ala Glu Arg Phe Val Gln Leu
                85                  90                  95

Gly Tyr Lys Ile Gly Val Gly Gly Thr Ile Thr Tyr Pro Arg Ala Ser
                100                 105                 110

Lys Thr Arg Asp Val Ile Ala Lys Leu Pro Leu Ala Ser Leu Leu Leu
            115                 120                 125

Glu Thr Asp Ala Pro Asp Met Pro Leu
    130                 135
```

(2) INFORMATION FOR SEQ ID NO:32:

(i) SEQUENCE CHARACTERISTICS:
        (A) LENGTH: 135 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:32:

```
Leu Ile Gly Glu Val Val Ser Gln Ile Glu Ser Asn Ile Asp Leu Ile
1               5                   10                  15

Val Ala Val Gly Glu Thr Gly Met Asp Phe His His Thr Arg Asp Glu
            20                  25                  30

Glu Gly Arg Arg Arg Gln Glu Glu Thr Phe Arg Val Phe Val Glu Leu
        35                  40                  45

Ala Ala Glu His Glu Met Pro Leu Val Val His Ala Arg Asp Ala Glu
    50                  55                  60

Glu Arg Ala Leu Glu Thr Val Leu Glu Tyr Arg Val Pro Glu Val Ile
65                  70                  75                  80

Phe His Cys Tyr Gly Gly Ser Ile Glu Thr Ala Arg Arg Ile Leu Asp
                85                  90                  95

Glu Gly Tyr Tyr Ile Ser Ile Ser Thr Leu Val Ala Phe Ser Glu His
                100                 105                 110

His Met Glu Leu Val Arg Ala Ile Pro Leu Glu Gly Met Leu Thr Glu
            115                 120                 125
```

```
Thr Asp Ser Pro Tyr Leu Ser
    130                 135
```

(2) INFORMATION FOR SEQ ID NO:33:

(i) SEQUENCE CHARACTERISTICS:
        (A) LENGTH: 142 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:33:

```
Ala Gln Ala Thr Leu Lys Lys Leu Val Ser Thr His Arg Ser Phe Ile
1               5                   10                  15

Ser Cys Ile Gly Glu Tyr Gly Phe Asp Tyr His Tyr Thr Lys Asp Tyr
                20                  25                  30

Ile Thr Gln Gln Glu Gln Phe Phe Leu Met Gln Phe Gln Leu Ala Glu
            35                  40                  45

Gln Tyr Gln Leu Val His Met Leu His Val Arg Asp Val His Glu Arg
    50                  55                  60

Ile Tyr Glu Val Leu Lys Arg Leu Lys Pro Lys Gln Pro Val Val Phe
65                  70                  75                  80

His Cys Phe Ser Glu Asp Thr Asn Thr Ala Leu Lys Leu Leu Thr Leu
                85                  90                  95

Arg Glu Val Gly Leu Lys Val Tyr Phe Ser Ile Pro Gly Ile Val Thr
            100                 105                 110

Phe Lys Asn Ala Lys Asn Leu Gln Ala Ala Leu Ser Val Ile Pro Thr
        115                 120                 125

Glu Leu Leu Leu Ser Glu Thr Asp Ser Pro Tyr Leu Ala Pro
    130                 135                 140
```

(2) INFORMATION FOR SEQ ID NO:34:

(i) SEQUENCE CHARACTERISTICS:
        (A) LENGTH: 140 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:34:

```
Ala Arg Ala Glu Leu Glu Arg Leu Val Ala His Pro Arg Val Val Ala
1               5                   10                  15

Val Gly Glu Thr Gly Ile Asp Met Tyr Trp Pro Gly Arg Leu Asp Gly
                20                  25                  30

Cys Ala Glu Pro His Val Gln Arg Glu Ala Phe Ala Trp His Ile Asp
            35                  40                  45

Leu Ala Lys Arg Thr Gly Lys Pro Leu Met Ile His Asn Arg Gln Ala
    50                  55                  60

Asp Arg Asp Val Leu Asp Val Leu Arg Ala Glu Gly Ala Pro Asp Thr
65                  70                  75                  80

Val Ile Leu His Cys Phe Ser Ser Asp Ala Ala Met Ala Arg Thr Cys
                85                  90                  95

Val Asp Ala Gly Trp Leu Leu Ser Leu Ser Gly Thr Val Ser Phe Arg
            100                 105                 110

Thr Ala Arg Glu Leu Arg Glu Ala Val Pro Leu Met Pro Val Glu Gln
```

```
                115                 120                 125
Leu Leu Val Glu Thr Asp Ala Pro Tyr Leu Thr Pro
    130                 135                 140

(2) INFORMATION FOR SEQ ID NO:35:

(i) SEQUENCE CHARACTERISTICS:
        (A) LENGTH: 138 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:35:

Asp Glu Ser Leu Phe Glu Lys Phe Val Gly His Gln Lys Cys Val Ala
1               5                   10                  15

Ile Gly Glu Cys Gly Leu Asp Tyr Tyr Arg Leu Pro Glu Leu Asn Glu
            20                  25                  30

Arg Glu Asn Tyr Lys Ser Lys Gln Lys Glu Ile Phe Thr Lys Gln Ile
        35                  40                  45

Glu Phe Ser Ile Gln His Asn Lys Pro Leu Ile Ile His Ile Arg Glu
    50                  55                  60

Ala Ser Phe Asp Ser Leu Asn Leu Leu Lys Asn Tyr Pro Lys Ala Phe
65                  70                  75                  80

Gly Val Leu His Cys Phe Asn Ala Asp Gly Met Leu Leu Glu Leu Ser
                85                  90                  95

Asp Arg Phe Tyr Tyr Gly Ile Gly Gly Val Ser Thr Phe Lys Asn Ala
            100                 105                 110

Lys Arg Leu Val Glu Ile Leu Pro Lys Ile Pro Lys Asn Arg Leu Leu
        115                 120                 125

Leu Glu Thr Asp Ser Pro Tyr Leu Thr Pro
    130                 135

(2) INFORMATION FOR SEQ ID NO:36:

(i) SEQUENCE CHARACTERISTICS:
        (A) LENGTH: 136 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:36:

Asp Ala Glu Arg Leu Leu Arg Leu Ala Gln Asp Pro Lys Val Ile Ala
1               5                   10                  15

Ile Gly Glu Ile Gly Leu Asp Tyr Tyr Tyr Ser Ala Asp Asn Lys Ala
            20                  25                  30

Ala Gln Gln Ala Val Phe Gly Ser Gln Ile Asp Ile Ala Asn Gln Leu
        35                  40                  45

Asp Lys Pro Val Ile Ile His Thr Arg Ser Ala Gly Asp Asp Thr Ile
    50                  55                  60

Ala Met Leu Arg Gln His Arg Ala Glu Lys Cys Gly Gly Val Ile His
65                  70                  75                  80

Cys Phe Thr Glu Thr Met Glu Phe Xaa Lys Lys Ala Leu Asp Leu Gly
                85                  90                  95

Phe Tyr Ile Ser Cys Ser Gly Ile Val Thr Phe Lys Asn Ala Glu Ala
            100                 105                 110
```

```
Ile Arg Glu Val Ile Arg Tyr Val Pro Met Glu Arg Leu Leu Val Glu
        115                 120                 125

Thr Asp Ser Pro Tyr Leu Ala Pro
        130                 135

(2) INFORMATION FOR SEQ ID NO:37:

(i) SEQUENCE CHARACTERISTICS:
        (A) LENGTH: 136 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:37:

Asp Leu Ala Trp Ile Lys Glu Leu Ser Ala His Glu Lys Val Val Ala
1               5                   10                  15

Ile Gly Glu Met Gly Leu Asp Tyr His Trp Asp Lys Ser Pro Lys Asp
            20                  25                  30

Ile Gln Lys Glu Val Phe Arg Asn Gln Ile Ala Leu Ala Lys Glu Val
        35                  40                  45

Asn Leu Pro Ile Ile Ile His Asn Arg Asp Ala Thr Glu Asp Val Val
50                  55                  60

Thr Ile Leu Lys Glu Glu Gly Ala Glu Ala Val Gly Gly Ile Met His
65                  70                  75                  80

Cys Phe Thr Gly Ser Ala Glu Val Ala Arg Glu Cys Met Lys Met Asn
                85                  90                  95

Phe Tyr Leu Ser Phe Gly Gly Pro Val Thr Phe Lys Asn Ala Lys Lys
            100                 105                 110

Pro Lys Glu Val Val Lys Glu Ile Pro Asn Asp Arg Leu Leu Ile Glu
        115                 120                 125

Thr Asp Cys Pro Phe Leu Thr Pro
        130                 135

(2) INFORMATION FOR SEQ ID NO:38:

(i) SEQUENCE CHARACTERISTICS:
        (A) LENGTH: 135 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:38:

Glu Ala Leu Ala Asn Lys Gly Lys Ala Ser Gly Lys Val Val Ala Phe
1               5                   10                  15

Gly Glu Phe Gly Leu Asp Tyr Asp Arg Leu His Tyr Ala Pro Ala Asp
            20                  25                  30

Val Gln Lys Met Tyr Phe Glu Glu Gln Leu Lys Val Ala Val Arg Val
        35                  40                  45

Gln Leu Pro Leu Phe Leu His Ser Arg Asn Ala Glu Asn Asp Phe Phe
50                  55                  60

Ala Ile Leu Glu Lys Tyr Leu Pro Glu Leu Pro Lys Lys Gly Val Val
65                  70                  75                  80

His Ser Phe Thr Gly Ser Ile Asp Glu Met Arg Arg Cys Ile Glu His
                85                  90                  95

Gly Leu Tyr Val Gly Val Asn Gly Cys Ser Leu Lys Thr Glu Glu Asn
            100                 105                 110
```

```
Leu Glu Val Val Arg Ala Ile Pro Leu Glu Lys Met Leu Leu Glu Thr
        115                 120                 125

Asp Ala Pro Trp Cys Glu Val
        130             135

(2) INFORMATION FOR SEQ ID NO:39:

(i) SEQUENCE CHARACTERISTICS:
        (A) LENGTH: 149 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:39:

His Ile Ser Lys Met Glu Gln Phe Phe Val Glu His Glu Arg Asp Ile
1               5                   10                  15

Ile Cys Val Gly Glu Cys Gly Leu Asp His Thr Ile Ser Gln Phe Lys
            20                  25                  30

Leu Thr Thr Glu Asp Phe Glu Glu Gln Glu Thr Val Phe Lys Trp Gln
        35                  40                  45

Ile Asp Leu Ala Lys His Phe Glu Lys Pro Leu Ile Leu Glu Ile Pro
    50                  55                  60

Asp Ile Ser Arg Asn Val His Ser Arg Ser Ala Ala Arg Arg Thr Ile
65                  70                  75                  80

Glu Ile Leu Leu Glu Cys His Val Ala Pro Asp Gln Val Val Leu His
                85                  90                  95

Ala Phe Asp Gly Thr Pro Gly Asp Leu Lys Leu Gly Leu Glu Ala Gly
            100                 105                 110

Tyr Leu Phe Ser Ile Pro Pro Ser Phe Gly Lys Ser Glu Glu Thr Thr
        115                 120                 125

Gln Leu Ile Glu Ser Ile Pro Leu Ser Gln Leu Leu Leu Glu Thr Asp
    130                 135                 140

Ser Pro Ala Leu Gly
145

(2) INFORMATION FOR SEQ ID NO:40:

(i) SEQUENCE CHARACTERISTICS:
        (A) LENGTH: 139 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:40:

Gln Glu Arg Asn Leu Leu Gln Ala Leu Arg His Pro Lys Ala Val Ala
1               5                   10                  15

Phe Gly Glu Met Gly Leu Asp Tyr Ser Tyr Lys Cys Thr Thr Pro Val
            20                  25                  30

Pro Glu Gln His Lys Val Phe Glu Arg Gln Leu Gln Leu Ala Val Ser
        35                  40                  45

Leu Lys Lys Pro Leu Val Ile His Cys Arg Glu Ala Asp Glu Asp Leu
    50                  55                  60

Leu Glu Ile Met Lys Lys Phe Val Pro Pro Asp Tyr Lys Ile His Arg
65                  70                  75                  80

His Cys Phe Thr Gly Ser Tyr Pro Val Ile Glu Pro Leu Leu Lys Tyr
```

```
                        85                  90                  95
Phe Pro Asn Met Ser Val Gly Phe Thr Ala Val Leu Thr Tyr Ser Ser
            100                 105                 110
Ala Trp Glu Ala Arg Glu Ala Leu Arg Gln Ile Pro Leu Glu Arg Ile
        115                 120                 125
Ile Val Glu Thr Asp Ala Pro Tyr Phe Leu Pro
        130                 135
```

(2) INFORMATION FOR SEQ ID NO:41:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:41:

```
Ser Arg Arg Ser Phe Leu Lys
1               5
```

(2) INFORMATION FOR SEQ ID NO:42:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:42:

```
Thr Arg Arg Ser Phe Leu Lys
1               5
```

(2) INFORMATION FOR SEQ ID NO:43:

(i) SEQUENCE CHARACTERISTICS:
        (A) LENGTH: 50 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:43:

```
Met Lys Thr Lys Ile Pro Asp Ala Val Leu Ala Ala Glu Val Ser Arg
1               5                   10                  15
Arg Gly Leu Val Lys Thr Thr Ile Ala Phe Phe Leu Ala Met Ala Ser
            20                  25                  30
Ser Ala Leu Thr Leu Pro Phe Ser Arg Ile Ala His Ala Val Asp Ser
        35                  40                  45
Ala Ile
    50
```

(2) INFORMATION FOR SEQ ID NO:44:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:44:

TTAGTCGGAT TAATCACAAT GTCGATAGCG                                           30

(2) INFORMATION FOR SEQ ID NO:45:

(i) SEQUENCE CHARACTERISTICS:
        (A) LENGTH: 3120 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:45:

```
ATTCTGGCTG GGTGCCACCA GATACCAACG TTGAAGAGTT CGAATTTGCC ATTCGTACGG    60
TCTGTGAACC TATCTTTGAG AAACCGCTGG CCGAAATTTC GTTTGGACAT GTACTGTTAA   120
ATCTGTTTAA TACGGCGCGT CGCTTCAATA TGGAAGTGCA GCCGCAACTG GTGTTACTCC   180
AGAAAACCCT GCTCTACGTC GAAGGGGTAG GACGCCAGCT TTATCCGCAA CTCGATTTAT   240
GGAAAACGGC GAAGCCTTTC CTGGAGTCGT GGATTAAAGA TCAGGTCGGT ATTCCTGCGC   300
TGGTGAGAGC ATTTAAAGAA AAAGCGCCGT TCTGGGTCGA AAAAATGCCA GAACTGCCTG   360
AATTGGTTTA CGACAGTTTG CGCCAGGGCA AGTATTTACA GCACAGTGTT GATAAGATTG   420
CCCGCGAGCT TCAGTCAAAT CATGTACGTC AGGGACAATC GCGTTATTTT CTCGGAATTG   480
GCGCTACGTT AGTATTAAGT GGCACATTCT TGTTGGTCAG CCGACCTGAA TGGGGCTGA    540
TGCCCGGCTG GTTAATGGCA GGTGGTCTGA TCGCCTGGTT TGTCGGTTGG CGCAAAACAC   600
GCTGATTTTT TCATCGCTCA AGGCGGGCCG TGTAACGTAT AATGCGGCTT TGTTTAATCA   660
TCATCTACCA CAGAGGAACA TGTATGGGTG GTATCAGTAT TTGGCAGTTA TTGATTATTG   720
CCGTCATCGT TGTACTGCTT TTTGGCACCA AAAAGCTCGG CTCCATCGGT TCCGATCTTG   780
GTGCGTCGAT CAAAGGCTTT AAAAAAGCAA TGAGCGATGA TGAACCAAAG CAGGATAAAA   840
CCAGTCAGGA TGCTGATTTT ACTGCGAAAA CTATCGCCGA TAAGCAGGCG GATACGAATC   900
AGGAACAGGC TAAAACAGAA GACGCGAAGC GCCACGATAA AGAGCAGGTG TAATCCGTGT   960
TTGATATCGG TTTTAGCGAA CTGCTATTGG TGTTCATCAT CGGCCTCGTC GTTCGGGGC   1020
CGCAACGACT GCCTGTGGCG GTAAAAACGG TAGCGGGCTG GATTCGCGCG TTGCGTTCAC  1080
TGGCGACAAC GGTGCAGAAC GAACTGACCC AGGAGTTAAA ACTCCAGGAG TTTCAGGACA  1140
GTCTGAAAAA GGTTGAAAAG GCGAGCCTCA CTAACCTGAC GCCCGAACTG AAAGCGTCGA  1200
TGGATGAACT ACGCCAGGCC GCGGAGTCGA TGAAGCGTTC CTACGTTGCA AACGATCCTG  1260
AAAAGGCGAG CGATGAAGCG CACACCATCC ATAACCCGGT GGTGAAAGAT AATGAAGCTG  1320
CGCATGAGGG CGTAACGCCT GCCGCTGCAC AAACGCAGGC CAGTTCGCCG GAACAGAAGC  1380
CAGAAACCAC GCCAGAGCCG GTGGTAAAAC CTGCTGCGGA CGCTGAACCG AAAACCGCTG  1440
CACCTTCCCC TTCGTCGAGT GATAAACCGT AAACATGTCT GTAGAAGATA CTCAACCGCT  1500
TATCACGCAT CTGATTGAGC TGCGTAAGCG TCTGCTGAAC TGCATTATCG CGGTGATCGT  1560
GATATTCCTG TGTCTGGTCT ATTTCGCCAA TGACATCTAT CACCTGGTAT CCGCGCCATT  1620
GATCAAGCAG TTGCCGCAAG GTTCAACGAT GATCGCCACC GACGTGGCCT CGCCGTTCTT  1680
TACGCCGATC AAGCTGACCT TTATGGTGTC GCTGATTCTG TCAGCGCCGG TGATTCTCTA  1740
TCAGGTGTGG GCATTTATCG CCCCAGCGCT GTATAAGCAT GAACGTCGCC TGGTGGTGCC  1800
GCTGCTGGTT TCCAGCTCTC TGCTGTTTTA TATCGGCATG GCATTCGCCT ACTTTGTGGT  1860
```

```
CTTTCCGCTG GCATTTGGCT TCCTTGCCAA TACCGCGCCG GAAGGGGTGC AGGTATCCAC        1920

CGACATCGCC AGCTATTTAA GCTTCGTTAT GGCGCTGTTT ATGGCGTTTG GTGTCTCCTT        1980

TGAAGTGCCG GTAGCAATTG TGCTGCTGTG CTGGATGGGG ATTACCTCGC CAGAAGACTT        2040

ACGCAAAAAA CGCCCGTATG TGCTGGTTGG TGCATTCGTT GTCGGGATGT TGCTGACGCC        2100

GCCGGATGTC TTCTCGCAAA CGCTGTTGGC GATCCCGATG TACTGTCTGT TTGAAATCGG        2160

TGTCTTCTTC TCACGCTTTT ACGTTGGTAA AGGGCGAAAT CGGGAAGAGG AAAACGACGC        2220

TGAAGCAGAA AGCGAAAAAA CTGAAGAATA AATTCAACCG CCCGTCAGGG CGGTTGTCAT        2280

ATGGAGTACA GGATGTTTGA TATCGGCGTT AATTTGACCA GTTCGCAATT TGCGAAAGAC        2340

CGTGATGATG TTGTAGCGTG CGCTTTTGAC GCGGGAGTTA ATGGGCTACT CATCACCGGC        2400

ACTAACCTGC GTGAAAGCCA GCAGGCGCAA AAGCTGGCGC GTCAGTATTC GTCCTGTTGG        2460

TCAACGGCGG GCGTACATCC TCACGACAGC AGCCAGTGGC AAGCTGCGAC TGAAGAAGCG        2520

ATTATTGAGC TGGCCGCGCA GCCAGAAGTG GTGGCGATTG GTGAATGTGG TCTCGACTTT        2580

AACCGCAACT TTTCGACGCC GGAAGAGCAG GAACGCGCTT TTGTTGCCCA GCTACGCATT        2640

GCCGCAGATT TAAACATGCC GGTATTTATG CACTGTCGCG ATGCCCACGA GCGGTTTATG        2700

ACATTGCTGG AGCCGTGGCT GGATAAACTG CCTGGTGCGG TTCTTCATTG CTTTACCGGC        2760

ACACGCGAAG AGATGCAGGC GTGCGTGGCG CATGGAATTT ATATCGGCAT TACCGGTTGG        2820

GTTTGCGATG AACGACGCGG ACTGGAGCTG CGGGAACTTT TGCCGTTGAT TCCGGCGGAA        2880

AAATTACTGA TCGAAACTGA TGCGCCGTAT CTGCTCCCTC GCGATCTCAC GCCAAAGCCA        2940

TCATCCCGGC GCAACGAGCC AGCCCATCTG CCCCATATTT TGCAACGTAT TGCGCACTGG        3000

CGTGGAGAAG ATGCCGCATG GCTGGCTGCC ACCACGGATG CTAATGCCAA AACACTGTTT        3060

GGGATTGCGT TTAGAGTTT GCGGAACTCG GTATTCTTCA CACTGTGCTT AATCTCTTTA        3120
```

(2) INFORMATION FOR SEQ ID NO:46:

(i) SEQUENCE CHARACTERISTICS:
        (A) LENGTH: 312 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:46:

```
ATGCGGCTTT GTTTAATCAT CATCTACCAC AGAGGAACAT GTATGGGTGG TATCAGTATT         60

TGGCAGTTAT TGATTATTGC CGTCATCGTT GTACTGCTTT TTGGCACCAA AAAGCTCGGC        120

TCCATCGGTT CCGATCTTGG TGCGTCGATC AAAGGCTTTA AAAAAGCAAT GAGCGATGAT        180

GAACCAAAGC AGGATAAAAC CAGTCAGGAT GCTGATTTTA CTGCGAAAAC TATCGCCGAT        240

AAGCAGGCGG ATACGAATCA GGAACAGGCT AAAACAGAAG ACGCGAAGCG CCACGATAAA        300

GAGCAGGTGT AA                                                             312
```

(2) INFORMATION FOR SEQ ID NO:47:

(i) SEQUENCE CHARACTERISTICS:
        (A) LENGTH: 103 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:47:

```
Met Arg Leu Cys Leu Ile Ile Ile Tyr His Arg Gly Thr Cys Met Gly
1               5                   10                  15

Gly Ile Ser Ile Trp Gln Leu Leu Ile Ile Ala Val Ile Val Val Leu
                20                  25                  30

Leu Phe Gly Thr Lys Lys Leu Gly Ser Ile Gly Ser Asp Leu Gly Ala
            35                  40                  45

Ser Ile Lys Gly Phe Lys Lys Ala Met Ser Asp Asp Glu Pro Lys Gln
    50                  55                  60

Asp Lys Thr Ser Gln Asp Ala Asp Phe Thr Ala Lys Thr Ile Ala Asp
65                  70                  75                  80

Lys Gln Ala Asp Thr Asn Gln Glu Gln Ala Lys Thr Glu Asp Ala Lys
                85                  90                  95

Arg His Asp Lys Glu Gln Val
            100
```

(2) INFORMATION FOR SEQ ID NO:48:

(i) SEQUENCE CHARACTERISTICS:
        (A) LENGTH: 515 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:48:

```
TGTTTGATAT CGGTTTTAGC GAACTGCTAT TGGTGTTCAT CATCGGCCTC GTCGTTCTGG      60

GGCCGCAACG ACTGCCTGTG GCGGTAAAAA CGGTAGCGGG CTGGATTCGC GCGTTGCGTT     120

CACTGGCGAC AACGGTGCAG AACGAACTGA CCCAGGAGTT AAAACTCCAG GAGTTTCAGG     180

ACAGTCTGAA AAAGGTTGAA AAGGCGAGCC TCACTAACCT GACGCCCGAA CTGAAAGCGT     240

CGATGGATGA ACTACGCCAG GCCGCGGAGT CGATGAAGCG TTCCTACGTT GCAAACGATC     300

CTGAAAAGGC GAGCGATGAA GCGCACACCA TCCATAACCC GGTGGTGAAA GATAATGAAG     360

CTGCGCATGA GGGCGTAACG CCTGCCGCTG CACAAACGCA GGCCAGTTCG CCGGAACAGA     420

AGCCAGAAAC CACGCCAGAG CCGGTGGTAA AACCTGCTGC GGACGCTGAA CCGAAAACCG     480

CTGCACCTTC CCCTTCGTCG AGTGATAAAC CGTAA                                515
```

(2) INFORMATION FOR SEQ ID NO:49:

(i) SEQUENCE CHARACTERISTICS:
        (A) LENGTH: 161 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:49:

```
Val Phe Asp Ile Gly Phe Ser Glu Leu Leu Leu Val Phe Ile Ile Gly
1               5                   10                  15

Leu Val Val Leu Gly Pro Gln Arg Leu Pro Val Ala Val Lys Thr Val
                20                  25                  30

Ala Gly Trp Ile Arg Ala Leu Arg Ser Leu Ala Thr Thr Val Gln Asn
            35                  40                  45

Glu Leu Thr Gln Glu Leu Lys Leu Gln Glu Phe Gln Asp Ser Leu Lys
    50                  55                  60
```

```
Lys Val Glu Lys Ala Ser Leu Thr Asn Leu Thr Pro Glu Leu Lys Ala
 65                  70                  75                  80

Ser Met Asp Glu Leu Arg Gln Ala Ala Glu Ser Met Lys Arg Ser Tyr
                 85                  90                  95

Val Ala Asn Asp Pro Glu Lys Ala Ser Asp Glu Ala His Thr Ile His
                100                 105                 110

Asn Pro Val Val Lys Asp Asn Gly Ala Ala His Glu Gly Val Thr Pro
                115                 120                 125

Ala Ala Ala Gln Thr Gln Ala Ser Ser Pro Glu Gln Lys Pro Glu Thr
                130                 135                 140

Thr Pro Glu Pro Val Val Lys Pro Ala Ala Asp Ala Glu Pro Lys Thr
145                 150                 155                 160

Ala
```

(2) INFORMATION FOR SEQ ID NO:50:

(i) SEQUENCE CHARACTERISTICS:
        (A) LENGTH: 46 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:50:

```
Met Glu Ala Arg Met Thr Gly Arg Arg Lys Val Thr Arg Arg Asp Ala
 1               5                  10                  15

Met Ala Asp Ala Ala Arg Ala Val Gly Val Ala Cys Leu Gly Gly Phe
                20                  25                  30

Ser Leu Ala Ala Leu Val Arg Thr Ala Ser Pro Val Asp Ala
                35                  40                  45
```

(2) INFORMATION FOR SEQ ID NO:51:

(i) SEQUENCE CHARACTERISTICS:
        (A) LENGTH: 41 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:51:

```
Met Ser Arg Ser Ala Lys Pro Gln Asn Gly Arg Arg Arg Phe Leu Arg
 1               5                  10                  15

Asp Val Val Arg Thr Ala Gly Gly Leu Ala Ala Val Gly Val Ala Leu
                20                  25                  30

Gly Leu Gln Gln Gln Thr Ala Arg Ala
                35                  40
```

(2) INFORMATION FOR SEQ ID NO:52:

(i) SEQUENCE CHARACTERISTICS:
        (A) LENGTH: 27 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:52:

```
Met Thr Trp Ser Arg Arg Gln Phe Leu Thr Gly Val Gly Val Leu Ala
 1               5                  10                  15
```

Ala Val Ser Gly Thr Ala Gly Arg Val Val Ala
            20                  25

(2) INFORMATION FOR SEQ ID NO:53:

(i) SEQUENCE CHARACTERISTICS:
        (A) LENGTH: 27 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:53:

Met Asp Arg Arg Arg Phe Leu Thr Leu Leu Gly Ser Ala Gly Leu Thr
1               5                   10                  15

Ala Thr Val Ala Thr Ala Gly Thr Ala Lys Ala
            20                  25

(2) INFORMATION FOR SEQ ID NO:54:

(i) SEQUENCE CHARACTERISTICS:
        (A) LENGTH: 37 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:54:

Met Ser Glu Lys Asp Lys Met Ile Thr Arg Arg Asp Ala Leu Arg Asn
1               5                   10                  15

Ile Ala Val Val Val Gly Ser Val Ala Thr Thr Thr Met Met Gly Val
            20                  25                  30

Gly Val Ala Asp Ala
        35

(2) INFORMATION FOR SEQ ID NO:55:

(i) SEQUENCE CHARACTERISTICS:
        (A) LENGTH: 34 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:55:

Met Gln Ile Val Asn Leu Thr Arg Arg Gly Phe Leu Lys Ala Ala Cys
1               5                   10                  15

Val Val Thr Gly Gly Ala Leu Ile Ser Ile Arg Met Thr Gly Lys Ala
            20                  25                  30

Val Ala (2) INFORMATION FOR SEQ ID NO:56:

(i) SEQUENCE CHARACTERISTICS:
        (A) LENGTH: 45 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:56:

```
Met Asn Glu Glu Thr Phe Tyr Gln Ala Met Arg Arg Gln Gly Val
1               5                  10                 15

Thr Arg Arg Ser Phe Leu Lys Tyr Cys Ser Leu Ala Ala Thr Ser Leu
                20                  25                  30

Gly Leu Gly Ala Gly Met Ala Pro Lys Ile Ala Trp Ala
            35              40                  45
```

(2) INFORMATION FOR SEQ ID NO:57:

(i) SEQUENCE CHARACTERISTICS:
        (A) LENGTH: 48 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:57:

```
Met Ser Thr Gly Thr Thr Asn Leu Val Arg Thr Leu Asp Ser Met Asp
1               5                  10                  15

Phe Leu Lys Met Asp Arg Arg Thr Phe Met Lys Ala Val Ser Ala Leu
                20                  25                  30

Gly Ala Thr Ala Phe Leu Gly Thr Tyr Gln Thr Glu Ile Val Asn Ala
            35                  40                  45
```

(2) INFORMATION FOR SEQ ID NO:58:

(i) SEQUENCE CHARACTERISTICS:
        (A) LENGTH: 50 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:58:

```
Met Lys Cys Tyr Ile Gly Arg Gly Lys Asn Gln Val Glu Glu Arg Leu
1               5                  10                  15

Glu Arg Arg Gly Val Ser Arg Arg Asp Phe Met Lys Phe Cys Thr Ala
                20                  25                  30

Val Ala Val Ala Met Gly Met Gly Pro Ala Phe Ala Pro Lys Val Ala
            35                  40                  45

Glu Ala
    50
```

(2) INFORMATION FOR SEQ ID NO:59:

(i) SEQUENCE CHARACTERISTICS:
        (A) LENGTH: 26 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:59:

```
Met Asn Arg Arg Asn Phe Ile Lys Ala Ala Ser Cys Gly Ala Leu Leu
1               5                  10                  15

Thr Gly Ala Leu Pro Ser Val Ser His Ala
                20                  25
```

(2) INFORMATION FOR SEQ ID NO:60:

(i) SEQUENCE CHARACTERISTICS:

(A) LENGTH: 44 amino acids
(B) TYPE: amino acid
(C) STRANDEDNESS: Not Relevant
(D) TOPOLOGY: unknown (ii) MOLECULE TYPE: protein (xi) SEQUENCE DESCRIPTION: SEQ ID NO:60:

Met Ser His Ala Asp Glu His Ala Gly Asp His Gly Ala Thr Arg Arg
1               5                   10                  15

Asp Phe Leu Tyr Tyr Ala Thr Ala Gly Ala Gly Thr Val Ala Ala Gly
                20                  25                  30

Ala Ala Ala Trp Thr Leu Val Asn Gln Met Asn Pro
            35                  40

(2) INFORMATION FOR SEQ ID NO:61:

(i) SEQUENCE CHARACTERISTICS:
        (A) LENGTH: 44 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:61:

Met Thr Gln Ile Ser Gly Ser Pro Asp Val Pro Asp Leu Gly Arg Arg
1               5                   10                  15

Gln Phe Met Asn Leu Leu Thr Phe Gly Thr Ile Thr Gly Val Ala Ala
                20                  25                  30

Gly Ala Leu Tyr Pro Ala Val Lys Tyr Leu Ile Pro
            35                  40

(2) INFORMATION FOR SEQ ID NO:62:

(i) SEQUENCE CHARACTERISTICS:
        (A) LENGTH: 32 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:62:

Met Asp Arg Arg Thr Phe Leu Arg Leu Tyr Leu Leu Val Gly Ala Ala
1               5                   10                  15

Ile Ala Val Ala Pro Val Ile Lys Pro Ala Leu Asp Tyr Val Gly Tyr
                20                  25                  30

(2) INFORMATION FOR SEQ ID NO:63:

(i) SEQUENCE CHARACTERISTICS:
        (A) LENGTH: 42 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:63:

Met Thr Lys Leu Ser Gly Gln Glu Leu His Ala Glu Leu Ser Arg Arg
1               5                   10                  15

Ala Phe Leu Ser Tyr Thr Ala Ala Val Gly Ala Leu Gly Leu Cys Gly
                20                  25                  30

Thr Ser Leu Leu Ala Gln Gly Ala Arg Ala 35                  40

(2) INFORMATION FOR SEQ ID NO:64:

(i) SEQUENCE CHARACTERISTICS:
        (A) LENGTH: 31 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:64:

Met Thr Leu Thr Arg Arg Glu Phe Ile Lys His Ser Gly Ile Ala Ala
1               5                   10                  15

Gly Ala Leu Val Val Thr Ser Ala Ala Pro Leu Pro Ala Trp Ala
            20                  25                  30

(2) INFORMATION FOR SEQ ID NO:65:

(i) SEQUENCE CHARACTERISTICS:
        (A) LENGTH: 31 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:65:

Met Thr Ile Ser Arg Arg Asp Leu Leu Lys Ala Gln Ala Ala Gly Ile
1               5                   10                  15

Ala Ala Met Ala Ala Asn Ile Pro Leu Ser Ser Gln Ala Pro Ala
            20                  25                  30

(2) INFORMATION FOR SEQ ID NO:66:

(i) SEQUENCE CHARACTERISTICS:
        (A) LENGTH: 32 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:66:

Met Ser Glu Ala Leu Ser Gly Arg Gly Asn Asp Arg Arg Lys Phe Leu
1               5                   10                  15

Lys Met Ser Ala Leu Ala Gly Val Ala Gly Val Ser Gln Ala Val Gly
            20                  25                  30

(2) INFORMATION FOR SEQ ID NO:67:

(i) SEQUENCE CHARACTERISTICS:
        (A) LENGTH: 45 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:67:

Met Lys Thr Lys Ile Pro Asp Ala Val Leu Ala Ala Glu Val Ser Arg
1               5                   10                  15

Arg Gly Leu Val Lys Thr Thr Ala Ile Gly Gly Leu Ala Met Ala Ser
            20                  25                  30

Ser Ala Leu Thr Leu Pro Phe Ser Arg Ile Ala His Ala 35        40        45

(2) INFORMATION FOR SEQ ID NO:68:

(i) SEQUENCE CHARACTERISTICS:
        (A) LENGTH: 35 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:68:

Met Ser Asn Phe Asn Gln Ile Ser Arg Arg Asp Phe Val Lys Ala Ser
1               5                   10                  15

Ser Ala Gly Ala Ala Leu Ala Val Ser Asn Leu Thr Leu Pro Phe Asn
            20                  25                  30

Val Met Ala
        35

(2) INFORMATION FOR SEQ ID NO:69:

(i) SEQUENCE CHARACTERISTICS:
        (A) LENGTH: 30 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:69:

Met Ser Ile Ser Arg Arg Ser Phe Leu Gln Gly Val Gly Ile Gly Cys
1               5                   10                  15

Ser Ala Cys Ala Leu Gly Ala Phe Pro Pro Gly Ala Leu Ala
            20                  25                  30

(2) INFORMATION FOR SEQ ID NO:70:

(i) SEQUENCE CHARACTERISTICS:
        (A) LENGTH: 37 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:70:

Met Lys Thr Val Leu Pro Ser Val Pro Glu Thr Val Arg Leu Ser Arg
1               5                   10                  15

Arg Gly Phe Leu Val Gln Ala Gly Thr Ile Thr Cys Ser Val Ala Phe
            20                  25                  30

Gly Ser Val Pro Ala
        35

(2) INFORMATION FOR SEQ ID NO:71:

(i) SEQUENCE CHARACTERISTICS:
        (A) LENGTH: 44 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:71:

Met Gly Arg Leu Asn Arg Phe Arg Leu Gly Lys Asp Gly Arg Arg Glu

-continued

```
1               5               10              15

Gln Ala Ser Leu Ser Arg Arg Gly Phe Leu Val Thr Ser Leu Gly Ala
                20              25              30

Gly Val Met Phe Gly Phe Ala Arg Pro Ser Ser Ala
        35              40
```

(2) INFORMATION FOR SEQ ID NO:72:

(i) SEQUENCE CHARACTERISTICS:
        (A) LENGTH: 50 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:72:

```
Met Ser Asp Lys Asp Ser Lys Asn Thr Pro Gln Val Pro Glu Lys Leu
1               5               10              15

Gly Leu Ser Arg Arg Gly Phe Leu Gly Ala Ser Ala Val Thr Gly Ala
                20              25              30

Ala Val Ala Ala Thr Ala Leu Gly Gly Ala Val Met Thr Arg Glu Ser
        35              40              45

Trp Ala
    50
```

(2) INFORMATION FOR SEQ ID NO:73:

(i) SEQUENCE CHARACTERISTICS:
        (A) LENGTH: 32 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:73:

```
Met Glu Ser Arg Thr Ser Arg Arg Thr Phe Val Lys Gly Leu Ala Ala
1               5               10              15

Ala Gly Val Leu Gly Gly Leu Gly Leu Trp Arg Ser Pro Ser Trp Ala
                20              25              30
```

(2) INFORMATION FOR SEQ ID NO:74:

(i) SEQUENCE CHARACTERISTICS:
        (A) LENGTH: 27 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:74:

```
Met Ser Leu Ser Arg Arg Gln Phe Ile Gln Ala Ser Gly Ile Ala Leu
1               5               10              15

Cys Ala Gly Ala Val Pro Leu Lys Ala Ser Ala
                20              25
```

(2) INFORMATION FOR SEQ ID NO:75:

(i) SEQUENCE CHARACTERISTICS:
        (A) LENGTH: 57 amino acids
        (B) TYPE: amino acid
        (C) STRANDEDNESS: Not Relevant
        (D) TOPOLOGY: unknown -continued (ii) MOLECULE TYPE: protein (xi) SEQUENCE DESCRIPTION: SEQ ID NO:75:

Met Leu Gly Lys Ser Gln Phe Asp Asp Leu Phe Glu Lys Met Ser Arg
1               5                   10                  15

Lys Val Ala Gly His Thr Ser Arg Arg Gly Phe Ile Gly Arg Val Gly
                20                  25                  30

Thr Ala Val Ala Gly Val Ala Leu Val Pro Leu Leu Pro Val Asp Arg
            35                  40                  45

Arg Gly Arg Val Ser Arg Ala Asn Ala
    50                  55

(2) INFORMATION FOR SEQ ID NO:76:

(i) SEQUENCE CHARACTERISTICS:
        (A) LENGTH: 30 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:76:

Met Thr Leu Asn Arg Arg Asp Phe Ile Lys Thr Ser Gly Ala Ala Val
1               5                   10                  15

Ala Ala Val Gly Ile Leu Gly Phe Pro His Leu Ala Phe Gly
                20                  25                  30

(2) INFORMATION FOR SEQ ID NO:77:

(i) SEQUENCE CHARACTERISTICS:
        (A) LENGTH: 45 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:77:

Met Thr Asp Ser Arg Ala Asn Arg Ala Asp Ala Thr Arg Gly Val Ala
1               5                   10                  15

Ser Val Ser Arg Arg Arg Phe Leu Ala Gly Ala Gly Leu Thr Ala Gly
                20                  25                  30

Ala Ile Ala Leu Ser Ser Met Ser Thr Ser Ala Ser Ala
            35                  40                  45

COMPOSITIONS AND METHODS FOR PROTEIN SECRETION

This is a Continuation-In-Part of application(s) 09/053,197 filed on Apr. 1, 1998 U.S. Pat. No. 6,022,952.

FIELD OF THE INVENTION

The present invention relates to compositions and methods for secretion of functional proteins in a soluble form by host cells. In particular, the invention relates to proteins involved in targeting expression of a protein of interest extracellularly and to the periplasm, thus facilitating generation of a functional soluble protein.

BACKGROUND OF THE INVENTION

Proteins having clinical or industrial value may be obtained using techniques which facilitate their synthesis in bacterial or in eukaryotic cell cultures. However, once synthesized, there are often problems in recovering these recombinant proteins in substantial yields and in a useful form. For example, recombinant proteins expressed in bacteria often accumulate in the bacterial cytoplasm as insoluble aggregates known as inclusion bodies [Marston, (1986) Biochem. J. 240:1–12; Schein (1989) Biotechnology 7:1141–1149]. Similarly, recombinant transmembrane proteins which contain both hydrophobic and hydrophilic regions are intractable to solubilization.

While transmembrane recombinant proteins and recombinant proteins which are expressed in the cytoplasm may be solubilized by use of strong denaturing solutions (e.g., urea, guanidium salts, detergents, Triton, SDS detergents, etc.), solubilization efficiency is nevertheless variable and there is no general method of solubilization which works for most proteins. Additionally, many proteins which are present at high concentrations precipitate out of solution when the solubilizing agent is removed. Yet a further drawback to solubilization of recombinant proteins is that denaturing chemicals (e.g., guanidium salts and urea) contain reactive primary amines which swamp those of the protein, thus interfering with the protein's reactive amine groups.

Thus, what is needed is a method for producing soluble proteins.

SUMMARY OF THE INVENTION

The present invention provides a recombinant polypeptide comprising at least a portion of an amino acid sequence selected from the group consisting of SEQ ID NOs:47 and 49, SEQ ID NO:7 and variants and homologs thereof, and SEQ ID NO:8 and variants and homologs thereof.

This invention further provides an isolated nucleic acid sequence encoding at least a portion of an amino acid sequence selected from the group consisting of SEQ ID NOs:47 and 49, SEQ ID NO:7 and variants and homologs thereof, and SEQ ID NO:8 and variants and homologs thereof. In one preferred embodiment, the nucleic acid sequence is contained on a recombinant expression vector. In a more preferred embodiment, the expression vector is contained within a host cell.

Also provided by the present invention is a nucleic acid sequence that hybridizes under stringent conditions to a nucleic acid sequence encoding an amino acid sequence selected from the group consisting of SEQ ID NO:7 and variants and homologs thereof, and SEQ ID NO:8 and variants and homologs thereof.

The invention additionally provides a method for expressing a nucleotide sequence of interest in a host cell to produce a soluble polypeptide sequence, the nucleotide sequence of interest when expressed in the absence of an operably linked nucleic acid sequence encoding a twin-arginine signal amino acid sequence produces an insoluble polypeptide, comprising: a) providing: i) the nucleotide sequence of interest encoding the insoluble polypeptide; ii) the nucleic acid sequence encoding the twin-arginine signal amino acid sequence; and iii) the host cell, wherein the host cell comprises at least a portion of an amino acid sequence selected from the group consisting of SEQ ID NOs:47 and 49, SEQ ID NO:7 and variants and homologs thereof, and SEQ ID NO:8 and variants and homologs thereof, b) operably linking the nucleotide sequence of interest to the nucleic acid sequence to produce a linked polynucleotide sequence; and c) introducing the linked polynucleotide sequence into the host cell under conditions such that the fused polynucleotide sequence is expressed and the soluble polypeptide is produced.

Without intending to limit the location of the insoluble polypeptide, in one preferred embodiment, the insoluble polypeptide is comprised in an inclusion body. In another preferred embodiment, the insoluble polypeptide comprises a cofactor. In a more preferred embodiment, the cofactor is selected from the group consisting of iron-sulfur clusters, molybdopterin, polynuclear copper, tryptophan tryptophylquinone, and flavin adenine dinucleotide.

Without limiting the location of the soluble polypetide to any particular location, in one preferred embodiment, the soluble polypeptide is comprised in periplasm of the host cell. In an alternative preferred embodiment, the host cell is cultured in medium, and the soluble polypeptide is contained in the medium.

The methods of the invention are not intended to be limited to any particular cell. However, in one preferred embodiment, the cell is *Escherichia coli*. In a more preferred embodiment, the *Escherichia coli* cell is D-43.

It is not intended that the invention be limited to a particular twin-arginine signal amino acid sequence. In a preferred embodiment, the twin-arginine signal amino acid sequence is selected from the group consisting of SEQ ID NO:41 and SEQ ID NO:42.

The invention further provides a method for expressing a nucleotide sequence of interest encoding an amino acid sequence of interest in a host cell, comprising: a) providing: i) the host cell; ii) the nucleotide sequence of interest; iii) a first nucleic acid sequence encoding twin-arginine signal amino acid sequence; and iv) a second nucleic acid sequence encoding at least a portion of an amino acid sequence selected from the group consisting of SEQ ID NOs:47 and 49, SEQ ID NO:7 and variants and homologs thereof, and SEQ ID NO:8 and variants and homologs thereof; b) operably fusing the nucleotide sequence of interest to the first nucleic acid sequence to produce a fused polynucleotide sequence; and c) introducing the fused polynucleotide sequence and the second nucleic acid sequence into the host cell under conditions such that the at least portion of the amino acid sequence selected from the group consisting of SEQ ID NOs:47 and 49, SEQ ID NO:7 and variants and homologs thereof, and SEQ ID NO:8 and variants and homologs thereof is expressed, and the fused polynucleotide sequence is expressed to produce a fused polypeptide sequence comprising the twin-arginine signal amino acid sequence and the amino acid sequence of interest.

The location of the expressed amino acid sequence of interest is not intended to be limited to any particular location. However, in one preferred embodiment, the expressed amino acid sequence of interest is contained in periplasm of the host cell. In a particularly preferred embodiment, the expressed amino acid sequence of interest is soluble. Also without intending to limit the location of the expressed amino acid sequence of interest, in an alternative preferred embodiment, the host cell is cultured in medium, and the expressed amino acid sequence of interest is contained in the medium. In a particularly preferred embodiment, the expressed amino acid sequence of interest is soluble.

BRIEF DESCRIPTION OF THE DRAWINGS

FIGS. 6A and 6B shows the amino acid sequence (SEQ ID NO:1) of MttA aligned with the amino acid sequence of YigT of *Haemophilus influenzae* (SEQ ID NO:2).

FIGS. 7A–7J shows the nucleotide sequence (SEQ ID NO:3) of the mttABC operon which contains the nucleotide sequence of the three open reading frames, ORF RF[3] nucleotides 5640–6439 (SEQ ID NO:4), ORF RF[2] nucleotides 6473–7246 (SEQ ID NO:5), and ORF RF[1] nucleotides 7279–8070 (SEQ ID NO:6) which encode the amino acid sequences of MttA (SEQ ID NO:1), MttB (SEQ ID NO:7) and MttC (SEQ ID NO:8), respectively.

Figure 8B:
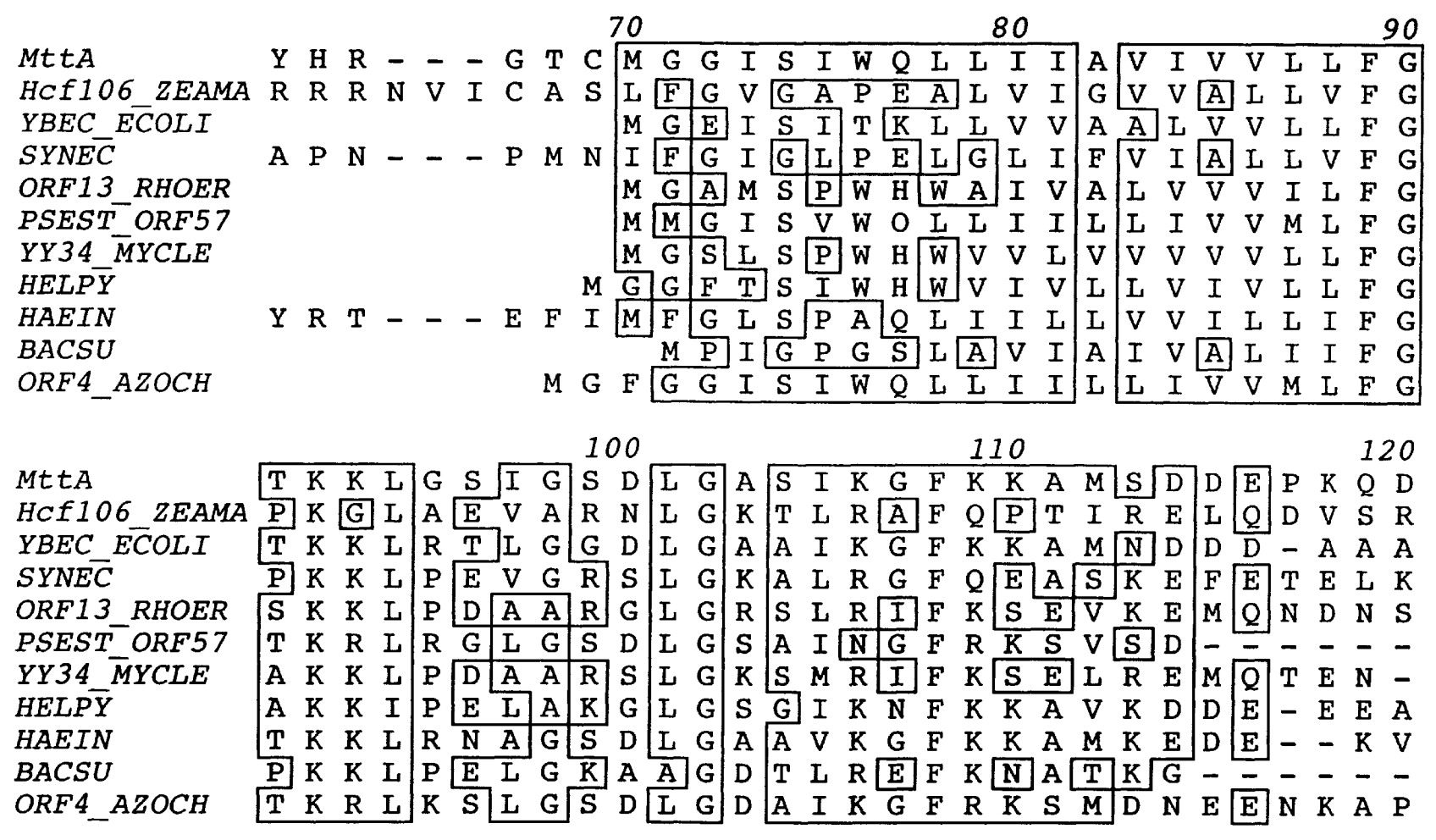

FIGS. 8A–8F shows an alignment of the amino acid sequence of the *E. coli* MttA sequence (SEQ ID NO:1) with amino acid sequences of Hcf106-ZEAMA (SEQ ID NO:9), YBEC-*E.COLI* (SEQ ID NO:10), SYNEC (SEQ ID NO:11), ORF13-RHOER (SEQ ID NO:12), PSEST-ORF57 (SEQ ID NO:13), YY34-MYCLE (SEQ ID NO:14), HELPY (SEQ ID NO:15), HAEIN (SEQ ID NO:16), BACSU (SEQ ID NO:17), and ORF4-AZOCH (SEQ ID NO:18).

FIGS. 9A and 9B show an alignment of the amino acid sequence of the *E. coli* MttB sequence (SEQ ID NO:7) with amino acid sequences of YC43-PROPU (SEQ ID NO:19), YM16-MARPO (SEQ ID NO:20), ARATH (SEQ ID NO:21), Ymf16-RECAM (SEQ ID NO:22), Y194-SYNY3 (SEQ ID NO:23), YY33-MYCTU (SEQ ID NO:24), HELPY (SEQ ID NO:25), YigU-HAEIN (SEQ ID NO:26), YcbT-BACSU (SEQ ID NO:27), YH25-AZOCH (SEQ ID NO:28) and ARCFU (SEQ ID NO:29).

FIGS. 10A and 10B show an alignment of the amino acid sequence of the *E. coli* MttC sequence (SEQ ID NO:8) with amino acid sequences of YCFH-*ECOLI* (SEQ ID NO:30), YJJV-*E.COLI* (SEQ ID NO:31), METTH (SEQ ID NO:32), Y009-MYCPN (SEQ ID NO:33), YcfH-Myctu (SEQ ID NO:34), HELPY (SEQ ID NO:35), YCFH-HAEIN (SEQ ID NO:36), YABC-BACSU (SEQ ID NO:37), SCHPO (SEQ ID NO:38), CAEEL (SEQ ID NO:39) and Y218-HUMAN (SEQ ID NO:40).

FIGS. 11A–11E show the nucleotide sequence (SEQ ID NO:45) of the mttABC operon which contains the mttA1 nucleotide sequence (SEQ ID NO:46) (from nucleic acid number 642 to nucleic acid number 953) encoding the amino acid sequence of MttA1 (SEQ ID NO:47), and the mttA2 nucleotide sequence (SEQ ID NO:48) (from nucleic acid number 958 to nucleic acid number 1472) encoding the amino acid sequence of MttA2 (SEQ ID NO:49).

DEFINITIONS

Figure 1A:
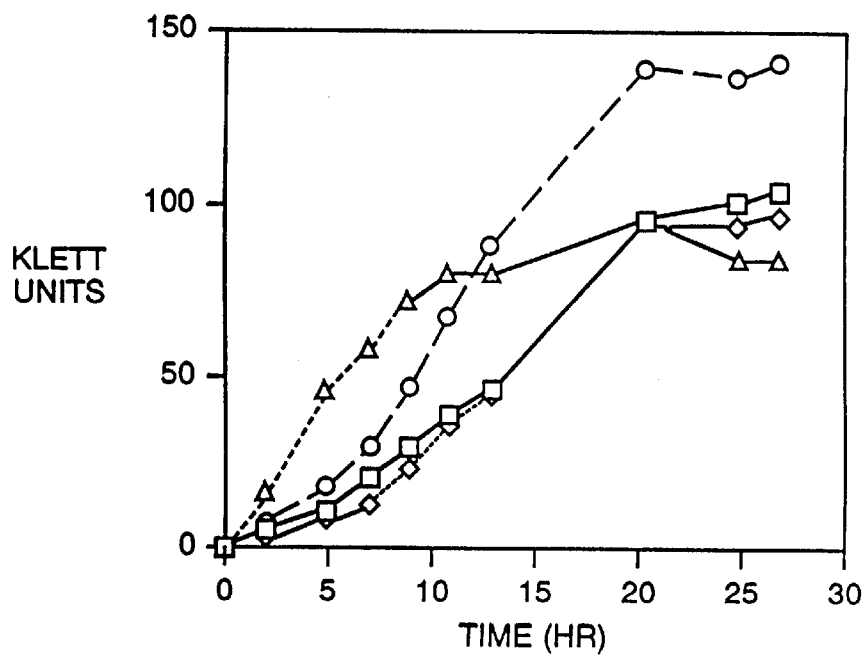
FIGS. 1A and 1B show anaerobic growth of strain HB101 (FIG. 1A) and D-43 (FIG. 1B) in the presence of various electron acceptors: (△) 40 mM nitrate, (□) 35 mM fumarate, (○) 100 mM TMAO or (◇) 70 mM DMSO.

To facilitate understanding of the invention, a number of terms are defined below.

The term "foreign gene" refers to any nucleic acid (e.g., gene sequence) which is introduced into a cell by experimental manipulations and may include gene sequences found in that cell so long as the introduced gene contains some modification (e.g., a point mutation, the presence of a selectable marker gene, etc.) relative to the naturally-occurring gene.

The term "gene" refers to a DNA sequence that comprises control and coding sequences necessary for the production of RNA or a polypeptide. The polypeptide can be encoded by a full length coding sequence or by any portion of the coding sequence.

The terms "gene of interest" and "nucleotide sequence of interest" refer to any gene or nucleotide sequence, respectively, the manipulation of which may be deemed desirable for any reason, by one of ordinary skill in the art. Such nucleotide sequences include, but are not limited to, coding sequences of structural genes (e.g., reporter genes, selection marker genes, oncogenes, drug resistance genes, growth factors, etc.), and of regulatory genes (e.g., activator protein 1 (AP1), activator protein 2 (AP2), Sp1, etc.). Additionally, such nucleotide sequences include non-coding regulatory elements which do not encode an mRNA or protein product, such as for example, a promoter sequence, an enhancer sequence, etc.

As used herein the term "coding region" when used in reference to a structural gene refers to the nucleotide sequences which encode the amino acids found in the nascent polypeptide as a result of translation of an mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

Transcriptional control signals in eukaryotes comprise "promoter" and "enhancer" elements. Promoters and enhancers consist of short arrays of DNA sequences that interact specifically with cellular proteins involved in transcription [Maniatis, et al., Science 236:1237 (1987)]. Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types [for review see Voss, et al., Trends Biochem. Sci., 11:287 (1986) and Maniatis, et al., Science 236:1237 (1987)].

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "expression vector" as used herein refers to a recombinant DNA molecule containing a desired coding sequence and appropriate nucleic acid sequences necessary for the expression of the operably linked coding sequence in a particular host cell. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals.

The terms "targeting vector" or "targeting construct" refer to oligonucleotide sequences comprising a gene of interest flanked on either side by a recognition sequence which is capable of homologous recombination of the DNA sequence located between the flanking recognition sequences into the chromosomes of the target cell or recipient cell. Typically, the targeting vector will contain 10 to 15 kb of DNA homologous to the gene to be recombined; this 10 to 15 kb of DNA is generally divided more or less equally on each side of the selectable marker gene. The targeting vector may contain more than one selectable maker gene. When more than one selectable marker gene is employed, the targeting vector preferably contains a positive selectable marker (e.g., the neo gene) and a negative selectable marker (e.g., the Herpes simplex virus tk (HSV-tk) gene). The presence of the positive selectable marker permits the selection of recipient cells containing an integrated copy of the targeting vector whether this integration occurred at the target site or at a random site. The presence of the negative selectable marker permits the identification of recipient cells containing the targeting vector at the targeted site (i.e., which has integrated by virtue of homologous recombination into the target site); cells which survive when grown in medium which selects against the expression of the negative selectable marker do not contain a copy of the negative selectable marker. Integration of a replacement-type vector results in the insertion of a selectable marker into the target gene. Replacement-type targeting vectors may be employed to disrupt a gene resulting in the generation of a null allele (i.e., an allele incapable of expressing a functional protein; null alleles may be generated by deleting a portion of the coding region, deleting the entire gene, introducing an insertion and/or a frameshift mutation, etc.) or may be used to introduce a modification (e.g., one or more point mutations) into a gene.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the terms "vector" and "vehicle" are used interchangeably in reference to nucleic acid molecules that transfer DNA segment(s) from one cell to another.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed using a recombinant DNA molecule.

The term "transfection" as used herein refers to the introduction of a transgene into a cell. The term "transgene" as used herein refers to any nucleic acid sequence which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence which is naturally found in the cell into which it is introduced so long as it does not contain some modification (e.g., a point mutation, the presence of a selectable marker gene, etc.) relative to the naturally-occurring sequence. The term "heterologous DNA sequence" refers to a nucleotide sequence which is not endogenous to the cell into which it is introduced. Heterologous DNA includes a nucleotide sequence which is ligated to, or is manipulated to become ligated to, a nucleic acid sequence to which it is not ligated in nature, or to which it is ligated at a different location in nature. Heterologous DNA also includes a nucleotide sequence which is naturally found in the cell into which it is introduced and which contains some modification relative to the naturally-occurring sequence. Generally, although not necessarily, heterologous DNA encodes RNA and proteins that are not normally produced by the cell into which it is introduced. Examples of heterologous DNA include reporter genes, transcriptional and translational regulatory sequences, DNA sequences which encode selectable marker proteins (e.g., proteins which confer drug resistance), etc. Yet another example of a heterologous DNA includes a nucleotide sequence which encodes a ribozyme which is found in the cell into which it is introduced, and which is ligated to a promoter sequence to which it is not naturally ligated in that cell.

Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, biolistics (i.e., particle bombardment) and the like.

The term "stable transfection" or "stably transfected" refers to the introduction and integration of a transgene into the genome of the transfected cell. The term "stable transfectant" refers to a cell which has stably integrated one or more transgenes into the genomic DNA.

As used herein the term "portion" when in reference to a gene refers to fragments of that gene. The fragments may range in size from 5 nucleotide residues to the entire nucleotide sequence minus one nucleic acid residue. Thus, "an oligonucleotide comprising at least a portion of a gene" may comprise small fragments of the gene or nearly the entire gene.

The term "portion" when used in reference to a protein (as in a "portion of a given protein") refers to fragments of that protein. The fragments may range in size from four amino acid residues to the entire amino acid sequence minus one amino acid.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, isolated nucleic acid sequences encoding MttA1, MttA2, MttB or MttC polypeptides include, by way of example, such nucleic acid sequences in cells ordinarily expressing MttA1, MttA2, MttB or MttC polypeptides, respectively, where the nucleic acid sequences are in a chromosomal or extrachromosomal location different from that of natural cells, or are otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may be single-stranded). Alternatively, it may contain both the sense and anti-sense strands (i.e., the oligonucleotide may be double-stranded).

As used herein, the term "purified" or "to purify" refers to the removal of undesired components from a sample. For example, where recombinant MttA1, MttA2, MttB or MttC polypeptides are expressed in bacterial host cells, the MttA1, MttA2, MttB or MttC polypeptides are purified by the removal of host cell proteins thereby increasing the percent of recombinant MttA1, MttA2, MttB or MttC polypeptides in the sample.

As used herein, the term "substantially purified" refers to molecules, either nucleic or amino acid sequences, that are removed from their natural environment, isolated or separated, and are at least 60% free, preferably 75% free, and more preferably 90% free from other components with which they are naturally associated. An "isolated polynucleotide" is therefore a substantially purified polynucleotide.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed using a recombinant DNA molecule.

The term "homology" when used in relation to nucleic acids refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe (i.e., an oligonucleotide which is capable of hybridizing to another oligonucleotide of interest) will compete for and inhibit the binding (i.e., the hybridization) of a completely homologous sequence to a target under conditions of low stringency. This is not to say that conditions of low stringency are such that nonspecific binding is permitted; low stringency conditions require that the binding of two sequences to one another be a specific (i.e., selective) interaction. The absence of nonspecific binding may be tested by the use of a second target which lacks even a partial degree of complementarity (e.g., less than about 30% identity); in the absence of nonspecific binding the probe will not hybridize to the second non-complementary target.

Low stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

High stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

When used in reference to nucleic acid hybridization the art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of ribonucleotides along the mRNA chain, and also determines the order of amino acids along the polypeptide (protein) chain. The DNA sequence thus codes for the RNA sequence and for the amino acid sequence.

"Nucleic acid sequence" and "nucleotide sequence" as used interchangeably herein refer to an oligonucleotide or polynucleotide, and fragments or portions thereof, and to DNA or RNA of genomic or synthetic origin which may be single- or double-stranded, and represent the sense or anti-sense strand.

"Amino acid sequence" and "polypeptide sequence" are used interchangeably herein to refer to a sequence of amino acids.

The term "antisense sequence" as used herein refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Sense mRNA generally is ultimately translated into a polypeptide. Thus an "antisense" sequence is a sequence having the same sequence as the non-coding strand in a DNA duplex. The term "antisense RNA" refers to a ribonucleotide sequence whose sequence is complementary to an "antisense" sequence. Alternatively, the term "antisense RNA" is used in reference to RNA sequences which are complementary to a specific RNA sequence (e.g., mRNA). Antisense RNA may be produced by any method, including synthesis by splicing the gene(s) of interest in a reverse orientation to a viral promoter which permits the synthesis of a coding strand. Once introduced into a cell, this transcribed strand combines with natural mRNA produced by the cell to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative" ) is sometimes used in reference to the antisense strand, with the designation (+) sometimes used in reference to the sense (i.e., "positive") strand.

The term "biologically active" when made in reference to MttA1, MttA2, MttB or MttC refers to a MttA1, MttA2, MttB or MttC molecule, respectively, having biochemical functions of a naturally occurring MttA1, MttA2, MttB or MttC. Biological activity of MttA, MttB or MttC is determined, for example, by restoration of wild-type targeting of proteins which contain twin-arginine signal amino acid sequence to cell membranes and/or translocation of such proteins to the periplasm in cells lacking MttA1, MttA2, MttB or MttC activity (i.e., MttA1, MttA2, MttB or MttC null cells). Cells lacking MttA1, MttA2, MttB or MttC activity may be produced using methods well known in the art (e.g., point mutation and frame-shift mutation) [Sambasivarao et al (1991) J. Bacteriol. 5935–5943; Jasin et al (1984) J. Bacteriol. 159:783–786]. Complementation is achieved by transfecting cells which lack MttA1, MttA2, MttB or MttC activity with an expression vector which expresses MttA1, MttA2, MttB or MttC, a homolog thereof, or a portion thereof. Details concerning complementation of cells which contain a point mutation in MttA is provided in Example 6 herein.

As used herein "soluble" when in reference to a protein produced by recombinant DNA technology in a host cell is a protein which exists in solution; if the protein contains a twin-arginine signal amino acid sequence the soluble protein is exported to the periplasmic space in gram negative bacterial hosts and is secreted into the culture medium by eukaryotic cells capable of secretion or by bacterial host possessing the appropriate genes (i.e., the kil gene). Thus, a soluble protein is a protein which is not found in an inclusion body inside the host cell. Alternatively, a soluble protein is a protein which is not found integrated in cellular membranes. In contrast, an insoluble protein is one which exists in denatured form inside cytoplasmic granules (called an inclusion body) in the host cell. Alternatively, an insoluble protein is one which is present in cell membranes, including but not limited to, cytoplasmic membranes, mitochondrial membranes, chloroplast membranes, endoplasmic reticulum membranes, etc.

A distinction is drawn between a soluble protein (i.e., a protein which when expressed in a host cell is produced in a soluble form) and a "solubilized" protein. An insoluble recombinant protein found inside an inclusion body or found integrated in a cell membrane may be solubilized (i.e., rendered into a soluble form) by treating purified inclusion bodies or cell membranes with denaturants such as guanidine hydrochloride, urea or sodium dodecyl sulfate (SDS). These denaturants must then be removed from the solubilized protein preparation to allow the recovered protein to renature (refold). Not all proteins will refold into an active conformation after solubilization in a denaturant and removal of the denaturant. Many proteins precipitate upon removal of the denaturant. SDS may be used to solubilize inclusion bodies and cell membranes and will maintain the proteins in solution at low concentration. However, dialysis will not always remove all of the SDS (SDS can form micelles which do not dialyze out); therefore, SDS-solubilized inclusion body protein and SDS-solubilized cell membrane protein is soluble but not refolded.

A distinction is also drawn between proteins which are soluble ( i.e., dissolved) in a solution devoid of significant amounts of ionic detergents (e.g., SDS) or denaturants (e.g., urea, guanidine hydrochloride) and proteins which exist as a suspension of insoluble protein molecules dispersed within the solution. A soluble protein will not be removed from a solution containing the protein by centrifugation using conditions sufficient to remove cells present in a liquid medium (e.g., centrifugation at 5,000×g for 4–5 minutes).

DESCRIPTION OF THE INVENTION

The present invention exploits the identification of proteins involved in a Sec-independent protein translocation pathway which are necessary for the translocation of proteins which contain twin-arginine signal amino acid sequences to the periplasm of gram negative bacteria, and into the extracellular media of cells which do not contain a periplasm (e.g., gram positive bacteria, eukaryotic cells, etc.), as well as for targeting such proteins to cell membranes. The proteins of the invention are exemplified by the Membrane Targeting and Translocation proteins MttA1 (103 amino acids), MHA2 (161 amino acids), MttB (258 amino acids) and MttC (264 amino acids) of $E.\ coli$ which are encoded by the mttABC operon. The invention further exploits the presence of a large number of proteins which are widely distributed in organisms extending from archaebacteria to higher eukaryotes.

The well characterized Sec-dependent export system translocates an unfolded string of amino acids to the periplasm and folding follows as a subsequent step in the periplasm and mediated by chaperones and disulfide rearrangement. In contrast to the Sec-dependent export pathway, the proteins of the invention translocate fully-folded as well as cofactor-containing proteins from the cytoplasm into the bacterial periplasm and are capable of translocating such proteins into extracellular medium. Such translocation offers a unique advantage over current methodologies for protein purification. Because the composition of culture medium can be manipulated, and because the periplasm contains only about 3% of the proteins of gram negative bacteria, expressed proteins which are translocated into the extracellular medium or into the periplasm are more likely to be expressed as functional soluble proteins than if they were translocated to cellular membranes or to the cytoplasm. Furthermore, translocation to the periplasm or to the extracellular medium following protein expression in the cytoplasm allows the expressed protein to be correctly folded by cytoplasmic enzymes prior to its translocation, thus allowing retention of the expressed protein's biological activity.

The mttABC operon disclosed herein is also useful in screening compounds for antibiotic activity by identifying those compounds which inhibit translocation of proteins containing twin-arginine signal amino acid sequences in bacteria. For example, DMSO reductase has been found to be essential for the pathogenesis of Salmonella [Bowe and Heffron (1994) Methods in Enzymology 236:509–526]. Thus, compounds which inhibit targeting of DMSO reductase to Salmonella could result in conversion of a virulent bacterial strain to an a virulent nonpathogenic variant.

The invention is further described under (A) mttA, mttB, and mttC nucleotide sequences, (B) MttA, MttB, and MttC polypeptides, and (C) Methods for expressing polypeptides to produce soluble proteins.

A. mttA, mttB, and mttC Nucleotide Sequences

The present invention discloses the nucleic acid sequence of the mttA1 (SEQ ID NO:46), MttA2 (SEQ ID NO:48), mttB (SEQ ID NO:5) and mttC (SEQ ID NO:6) genes which form part of the mttABC operon (SEQ ID NO:45) shown in FIGS. 11A–11E. Data presented herein demonstrates that the MttA2 polypeptide encoded by mttA2 functions in targeting proteins which contain twin-arginine signal amino acid sequences to cell membranes, and in translocating such proteins to the periplasm of gram negative bacteria and to the extracellular medium of cells which do not contain a periplasm (e.g., gram positive bacteria and eukaryotic cells). Data presented herein further shows that the MttB and MttC polypeptides which are encoded by mttB and mttC, respectively, also serve the same functions as MttA2. This conclusion is based on the inventors' finding that mttA1, MttA2, mttB and mttC form an operon which is expressed as a single polycistronic mRNA.

The function of MttB and MttC may be demonstrated by in vivo homologous recombination of chromosomal mttB and mttC by using knockouts in the mttBC operon by utilizing insertion of mini-MudII as previously described [Taylor et al. (1994) J. Bacteriol. 176:2740–2742]. Alternatively, the function of MttB and MttC may also be demonstrated as previously described [Sambasivarao et al (1991) J. Bacteriol. 5935–5943; Jasin et al (1984) J. Bacteriol. 159:783–786]. Briefly, the mttBC operon (FIGS. 11A–11E) is cloned into pTZ18R and pBR322 vectors. In pBR322, the HindIII site in mttB is unique. The pBR322 containing mttB is then modified by insertion of a kanamycin gene cartridge at this unique site, while the unique NruI fragment contained in mttC are replaced by a kanamycin cartridge. The modified plasmids are then be homologously recombined with chromosomal mttB and mttC in *E. coli* cells which contain either a recBC mutation or a recD mutation. The resulting recombinant are transferred by P1 transduction to suitable genetic backgrounds for investigation of the localization of protein expression. The localization (e.g., cytoplasm, periplasm, cell membranes, extracellular medium) of expression of proteins which contain twin-arginine signal amino acid sequences is compared using methods disclosed herein (e.g., functional enzyme activity and Western blotting) between homologously recombined cells and control cells which had not been homologously recombined. Localization of expressed proteins which contain twin-arginine signal amino acid sequences in extracellular medium or in the periplasm of homologously recombined cells as compared to localization of expression in other than the extracellular medium and the periplasm (e.g., in the cytoplasm, in the cell membrane, etc.) of control cells demonstrates that the wild-type MttB or MttC protein whose function had been modified by homologous recombination functions in translocation of the twin argining containing proteins to the extracellular medium or to the periplasm.

The present invention contemplates any nucleic acid sequence which encodes one or more of MttA1, MttA2, MttB and MttC polypeptide sequences or variants or homologs thereof. These nucleic acid sequences are used to make recombinant molecules which express the MttA, MttB and MttC polypeptides. For example, one of ordinary skill in the art would recognize that the redundancy of the genetic code permits an enormous number of nucleic acid sequences which encode the MttA, MttB and MttC polypeptides. Thus, codons which are different from those shown in FIGS. 11A–11E may be used to increase the rate of expression of the nucleotide sequence in a particular prokaryotic or eukaryotic expression host which has a preference for particular codons. Additionally, alternative codons may also be used in eukaryotic expression hosts to generate splice variants of recombinant RNA transcripts which have more desirable properties (e.g., longer or shorter half-life) than transcripts generated using the sequence depicted in FIGS. 11–11E. In addition, different codons may also be desirable for the purpose of altering restriction enzyme sites or, in eukaryotic expression hosts, of altering glycosylation patterns in translated polypeptides.

The nucleic acid sequences of the invention may also be used for in vivo homologous recombination with chromosomal nucleic acid sequences. Homologous recombination may be desirable to, for example, delete at least a portion of at least one of chromosomal mttA1, mttA2, mttB and mttC nucleic acid sequences, or to introduce a mutation in these chromosomal nucleic acid sequence as described below.

Variants of the nucleotide sequences which encode MttA1, MttA2, MttB and MttC and which are shown in FIGS. 7A–7J and FIGS. 11A–11E are also included within the scope of this invention. These variants include, but are not limited to, nucleotide sequences having deletions, insertions or substitutions of different nucleotides or nucleotide analogs.

This invention is not limited to the mttA1, mttA2, mttB and mttC sequences (SEQ ID NOs:46, 48, 5 and 6, respectively) but specifically includes nucleic acid homologs which are capable of hybridizing to the nucleotide sequence encoding MttA1, MttA2, MttB and MttC (FIGS. 11A–11E and FIGS. 7A–7J), and to portions, variants and homologs thereof. Those skilled in the art know that different hybridization stringencies may be desirable. For example, whereas higher stringencies may be preferred to reduce or eliminate non-specific binding between the nucleotide sequences of FIGS. 7A–7J and other nucleic acid sequences, lower stringencies may be preferred to detect a larger number of nucleic acid sequences having different homologies to the nucleotide sequence of FIGS. 7A–7J.

Portions of the nucleotide sequence encoding MttA1, MttA2, MttB and MttC of FIGS. 11A–11E and FIGS. 7A–7J are also specifically contemplated to be within the scope of this invention. It is preferred that the portions have a length equal to or greater than 10 nucleotides and show greater than 50% homology to nucleotide sequences encoding MttA1, MttA2, MttB and MttC of FIGS. 11A–11E and FIGS. 7A–7J.

The present invention further contemplates antisense molecules comprising the nucleic acid sequence complementary to at least a portion of the polynucleotide sequences encoding MttA1, MttA2, MttB and MttC (FIGS. 11A–11E and FIGS. 7A–7J).

The scope of this invention further encompasses nucleotide sequences containing the nucleotide sequence of FIGS. 11A–11E and FIGS. 7A–7J, portions, variants, and homologs thereof, ligated to one or more heterologous sequences as part of a fusion gene. Such fusion genes may be desirable, for example, to detect expression of sequences which form part of the fusion gene. Examples of a heterologous sequence include the reporter sequence encoding the enzyme β-galactosidase or the enzyme luciferase. Fusion genes may also be desirable to facilitate purification of the expressed protein. For example, the heterologous sequence of protein A allows purification of the fusion protein on immobilized immunoglobulin. Other affinity traps are well known in the art and can be utilized to advantage in purifying the expressed fusion protein. For example, pGEX vectors (Promega, Madison Wis.) may be used to express the MttA1, MttA2, MttB and MttC polypeptides as a fusion protein with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

The nucleotide sequences which encode MttA1, MttA2, MttB and MttC (FIGS. 11A–11E and FIGS. 7A–7J), portions, variants, and homologs thereof can be synthesized by synthetic chemistry techniques which are commercially available and well known in the art. The nucleotide sequence of synthesized sequences may be confirmed using commercially available kits as well as from methods well known in the art which utilize enzymes such as the Klenow fragment of DNA polymerase I, Sequenase®, Taq DNA polymerase, or thermostable T7 polymerase. Capillary electrophoresis may also be used to analyze the size and confirm the nucleotide sequence of the products of nucleic acid synthesis. Synthesized sequences may also be amplified using the polymerase chain reaction (PCR) as described by Mullis [U.S. Pat. No. 4,683,195] and Mullis et al. [U.S. Pat. No. 4,683,202], the ligase chain reaction [LCR; sometimes referred to as "Ligase Amplification Reaction" (LAR)] described by Barany, Proc. Natl. Acad. Sci., 88:189 (1991); Barany, PCR Methods and Applic., 1:5 (1991); and Wu and Wallace, Genomics 4:560 (1989).

It is readily appreciated by those in the art that the mttA1, mttA2, mttB and mttC nucleotide sequences of the present invention may be used in a variety of ways. For example, fragments of the sequence of at least about 10 bp, more usually at least about 15 bp, and up to and including the entire (i.e., full-length) sequence can be used as probes for the detection and isolation of complementary genomic DNA sequences from any cell. Genomic sequences are isolated by screening a genomic library with all or a portion of the nucleotide sequences which encode MttA1, MttA2, MttB and MttC (FIGS. 11A–11E and FIGS. 7A–7J). In addition to screening genomic libraries, the mttA1, mttA2, mttB and mttC nucleotide sequences can also be used to screen cDNA libraries made using RNA.

The mttA1, mttA2, mttB and mttC nucleotide sequences of the invention are also useful in directing the synthesis of MttA1, MttA2, MttB, and MttC, respectively. The MttA1, MttA2, MttB, and MttC polypeptides find use in producing antibodies which may be used in, for example, detecting cells which express MttA1, MttA2, MttB and MttC. These cells may additionally find use in directing expression of recombinant proteins to cellular membranes or to the periplasm, extracellular medium. Alternatively, cells containing at least one of MttA1, MttA2, MttB and MttC may be used to direct expression of recombinant proteins which are engineered to contain twin-arginine signal amino acid sequences, or of wild-type proteins which contain twin-arginine signal amino acid sequences, to the periplasm or extracellularly (as described below), thus reducing the likelihood of formation of insoluble proteins.

B. MttA, MttB, and MttC Polypeptides

This invention discloses the amino acid sequence of MttA1 (SEQ ID NO:47), and MttA2 (SEQ ID NO:49) which are encoded by the mttA1 and mttA2 genes, respectively. Data presented herein demonstrates that the protein MttA2 targets twin arginine containing proteins (i.e., proteins which contain twin-arginine signal amino acid sequences), as exemplified by the proteins dimethylsulfoxide (DMSO) reductase (DmsABC) to the cell membrane (Examples 2 and 5). The function of MttA2 in membrane targeting of twin arginine containing proteins was demonstrated by isolating a pleiotropic-negative mutant in mttA2 which prevents the correct membrane targeting of Escherichia coli dimethylsulfoxide reductase and results in accumulation of DmsA in the cytoplasm. DmsABC is an integral membrane molybdoenzyme which normally faces the cytoplasm and the DmsA subunit has a twin-arginine signal amino acid sequence. The mutation in mttA2 changed proline 25 to leucine in the encoded MttA2, and was complemented by a DNA fragment encoding the mttA2 gene.

Data presented herein further demonstrates that MttA2 also functions in selectively translocating twin arginine containing proteins, as exemplified by nitrate reductase (NapA) and trimethylamine N-oxide reductase (TorA), to the periplasm (Example 4). The mutation in the mttA2 gene resulted in accumulation of the periplasmic proteins NapA and TorA in the cytoplasm and cell membranes. In contrast, proteins with a sec-dependent leader, as exemplified by nitrite reductase (NrfA), or which contain a twin-arginine signal amino acid sequence and which assemble spontaneously in the membrane, as exemplified by trimethylamine N-oxide (TMAO), were not affected by this mutation (Examples 2 and 4).

The isolation of mutant D-43 which contained a mutant mttA2 gene was unexpected. The assembly of multisubunit redox membrane proteins in bacteria and eukaryotic organelles has been assumed to be a spontaneous process mediated by protein-protein interactions between the integral anchor subunit(s) and the extrinsic subunit(s) [Latour and Weiner (1987) J. Gen. Microbiol. 133:597–607; Lemire et al. (1983) J. Bacteriol. 155:391–397]. It has previously been shown that the extrinsic subunits of fumarate reductase, FrdAB, can be reconstituted to form the holoenzyme with the anchor subunits, FrdCD, in vitro without any additional proteins [Lemire et al. (1983) J. Bacteriol. 155:391–397]. Because the architecture of DMSO reductase is similar to that of fumarate reductase, it seemed likely that this protein assembled in a similar manner. However, data presented herein demonstrates that this was not the case. Thus, the isolation of mutant D-43 was unexpected and it suggests that the assembly of DmsABC needs auxiliary proteins for optimal efficiency. Alternatively, the assembly of DmsABC may be an evolutionary vestige related to the soluble periplasmic DMSO reductase found in several organisms [McEwan (1994) Antonie van Leeuwenhoek 66:151–164; McEwan et al. (1991) Biochem. J. 274:305–307].

Without limiting the invention to a particular mechanism, MttA is predicted to be a membrane protein with two transmembrane segments and a long periplasmic α-helix. Proline 25 is located after the second transmembrane helix and immediately preceding the long periplasmic α-helix suggesting the essential nature of this region of MttA2.

Interestingly, the smallest complementing DNA fragment, pGS20, only encoded the amino terminal two thirds of MttA2. This suggests that the carboxy terminal globular domain is not necessary or can be substituted by some other activity. This conclusion is further supported by the observation that the carboxy terminal third of MttA2 is also the least conserved region of MttA2. While the amino terminal of MttA2 is homologous to YigT of Settles et al (1997) Science 278:1467–1470, the YigT sequence was not correct throughout its length. Data presented herein shows that proteins which were homologous to MttA were identified by BLAST searches in a wide variety of archaebacteria, eubacteria, cyanobacteria and plants, suggesting that the sec-independent translocation system of which MttA1 and MttA2 are members is very widely distributed in nature.

The invention further discloses the amino acid sequence of MttB (SEQ ID NO:7) and MttC (SEQ ID NO:8). Without limiting the invention to any particular mechanism, MttB is an integral membrane protein with six transmembrane segments and MttC is a membrane protein with one or two transmembrane segments and a large cytoplasmic domain. Proteins homologous to MttB were identified by BLAST searches in a wide variety of archaebacteria, eubacteria, cyanobacteria and plants, suggesting that the protein translocation system of which MttB is a member is very widely distributed in nature. The MttC protein was even more widely dispersed with homologous proteins identified in archaebacteria, mycoplasma, eubacteria, cyanobacteria, yeast, plants, C. elegans and humans. In all cases the related proteins were of previously unknown function.

Without limiting the invention to any particular mechanism, the predicted topology of the MttABC proteins suggests that the large cytoplasmic domain of MttC serves a receptor function for twin arginine containing proteins, with the integral MttB protein serving as the pore for protein transport. Based on the observation that the MttA2 can form a long α-helix, this protein is predicted to play a role in gating the pore.

The present invention specifically contemplates variants and homologs of the amino acid sequences of MttA1, MttA2, MttB and MttC. A "variant" of MttA1, MttA2, MttB and MttC is defined as an amino acid sequence which differs by one or more amino acids from the amino acid sequence of MttA1 (SEQ ID NO:47), MttA2 (SEQ ID NO:49), MttB (SEQ ID NO:7) and MttC (SEQ ID NO:8), respectively. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions (i.e., additions), or both. Guidance in determining which and how many amino acid residues may be substituted, inserted or deleted without abolishing biological or immunological activity may be found using computer programs well known in the art, for example, DNAStar software.

For example, MttA1, MttA2, MttB and MttC variants included within the scope of this invention include MttA1, MttA2, MttB and MttC polypeptide sequences containing deletions, insertion or substitutions of amino acid residues which result in a polypeptide that is functionally equivalent to the MttA1, MttA2, MttB and MttC polypeptide sequences of FIGS. 11A–11E and FIGS. 7A–7J. For example, amino acids may be substituted for other amino acids having similar characteristics of polarity, charge, solubility, hydrophobicity, hydrophilicity and/or amphipathic nature. Alternatively, substitution of amino acids with other amino acids having one or more different characteristic may be desirable for the purpose of producing a polypeptide which is secreted from the cell in order to, for example, simplify purification of the polypeptide.

The present invention also specifically contemplates homologs of the amino acid sequences of MttA1, MttA2, MttB and MttC. An oligonucleotide sequence which is a "homolog" of MttA1 (SEQ ID NO:47), MttA2 (SEQ ID NO:49), MttB (SEQ ID NO:7) and MttC (SEQ ID NO:8) is defined herein as an oligonucleotide sequence which exhibits greater than or equal to 50% identity to the sequence of MttA1 (SEQ ID NO:47), MttA2 (SEQ ID NO:49), MttB (SEQ ID NO:7) and MttC (SEQ ID NO:8), respectively, when sequences having a length of 20 amino acids or larger are compared. Alternatively, a homolog of MttA1 (SEQ ID NO:47), MttA2 (SEQ ID NO:49), MttB (SEQ ID NO:7) and MttC (SEQ ID NO:8) is defined as an oligonucleotide sequence which encodes a biologically active MttA1, MttA2, MttB and MttC amino acid sequence, respectively.

The MttA1, MttA2, MttB and MttC polypeptide sequence of FIGS. 11A–11E and FIGS. 7A–7J and their functional variants and homologs may be made using chemical synthesis. For example, peptide synthesis of the MttA1, MttA2, MttB and MttC polypeptides, in whole or in part, can be performed using solid-phase techniques well known in the art. Synthesized polypeptides can be substantially purified by high performance liquid chromatography (HPLC) techniques, and the composition of the purified polypeptide confirmed by amino acid sequencing. One of skill in the art would recognize that variants and homologs of the MttA1, MttA2, MttB and MttC polypeptide sequences can be produced by manipulating the polypeptide sequence during and/or after its synthesis.

MttA1, MttA2, MttB and MttC and their functional variants and homologs can also be produced by an expression system. Expression of MttA1, MttA2, MttB and MttC may be accomplished by inserting the nucleotide sequence encoding MttA1, MttA2, MttB and MttC (FIGS. 11A–11E and 7A–7J), its variants, portions, or homologs into appropriate vectors to create expression vectors, and transfecting the expression vectors into host cells.

Expression vectors can be constructed using techniques well known in the art [Sambrook et al. (1989) Molecular Cloning, A Laboratory Manual, Cold Spring Harbor Press, Plainview N.Y.; Ausubel et al. (1989) Current Protocols in Molecular Biology, John Wiley & Sons, New York N.Y.]. Briefly, the nucleic acid sequence of interest is placed in operable combination with transcription and translation regulatory sequences. Regulatory sequences include initiation signals such as start (i.e., ATG) and stop codons, promoters which may be constitutive (i.e., continuously active) or inducible, as well as enhancers to increase the efficiency of expression, and transcription termination signals. Transcription termination signals must be provided downstream from the structural gene if the termination signals of the structural gene are not included in the expression vector. Expression vectors may become integrated into the genome of the host cell into which they are introduced, or are present as unintegrated vectors. Typically, unintegrated vectors are transiently expressed and regulated for several hours (eg., 72 hours) after transfection.

The choice of promoter is governed by the type of host cell to be transfected with the expression vector. Host cells include bacterial, yeast, plant, insect, and mammalian cells. Transfected cells may be identified by any of a number of marker genes. These include antibiotic (e.g., gentamicin, penicillin, and kanamycin) resistance genes as well as marker or reporter genes (e.g., β-galactosidase and luciferase) which catalyze the synthesis of a visible reaction product.

Expression of the gene of interest by transfected cells may be detected either indirectly using reporter genes, or directly by detecting mRNA or protein encoded by the gene of interest. Indirect detection of expression may be achieved by placing a reporter gene in tandem with the sequence encoding one or more of MttA1, MttA2, MttB and MttC under the control of a single promoter. Expression of the reporter gene indicates expression of the tandem one or more MttA1, MttA2, MttB and MttC sequence. It is preferred that the reporter gene have a visible reaction product. For example, cells expressing the reporter gene P-galactosidase produce a blue color when grown in the presence of X-Gal, whereas cells grown in medium containing luciferin will fluoresce when expressing the reporter gene luciferase.

Direct detection of MttA1, MttA2, MttB and MttC expression can be achieved using methods well known to those skilled in the art. For example, mRNA isolated from transfected cells can be hybridized to labelled oligonucleotide probes and the hybridization detected. Alternatively, polyclonal or monoclonal antibodies specific for MttA1, MttA2, MttB and MttC can be used to detect expression of the MttA, MttB and MttC polypeptide using enzyme-linked immunosorbent assay (ELISA), radioimmunoassay (RIA) and fluorescent activated cell sorting (FACS).

Those skilled in the art recognize that the MttA1, MttA2, MttB and MttC polypeptide sequences of the present invention are useful in generating antibodies which find use in detecting cells that express MttA1, MttA2, MttB and MttC or proteins homologous thereto. Such detection is useful in the choice of host cells which may be used to target recombinant twin arginine containing protein expression to cellular membranes or to the periplasm or to the extracellular medium. Additionally, such detection is particularly useful in selecting host cells for cytoplasmic or extracellular expression of recombinant twin arginine containing proteins by disrupting the function of at least one of MttA1, MttA2, MttB and MttC as described below.

C. Methods for Expressing Polypeptides to Produce Soluble Proteins

This invention contemplates methods for targeting expression (e.g., to the periplasm, extracellular medium) of any gene of interest (e.g., to the cytoplasm, extracellular medium) thus reducing the likelihood of expression of insoluble recombinant polypeptides, e.g., in inclusion bodies. The methods of the invention are premised on the discovery of three proteins, MttA1, MttA2, MttB and MttC which function as part of a Sec-independent pathway, and which target expression of twin arginine containing proteins to cell membranes and which direct translocation of such proteins to the periplasm of gram negative bacteria and to the extracellular medium of cells which do not contain a periplasm. This discovery makes possible methods for expression of any gene of interest such that the expressed polypeptide is targeted to the periplasm or extracellular medium thereby allowing its expression in a soluble form and thus facilitating its purification. The methods of the invention contemplate expression of any recombinant polypeptide as a fusion polypeptide with a twin-arginine signal amino acid sequence as the fusion partner. Such expression may be accomplished by introducing a nucleic acid sequence which encodes the fusion polypeptide into a host cell which expresses wild-type MttA1, MttA2, MttB or MttC, or variants or homologs thereof, or which is engineered to express MttA1, MttA2, MttB or MttC, or variants or homologs thereof. While expressly contemplating the use of the methods of the invention for the expression of any polypeptide of interest, the methods disclosed herein are particularly useful for the expression of cofactor-containing proteins. The methods of the invention are further described under (i) Cofactor-containing proteins, (ii) Expression of fusion proteins containing twin-arginine signal amino acid sequences, and (iii) Construction of host cells containing deletions or mutations in at least a portion of the genes mttA1, mttA2, mttB and mttC.

i. Cofactor-containing Proteins

A strong correlation has been reported between possession of a twin-arginine signal amino acid sequence in the preprotein and the presence of a redox cofactor in the mature protein; approximately 40 out of 135 preprotein amino acid sequences which contain a twin-arginine signal amino acid sequence have been found by Berks [Berks (1996) Molecular Microbiology 22 393–104; http://www.blackwell-science.com/products/journals/contents/berks.htm] to result in a mature protein which binds, or can be inferred to bind, a redox cofactor. The entire contents of Berks are hereby expressly incorporated by reference.

The cofactors associated with a twin-arginine signal amino acid sequence include, but are not limited to, iron-sulfur clusters, at least two variants of the molybdopterin cofactor, certain polynuclear copper sites, the tryptophan tryptophylquinone (TTQ) cofactor, and flavin adenine dinucleotide (FAD). A representative selection of bacterial twin-arginine signal amino acid sequences is shown in Table 1.

TABLE 1

|  |  |  | Evidence | Length |
|---|---|---|---|---|
| I. PERIPLASMIC PROTEINS BINDING IRON-SULFUR CLUSTERS | | | | |
| A. MauM family ferredoxins | | | | |
| P. denitrificans | MauM | MEARMTGRRKVTRRDAMADAARAVGVACLG GFSLAALVRTASPVDA SEQ ID NO:50 | VH | 48 |
| E. coli | NapG | MSRSAKPONGRRRFLRDVVRTAGGLAAVGVA LGLQQQTARA SEQ ID NO:51 | VH | 41 |
| B. '16Fe' ferredoxin superfamily | | | | |
| E. coli | NrfC | MTWSRRQFLTGVGVLAAVSGTAGRVVA SEQ ID NO:52 | VH | 27 |
| D. vulgaris | Hmc2 | MDRRRFLTLLGSAGLTATVATAGTAKA SEQ ID NO:53 | VH | 27 |
| C. High potential iron protein (HiPIP) | | | | |
| T. ferrooxidans | Iro | MSEKDKMITRRDALRNIAVVVGSVATTTMMG VGVADA SEQ ID NO:54 | EX | 37 |

TABLE 1-continued

|  |  |  | Evidence | Length |
|---|---|---|---|---|
| D. Periplasmically-located [Fe] hydrogenase small subunits | | | | |
| D. vulgaris | HydB | MQIVNLTRRGFLKAACVVTGGALISIRMTGKA VA SEQ ID NO:55 | VH | 34 |
| E. Periplasmically-located [NiFe] hydrogenase small subunits | | | | |
| E. coli | HyaA | MNNEETFYQAMRRQGVTRRSFLKYCSLAATS LGLGAGMAPKIAWA SEQ ID NO:56 | EX | 45 |
| +M. mazei | VhoG | MSTGTTNLVRTLDSMDFLKMDRRTFMKAVSA LGATAFLGTYQTEIVNA SEQ ID NO:57 | EX | 48 |
| D. gigas | HynB | MKCYIGRGKNQVEERLERRGVSRRDFMKFCT AVAVAMGMGPAFAPKVAEA SEQ ID NO:58 | EX | 50 |
| E. coli | HybA | MNRRNFIKAASCGALLTGALPSVSHA SEQ ID NO:59 | VH | 26 |
| F. Membrane-anchored Rieske proteins | | | | |
| P. denitrificans | FbcF | MSHADEHAGDHGATRRDFLYYATAGAGTVA AGAAAWTLVNQMNP SEQ ID NO:60 | | |
| +Synechocystis | PetC | MTQISGSPDVPDLGRRQFMNLLTFGTITGVAA GALYPAVKYLIP SEQ ID NO:61 | | |
| +S. acidocaldarius | SoxF | MDRRTFLRLYLLVGAAIAVAPVIKPALDYVGY SEQ ID NO:62 | | |
| II. PERIPLASMIC PROTEINS BINDING THE MOLYBDOPTERIN COFACTOR | | | | |
| A. Molybdopterin guanine dinucleotide-binding proteins, some of which also bind an iron-sulfur cluster | | | | |
| R. sphaeroides | DmsA | MTKLSGQELHAELSRRAFLSYTAAVGALGLCG TSLLAQGARA SEQ ID NO:63 | EX | 42 |
| E. coli | BisZ | MTLTRREFIKHSGIAAGALVVTSAAPLPAWA SEQ ID NO:64 | VH | 31 |
| T. pantotropha | NapA | MTISRRDLLKAQAAGIAAMAANIPLSSQAPA SEQ ID NO:65 | VH | 3 1 |
| W. succinogenes | FdhA | MSEALSGRGNDRRKFLKMSALAGVAGVSQAV G SEQ ID NO:66 | EX | 32 |
| E. coli | DmsA | MKTKIPDAVLAAEVSRRGLVKTTAIGGLAMAS SALTLPFSRIAHA SEQ ID NO:67 | EX | 45 |
| H. influenzae | DmsA | MSNFNQISRRDFVKASSAGAALAVSNLTLPFN VMA SEQ ID NO:68 | VH | 35 |
| S. typhimurium | PhsA | MSISRRSFLQGVGIGCSACALGAFPPGALA SEQ ID NO:70 | VH | 30 |
| B. Molybdopterin cytosine dinucleotide-binding proteins | | | | |
| P. diminuta | IorB | MKTVLPSVPETVRLSRRGFLVQAGTITCSVAFG SVPA SEQ ID NO:70 | VH | 37 |
| A. polyoxogenes | Ald | MGRLNRFRLGKDGRREQASLSRRGFLVTSLGA GVMFGFARPSSA SEQ ID NO:71 | EX | 44 |
| III. PERIPLASMIC ENZYMES WITH POLYNUCLEAR COPPER SITES | | | | |
| A. Nitrous oxide reductases | | | | |
| P stutzeri | NosZ | MSDKDSKNTPQVPEKLGLSRRGFLGASAVTGA AVAATALGGAVMTRESWA SEQ ID NO:72 | EX | 50 |
| B. Multicopper oxidase superfamily | | | | |
| P. syringae | CopA | MESRTSRRTEVKGLAAAGVLGGLGLWRSPSW A SEQ ID NO:73 | VH | 32 |
| E. coli | SufI | MSLSRRQFIQASGIALCAGAVPLKASA SEQ ID NO:74 | VH | 27 |
| IV. METHYLAMINE DEHYDROGENASE SMALL SUBUNITS (TRYPTOPHAN TRYPTOPHYLQUINONE COFACTOR) | | | | |
| M. extorquens | MauA | MLGKSQFDDLFEKMSRKVAGHTSRRGFIGRVG TAVAGVALVPLLPVDRRGRVSRANA SEQ ID NO:75 | EX | 57 |
| V. PERIPLASMIC PROTETNS BINDING FLAVIN ADENINE DINUCLEOTIDE | | | | |
| C. vinosum | FccB | MTLNRRDFIKTSGAAVAAVGILGFPHLAFG SEQ ID NO:76 | EX | 30 |
| +B. stericulum | ChoB | MTDSRANRADATRGVASVSRRRFLAGAGLTA GAIALSSMSTSASA SEQ ID NO:77 | EX | 45 |

A more complete listing of bacterial twin-arginine signal amino acid sequences is available at http://www.blackwell-science.com/products/journals/mole.htm, the entire contents of which are incorporated by reference. Amino acids with identity to the most preferred (S/T)-RR-x-F-L-K consensus motif are indicated in bold. Signal sequences are from Proteobacterial preproteins except where indicated (+). 'Evidence' indicates the method used to determine the site of protease processing: EX, experimentally determined; VH, inferred using the algorithm of von Heijne (1987). [1] van der Palen et al. (1995); [2] Richterich et al. (1993); [3] Hussain et al. (1994); [4] Rossi et al. (1993); [5] Kusano et al. (1992); [6] Voordouw et al. (1989); [7] Menon et al. (1990); [8] Deppenmeier et al. (1995); [9] Li et al. (1987); [10] Menon et al. (1994); [11] Kurowski and Ludwig (1987); [12] Mayes and Barber (1991); [13] Castresana et al. (1995); [14] Hilton and Rajagopalan (1996); [15] Campbell and Campbell (1996); [16] Berks et al. (1995a); [17] Bokranz et al. (1991); [18] Bilous et al. (1988); [19] Fleischmann et al. (1995); [20] Heinzinger et al. (1995); [21] Lehmann et al. (1995); [22] Tamaki et al. (1989); [23] Viebrock and Zumft (1988); [24] Mellano and Cooksey (1988); [25] Plunkett (1995); [26] Chistoserdov and Lidstrom (1991); [27] Dolata et al. (1993); [28] Ohta et al. (1991).

In contrast to twin-arginine signal amino acid sequences, Sec signal sequences are associated with periplasmic proteins binding other redox cofactors, i.e., iron porphyrins (including the cytochromes c), mononuclear type I or II copper centers, the dinuclear $CU_A$ center, and the pyrroloquinoline quinone (PQQ) cofactor.

Currently the assembly of cofactor-containing proteins is limited to the cytoplasm because the machinery to insert the cofactor is located in this compartment. The present invention offers the advantage of providing methods for periplasmic and extracellular expression of cofactor-containing proteins which contain a twin-arginine signal amino acid sequence, thus facilitating their purification in a functional and soluble form.

ii. Expression of Fusion Proteins Containing Twin-arginine Signal Amino Acid Sequences The methods of the invention exploit the inventors' discovery of proteins MttA1, MttA2, MttB and MttC which are involved in targeting expression of proteins which contain a twin-arginine amino acid signal sequence to cell membranes and in translocation of such proteins to the periplasm of gram negative bacteria and the extracellular medium of cell that do not contain a periplasm. The term "twin-arginine signal amino acid sequence" as used herein means an amino acid sequence of between 2 and about 200 amino acids, more preferably between about 10 and about 100 amino acids, and most preferably between about 25 and about 60 amino acids, and which comprises the amino acid sequence, from the N-terminal to the C-terminal, A-B-C-D-E-F-G, wherein the amino acid at position B is Arg, and the amino acid at position C is Arg. The amino acid at positions A, D, E, F, and G can be any amino acid. However, the amino acid at position A preferably is Gly, more preferably is Glu, yet more preferably is Thr, and most preferably is Ser. The amino acid at position D preferably is Gln, more preferably is Gly, yet more preferably is Asp, and most preferably is Ser. The amino acid at position E preferably is Leu and more preferably is Phe. The amino acid at position F preferably is Val, more preferably is Met, yet more preferably is Ile, and most preferably is Leu. The amino acid at position G preferably is Gln, more preferably is Gly and most preferably is Lys. In one preferred embodiment, the twin-arginine amino acid signal sequence is Ser-Arg-Arg-Ser-Phe-Leu-Lys (SEQ ID NO:41). In yet another preferred embodiment, the twin-arginine amino acid signal sequence is Thr-Arg-Arg-Ser-Phe-Leu-Lys (SEQ ID NO:42).

The invention contemplates expression of wild-type polypeptide sequences which contain a twin-arginine amino acid signal sequence as part of a preprotein. To date, 135 polypeptide sequences have been reported to contain a twin-arginine amino acid signal sequence motif [Berks (1996) Molecular Microbiology 22 393–104; http://www.blackwell-science.com/products/journals/contents/berks.htm the entire contents of which are incorporated by reference].

The invention further contemplates expression of recombinant polypeptide sequences which are engineered to contain a twin-arginine amino acid signal sequence as part of a fusion protein. Fusion protein containing one or more twin-arginine amino acid signal sequences may be made using methods well known in the art. For example, one of skill in the art knows that nucleic acid sequences which encode a twin-arginine amino acid signal sequence may be operably ligated in frame (directly, or indirectly in the presence of intervening nucleic acid sequences) to a nucleotide sequence which encodes a polypeptide of interest. The ligated nucleotide sequence may then be inserted in an expression vector which is introduced into a host cell for expression of a fusion protein containing the polypeptide of interest and the twin-arginine amino acid signal sequence.

Fusion proteins containing twin-arginine amino acid signal sequences are expected to be targeted to the periplasm or extracellular medium by the MttA1, MttA2, MttB and MttC proteins of the invention and by variants and homologs thereof, Keon and Voordouw [Keon and Voordouw (1996) Anaerobe 2:231–238] have reported that a fusion protein containing *E. coli* alkaline phosphatase (phoA) linked to a signal amino acid sequence from the Hmc complex of *Desulfovibrio vulgaris* subsp. *vulgaris* was exported to *E. coli* periplasm. Similarly, a fusion protein containing a hydrogenase signal peptide to β-lactamase from which the signal peptide had been removed led to export in *E. coli* under both aerobic and anaerobic conditions [Niviere et al. (1992) J. Gen. Microbiol. 138:2173–2183].

Fusion proteins which contain twin-arginine amino acid signal sequences are also expected to be cleaved to generate a mature protein from which the twin-arginine amino acid signal sequences has been cleaved. Two signal peptidases have so far been identified in *E. coli*: Signal peptidase I and signal peptidase II. The signal peptidase II which has a unique cleavage site involving a cystine residue at the cleavage site [Bishop et al. (1995) J. Biol. Chem. 270:23097–23103] is believed not to participate in cleavage of twin-arginine amino acid signal sequences. Rather, signal peptidase I, which cleaves Sec signal sequences has been suggested by Berks to cleave twin-arginine amino acid signal sequences. Berks also suggested that signal peptidase I has the same recognition site in Sec signal sequences as in twin-arginine amino acid signal sequences [Berks (1996)]. This suggestion was based on (a) the "−1/−3" rule for Sec signal peptidase in which the major determinant of signal peptidase processing is the presence of amino acids with small neutral side-chains at positions −1 and −3 relative to the site of cleavage, and (b) the good agreement between the cleavage site of twin-arginine amino acid signal sequences as determined using the "−1/−3" rule (with the invariant arginine at the N-terminus of the signal sequence, i.e., position B in the A-B-C-D-E-F-G sequence, designated as position zero) and the experimentally determined amino terminus of the mature protein [Berks (1996)]. Evidence presented herein (Example 9) further confirms cleavage of twin-arginine amino acid signal sequences to release a mature protein which lacks the twin-arginine amino acid signal sequence.

iii. Construction of Host Cells Containing Deletions or Mutations in at Least a Portion of the Genes mttA, mttB and mttC The function of any portion of *E. coli* MttA1, MttA2, MttB and MttC polypeptides and variants and homologs thereof, as well as the function of any polypeptide which is encoded by a nucleotide sequence that is a variant or homolog of the mttA1, mttA2, mttB and mttC sequences disclosed herein may be demonstrated in any host cell by in vivo homologous recombination of chromosomal sequences which are variants or homologs of mttA1, mttA2, mttB and mttC using previously described methods [Sambasivarao et al (1991) J. Bacteriol. 5935–5943; Jasin et al (1984) J. Bacteriol. 159:783–786]. Briefly, the nucleotide sequence whose function is to be determined is cloned into vectors, and the gene is mutated, e.g., by insertion of a nucleotide sequence within the coding region of the gene. The plasmids are then homologously recombined with chromosomal variants or homologs of mttA1, mttA2, mttB or mttC sequences in order to replace the chromosomal variants or homologs of mttA1, mttA2, mttB or mttC genes with the mutated genes of the vectors. The effect of the mutations on the localization of proteins containing twin-arginine amino acid signal sequences is compared between the wild-type host cells and the cells containing the mutated mttA1, mttA2, mttB or mttC genes. The localization (e.g., cytoplasm, periplasm, cell membranes, extracellular medium) of expressed twin arginine containing proteins is compared using methods disclosed herein (e.g., functional enzyme activity and Western blotting) between homologously recombined cells and control cells which had not been homologously recombined. Localization of expressed twin arginine containing proteins extracellularly, in the periplasm, or in the cytoplasm of homologously recombined cells as compared to localization of expression in cell membranes of control cells demonstrates that the wild-type MttA1, MttA2, MttB or MttC protein whose function had been modified by homologous recombination functions in targeting expression of the twin arginine containing protein to the cell membrane. Similarly, accumulation of expressed twin arginine containing proteins in extracellular medium, in the cytoplasm, or in cell membranes of homologously recombined cells as compared to periplasmic localization of the expressed twin arginine containing protein in control cells which had not been homologously recombined indicates that the protein (i.e., MttA1, MttA2, MttB or MttC) whose function had been modified by homologous recombination functions in translocation of the twin arginine containing protein to the periplasm.

Experimental

The following examples serve to illustrate certain preferred embodiments and aspects of the present invention and are not to be construed as limiting the scope thereof. The strains and plasmids used in this investigation are listed in Table 2.

TABLE 2

Bacteria and Plasmids used in this Investigation

| Strain/Plasmid | Genotype or Gene Combinations Present | Reference/Source |
| --- | --- | --- |
| HB101 | F-, hsdS20(r$_B$m$_B$), leu, supE44, ara14, galK2, lacY1, proA2, rpsL20, xyl-5, mtl-1, recA13, mcrB | Boyer and Roulland-Dussoix, 1969 |
| TG1 | K12Δ(lac-pro) sup EF' traD36 proAB lacI$^q$ ΔlacZM15 | Amersham Corp. |
| D43 | HB101; mttA | Bilous and Weiner, 1985 |
| pBR322 | cloning vector Tet$^r$, Amp$^r$ | Pharmacia |
| pTZ18R | cloning vector Amp$^r$, lacZ | Pharmacia |
| pJBS633 | blaM fusion vector | Broome-Smith and Spratt, 1986 |
| pFRD84 | frdABCD cloned into pBR322 | Lemire et al., 1982 |
| pFRD117 | ΔfrdCD version of pFRD84 | Lemire et al., 1982 |
| pDMS160 | dmsABC cloned into pBR322 | Rothery and Weiner, 1991 |
| pDMS223 | dmsABC operon in pTZ18R | Rothery and Weiner, 1991 |
| pDMSL71 | dmsABC::blaM in pJBS633 fusion after residue 12 | Weiner et al., 1993 |
| pDMSL5 | dmsABC::blaM in pJBS633 fusion after residue 216 | Weiner et al., 1993 |
| pDMSL29 | dmsABC::blaM in pJBS633 fusion after residue 229 | Weiner et al., 1993 |
| pDMSL4 | dmsABC::blaM in pJBS633 frsion after residue 267 | Weiner et al., 1993 |

TABLE 2-continued

Bacteria and Plasmids used in this Investigation

| Strain/Plasmid | Genotype or Gene Combinations Present | Reference/Source |
| --- | --- | --- |
| pDMSC59X | dmsC truncate after residue 59 | Sambasivarao and Weiner, 1991 |
| pDSR311 | yigO, P, R, T and U in pBR322 | This investigation |
| pGS20 | b3835', b3836, b3837, and b3838' in pBR322 | This investigation |
| pTZmttABC | region of ORF's b3836, b3838, yigU, yigW, cloned into pTZ18R | This investigation |
| pBRmttABC | region of ORF's b3836, b3838, yigU, yigW, cloned into pBR322 | This investigation |
| pTZb3836 | ORF b3836 cloned into pTZ18R | This investigation |
| pBRb3836 | ORF b3836 cloned into pBR322 | This investigation |

EXAMPLE 1

Isolation and Properties of D-43 Mutants Defective in DmsABC Targeting

DMSO reductase is a "twin arginine" trimeric enzyme composed of an extrinsic membrane dimer with catalytic, DmsA, and electron transfer, DmsB, subunits bound to an intrinsic anchor subunit, DmsC. The DmsA subunit has a "twin arginine" leader but it has been exhaustively shown that the DmsA and DmsB subunits face the cytoplasm [Rothery and Weiner (1996) Biochem. 35:3247–3257; Rothery and Weiner (1993) Biochem. 32:5855–5861; Sambasivarao et al. (1990) J. Bacteriol. 172:5938–5948; Weiner et al. (1992) Biochem. Biophys. Acta 1102:1–18; Weiner et al. (1993) J. Biol. Chem. 268:3238–3244].

In order to isolate a E. Coli mutant defective in membrane targeting of DmsABC, plieotropic mutants which were unable to grow on DMSO were produced by nitrosoguanidine mutagenesis of HB101 and the growth rates on DMSO of both the mutants and HB101 were determined. Mutant D-43, which grew anaerobically on fumarate and nitrate, nevertheless failed to grow on DMSO or TMAO. These results are further described in the following sections.

A. Isolation of Mutant

Nitrosoguanidine mutagenesis and ampicillin enrichment were as described by Miller (1992) in A Short Course in Bacterial Genetics, Cold Spring Harbor Laboratory Press. Sixteen mutants were isolated that were defective for anaerobic growth on DMSO but grew with nitrate or fumarate as the alternate electron acceptor. Each of the mutants was transformed with pDMS160 [Rothery and Weiner (1991) Biochem. 30:8296–8305] carrying the entire dms operon and again tested for growth on DMSO. All of the transformants failed to grow on DMSO. When tested for DMSO reductase activity 14 of the 16 transformants lacked measurable enzyme activity. Two of the mutants expressed high levels of DMSO reductase activity but the activity was localized in the cytoplasm rather than the membrane fraction. One of these mutants, D-43, was chosen for further study.

B. Anaerobic Growth Rates of HB101 and D-43

For growth experiments, bacteria were initially grown aerobically overnight at 37° C. in LB plus 10 μg/ml$^{-1}$ vitamin B1. A 1% inoculum was added to 150 ml of minimal salts medium containing 0.8% (w/v) glycerol, 10 μg/ml$^{-1}$ each of proline, leucine, vitamin B1 and 0.15% peptone and supplemented with either DMSO 70 mM, fumarate 35 mM, nitrate 40 mM, or trimethylamine N-oxide (TMAO) 100 mM. Cultures were grown anaerobically at 37° C. in Klett flasks and the turbidity monitored in a Klett spectrophotometer with a No. 66 filter.

The rates of anaerobic growth of strains HB101 and D-43 with a range of electron acceptors and a nonfermentable carbon source, glycerol, were compared. The results are shown in FIGS. 1A and 1B.

Figure 1B:
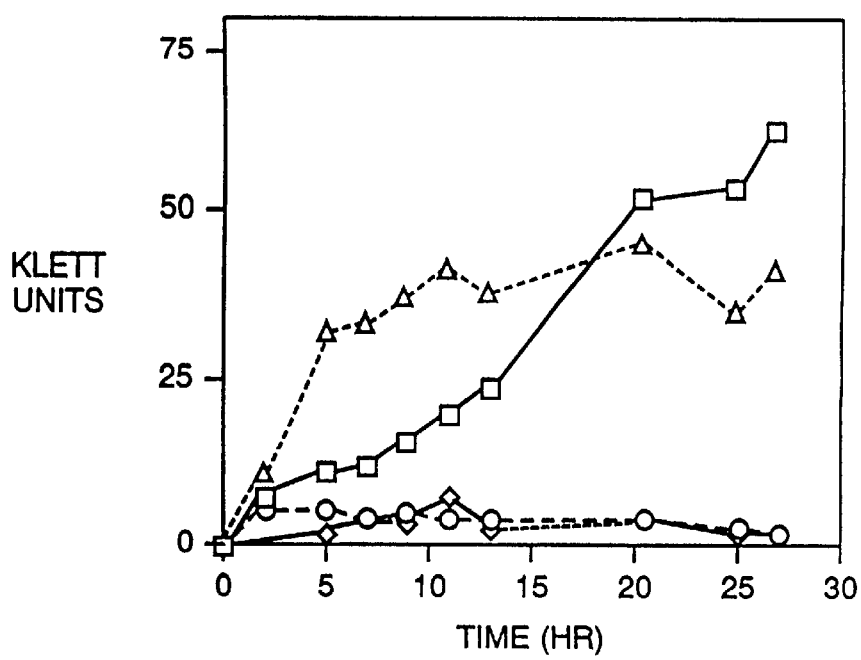

All the terminal electron acceptors tested supported the growth of the parent HB101 (FIG. 1a). In contrast, only nitrate and fumarate stimulated the growth rate of the mutant (FIG. 1b). However, even in the presence of nitrate and fumarate the growth yield was half that of strain HB101. The reduced growth rate may reflect the pleiotropic effects of the mutation of various metabolic reactions needed for optimal growth in addition to the terminal electron transfer reaction. Only DmsABC supports growth on DMSO whereas both DmsABC and the periplasmic TMAO reductase support growth on TMAO [Sambasivarao and Weiner (1991) J. Bacteriol. 173:5935–5943]. The observation that D-43 is unable to grow on either DMSO or TMAO indicates that both of these enzymes were non-functional.

EXAMPLE 2

DmsA is not Anchored to the Membrane in D-43

Previous studies have exhaustively shown that DmsABC is localized on the cytoplasmic membrane of wild-type *E. coli* strains with the DmsAB subunits anchored to the cytoplasmic surface [Rothery and Weiner (1996) Biochem. 35:3247–3257; Rothery and Weiner (1993) Biochem. 32:5855–5861; Sambasivarao et al. (1990) J. Bacteriol. 172:5938–5948; Weiner et al. (1992) Biochem. Biophys. Acta 1102:1–18; Weiner et al. (1993) J. Biol. Chem. 268:3238–3244]. In order to determine he localization of DmsABC in D-43 mutants, cell fractions were assayed for the presence of DmsA and DmsB by immunoblot analysis, and for DMSO reductase activity as follows.

A. Functional Enzyme Activity Assays

Cell fractions were assayed for DMSO reductase activity by measuring the DMSO-dependent oxidation of reduced benzyl viologen at 23° C. [Bilous and Weiner (1985) J. Bacteriol. 162:1151–1155]. This assay is dependent only on the presence of DmsAB.

To test the localization of DmsABC in D-43, enzyme activity in the soluble fraction and membrane band fraction of HB101/pDMS160 and of D-43/pDMS160 was determined. 250 ml anaerobic cultures of HB101/pDMS160 and D-43/pDMS160 were grown on Gly/Fum medium. HB101/pDMS160 yielded 114 mg total protein, 3240 units of membrane-bound TMAO reductase activity, and 2900 units of soluble activity. D-43/pDMS160 yielded 99 mg total protein, 320 units were membrane-bound and 4000 units were soluble. Thus, although the total DmsABC activity was lower in D-43, (4300 total units compared to 6200 for HB101/pDMS160) the vast majority was not targeted to the membrane. This suggested that D-43 was defective in targeting to the membrane rather than in a biosynthetic step.

B. Western Blot Analysis of DmsA and DmsB

To determine the cellular locations of DmsA and DmsB by Western blots, D-43/pDMS160 and HB101/pDMS160 were grown anaerobically on Gly/fumarate medium at 37° C. in 19 l batches [Bilous and Weiner (1985) J. Bacteriol. 162:1151–1155]. Cultures were grown for 24 hr, at 37° C. and the cells harvested and membranes prepared by French pressure cell lysis at 16,000 psi followed by differential centrifugation as previously described [Rothery and Weiner (1991) Biochem. 30:8296–8305]. The crude membranes were washed twice with lysis buffer (50 mM MOPS, 5 mM EDTA pH 7.0). DmsABC was purified as described by Simala-Grant and Weiner (1996) Microbiology 142:3231–3229. For the determination of subunit anchoring to the membrane, membrane preparations were first washed with lysis buffer and then with lysis buffer containing 1 M NaCl. The osmotic shock procedure of Weiner and Heppel (1971) J. Biol. Chem. 246:6933–6941) was used to isolate the periplasmic fraction tested for fumarate and DMSO reductase polypeptides.

For Western blot analysis, antibodies to purified DmsA and DmsB were used [Sambasivarao et al. (1990) J. Bacteriol. 172:5938–5948]. Typically, samples were separated on 10% (w/v) SDS-PAGE and then blotted onto nitrocellulose. The protein bands were detected using the enhanced chemiluminescence detection system from Amersham and goat anti-rabbit IgG (H+L) horseradish peroxidase conjugate. The results are shown in FIG. 2.

Figure 2:
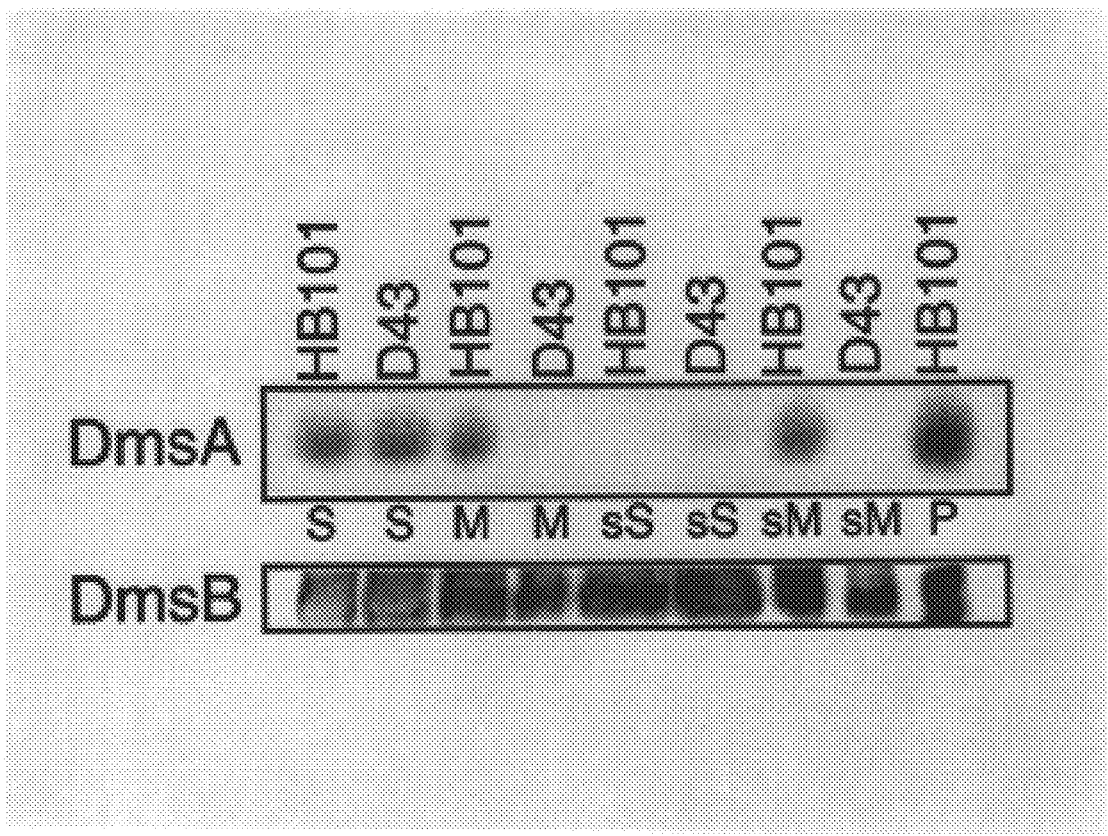
FIG. 2 shows a Western blot analysis of washed membranes and soluble fractions of HB101 and D-43 harboring pDMS160 expressing DmsABC.

FIG. 2 shows a Western blot of washed membranes and soluble fractions of HB101 and D-43 harboring pDMS160 expressing DmsABC. The blot was probed with either purified anti-DmsA or anti-DmsB. S; soluble fraction, M; Washed membranes, sM; salt washed membranes, sS; soluble fraction from the salt washed membranes, P; purified DmsABC. FIG. 2 clearly shows that DmsA is not targeted to the membrane in D-43. The DmsA polypeptide was expressed and was present in the cytoplasm at levels equivalent to the wild-type. Equivalent samples probed with anti-DmsB demonstrated that significant amounts of DmsB were targeted to the membrane. Membrane incorporation of DmsC in the absence of DmsAB is lethal [Turner et al. (1997) Prof. Engineering 10:285–290] and the presence of DmsB on the membrane may overcome the lethality normally associated with incorporation of DmsC in the absence of the catalytic subunits.

EXAMPLE 3

DmsC is Anchored to the Membrane in D-43

Because polyclonal antibodies against DmsC could not successfully be raised [Sambasivarao et al. (1990) J. Bacteriol. 172:5938–5948; Turner et al. (1997) Prof. Engineering 10:285–290], three BlaM (β-lactamase) fusions were used to determine whether the anchor subunit is translated and correctly inserted into the membranes of D-43 [Weiner et al. (1993) J. Biol. Chem. 268:3238–3244]. These fusions were located after amino acid positions 216, 229 and 267 of DmsC. Fusion 216 was localized to the periplasm and mediated very high resistance. Fusions 229 and 267 were localized to the seventh and eighth transmembrane helices and mediated intermediate levels of resistance [Weiner et al. (1993) J. Biol. Chem. 268:3238–3244]. The minimal inhibitory concentrations of ampicillin, for each of these fusions expressed in D-43 under anaerobic growth conditions, were the same or within one plate dilution of the wild-type values. Additionally, Western blots, using antibody directed against BlaM, of cell fractions of membrane, cytoplasmic and osmotic shock fluids of D-43/pDMSL29 (fusion at amino acid 229) showed DmsC-BlaM in the membrane fractions (results not shown). These data suggest that the DmsC protein is translated and inserted into the membrane and has the same topology as that found in wild-type *E. coli* cells.

EXAMPLE 4

Enzyme Activity of Nitrate Reductase and Trimethylamine N-Oxide Reductase with a Twin Arginine Signal Sequence is not Targeted to the Periplasm of D-43 While Enzyme Activity of Nitrite Reductase with a Sec-Signal Sequence is Present in the Periplasm of D-43

In order to determine whether the mutation in D-43 (which resulted in failure to anchor DmsA and DmsB to the cell membrane as described above) selectively prevented membrane targeting of proteins with a twin-arginine signal amino acid sequence, the enzyme activity of periplasmic enzymes having a twin-arginine signal amino acid sequence (i.e., nitrate reductase (NapA) and trimethylamine N-oxide reductase (TorA)) and of a periplasmic enzyme having a Sec-leader sequence (i.e., nitrite reductase (NrfA)) was determined in the periplasm of D-43 and HB101.

*E. coli* can reduce nitrate to ammonia using two periplasmic electron transfer chains, the Nap and Nrf pathways [Grove et al. (1996) Mol. Microbiol. 19:467–481; Cole (1996) FEMS Microbiol. Letts. 136:1–11]. The catalytic subunit of the periplasmic nitrate reductase, NapA, is a large molybdoprotein with similarity to DmsA and is synthesized with a twin-arginine signal amino acid sequence. NrfA, the periplasmic nitrite reductase, is not a molybdoprotein but a c-type cytochrome and contains a Sec-leader peptide. Accumulation of both of these redox enzymes in the periplasm of strain D-43 was assayed by staining the periplasmic proteins separated by PAGE with reduced methyl viologen in the presence of nitrate and nitrite as follows.

Periplasmic proteins were released from washed bacterial suspensions as described by McEwan et al. (1984) Arch. Microbiol. 137:344–349 except that the EDTA concentration was 5 mM. The periplasmic fraction was dialyzed against two changes of a 20-fold excess of 10 mM Na+/K+ phosphate, pH 7.4 to remove sucrose and excess salt, freeze dried and dissolved in 10 mM phosphate pH 7.4 to a protein concentration of about 15 mg/ml$^{-1}$. Protein concentrations were determined by the Folin phenol method described previously [Newman and Cole (1978) J. Gen. Microbiol. 106:1–12]. The periplasmic proteins were separated on a 7.5% non-denaturing polyacrylamide gel. After electrophoresis, the 18 cm square gel was immersed in 5 $\mu$g ml$^{-1}$ methyl viologen containing 5 mM nitrate. Dithionite was added to keep the viologen reduced; bands of activity were detected as transparent areas against a dark purple background. The same protocol was used to detect periplasmic nitrite and TMAO reductase activity but 5 mM nitrate was replaced by 2.5 mM nitrite or 5 mM TMAO, respectively. The results are shown in FIGS. 3A, 3B, and 3C.

Figure 3:
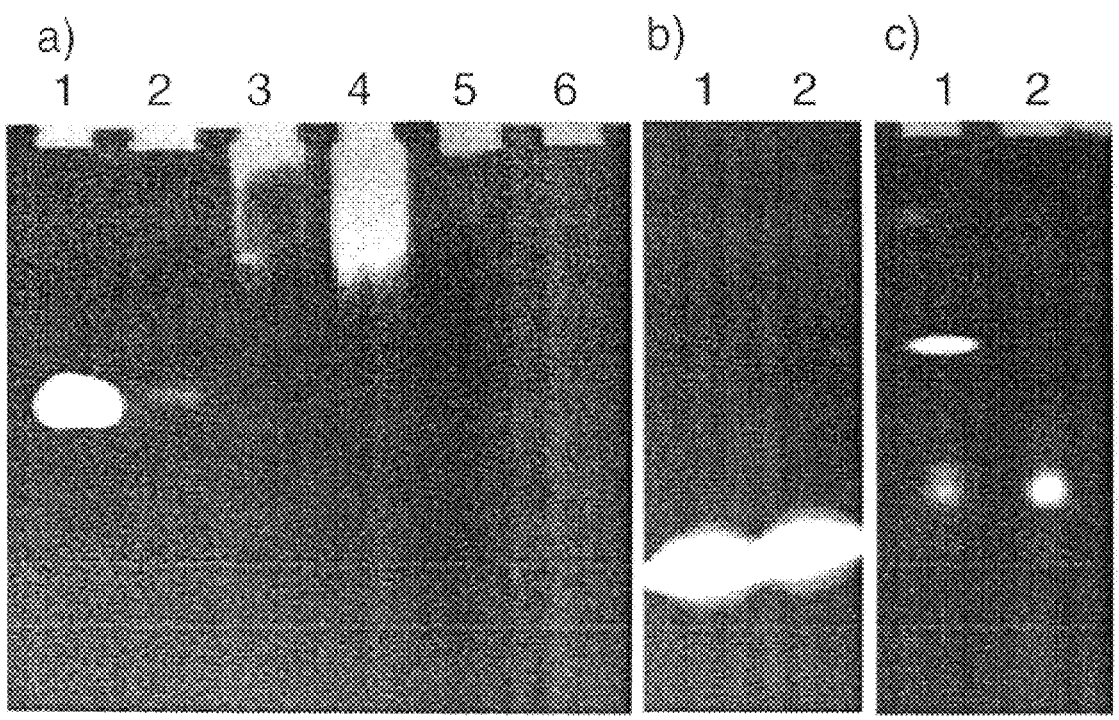
FIG. 3A shows a nitrate-stained polyacrylamide gel containing periplasmic proteins, membrane proteins and cytoplasmic proteins from HB101 and D-43.
FIG. 3B shows a nitrate-stained polyacrylamide gel containing periplasmic proteins from HB101 and D-43.
FIG. 3C shows a TMAO-stained polyacrylamide gel containing periplasmic proteins from HB101 and D-43.

FIG. 3A shows A nitrate-stained polyacrylamide gel containing periplasmic proteins, membrane proteins and cytoplasmic proteins from HB101 and D-43. Lanes 1) and 2) contain periplasmic proteins from HB101 and D-43, respectively. Lanes 3) and 4) contain membrane proteins from HB101 and D-43, respectively and lanes 5) and 6) contain soluble cytoplasmic proteins from HB101 and D-43, respectively. FIG. 3B shows nitrite-stained polyacrylamide gel containing periplasmic proteins from 1) HB101 and 2) D-43. Approximately 30 $\mu$g of protein was loaded into each lane. FIG. 3C shows TMAO-stained polyacrylamide gel containing periplasmic proteins from 1) HB101 and 2) D-43.

The results in FIGS. 3A, 3B, and 3C show that nitrate reductase activity due to NapA was present in the periplasmic proteins extracted from the parental strain HB101 but was not observed in periplasmic proteins prepared from strain D-43 (FIG. 3A). In contrast, activity of NrfA, the c-type cytochrome nitrite reductase, was similar in periplasmic proteins prepared from both HB101 and D-43 (FIG. 3B). Significantly, the nitrate reductase activity was higher in membranes prepared from strain D-43 than in membranes prepared from the parental strain HB101, suggesting that NapA protein was "stuck" in the membrane fraction. No nitrate reductase activity was detected in soluble cytoplasmic proteins prepared from either strain (data not shown).

Additionally, the rate of electron transfer from physiologic electron donors to NrfA was measured by assaying the rate of nitrite reduction by a suspension of whole cells in the presence of formate or glycerol. The effects of the mutation on periplasmic nitrite reductase activity provided a key control to test whether MttA2 plays a major role in protein targeting. Nrf activity can be assessed in two ways: by detecting the activity of the terminal nitrite reductase which is a c-type cytochrome secreted by the Sec pathway and assembled in the periplasm (FIG. 3B) [Thony-Meyer and Kunzler (1997) Eur. J. Biochem. 246:794–799], and by measuring the rate of nitrite reduction by washed bacteria in the presence of the physiologic substrate, formate. Only the latter activity requires the membrane-bound iron-sulfur protein, NrfC, which is synthesized with an N-terminal twin-arginine signal amino acid sequence.

The rate of nitrite reduction in suspensions of strain HB101 was 34 $\mu$mol nitrite reduced/min$^{-1}$/ml$^{-1}$ while that measured with suspensions of D-43 was 11 $\mu$mol nitrite reduced/min$^{-1}$/ml$^{-1}$. These results show that cytochrome $c_{552}$ was correctly targeted in the mutant and able to catalyse nitrite reduction with dithionite-reduced methyl viologen as the artificial electron donor, but strain D-43 was deficient in formate-dependent nitrite reductase activity.

Loss of electron transport to NrfA from physiologic electron donors, but not from reduced methyl viologen was probably due to the presence of a twin-arginine signal amino acid sequence motif in either NrfC, which is a protein essential for the transfer of electrons from quinones to NrfA [Hussain et al. (1996) Mol. Microbiol. 12:153–163] or in FdnG which contributes to the transfer of electrons from formate to nitrite [Darwin et al. (1993) J. Gen. Microbiol. 139:1829–1840].

Trimethylamine N-oxide reductase (TorA) is another periplasmic terminal reductase related to DmsA [Mejean et al. (1994) Mol. Microbiol. 11:1169–1179] which contains a twin-arginine signal amino acid sequence. In strain D-43 this enzyme activity was not observed in the periplasmic protein fraction (FIG. 3c).

EXAMPLE 5

MttA Protein Targets DmsAB to the Membrane and Does not Translocate DmsAB to the Periplasm In order to determine whether MttA2 is involved in targeting DmsAB to the membrane rather than in the translocation of DmsAB to the periplasm, and whether the role of DmsC is to prevent translocation of DmsAB to the periplasm, the intracellular location was examined in HB101 and D-43 for the DmsA and DmsB subunits expressed from a plasmid encoding the wild-type DmsABC operon as well as a truncated form lacking the anchor subunit DmsC. The results are shown in FIGS. 4A and 4B.

Figure 4:
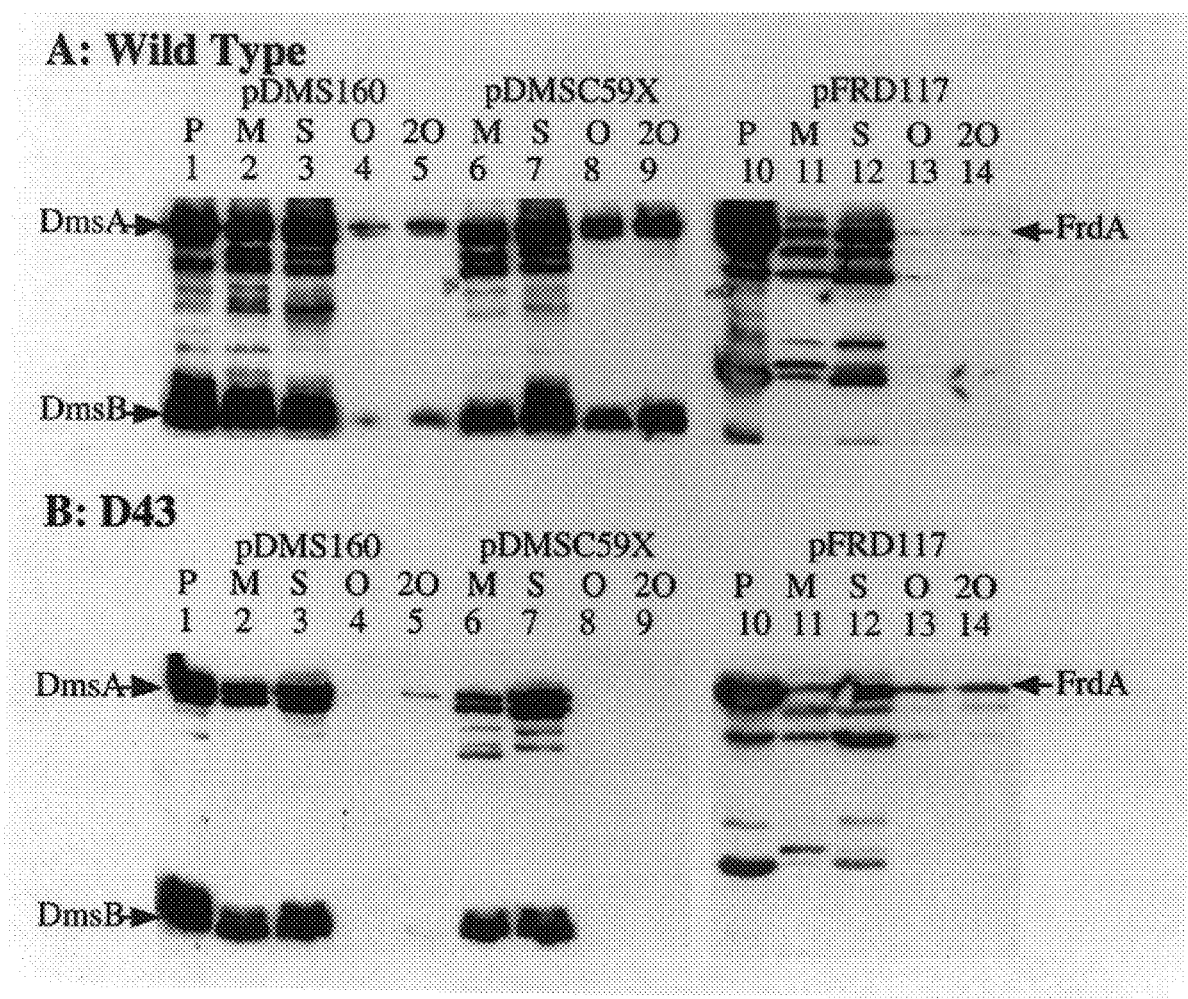
FIGS. 4A and 4B show the results of a Western blot analysis of the cellular localization of DmsAB in (FIG. 4A) HB101 expressing either native DmsABC (pDMS160), DmsABΔC (pDMSC59X), or FrdABΔCD, and (FIG. 4B) equivalent lanes as in FIG. 4A, but with the same plasmids in D-43.

FIGS. 4A and 4B show a Western blots of DmsAB. FIG. 4A shows HB101 expressing either native DmsABC (pDMS160), DmsABΔC (pDMSC59X), or FrdABΔCD. FIG. 4B shows equivalent lanes as in FIG. 4A, with the same plasmids in D-43. P; purified or enriched sample protein of either DmsABC or FrdAB, M; washed membranes, S; soluble fraction, O; osmotic shock fraction, 2O; 2 fold osmotic shock fraction. Purified FrdAB was obtained from HB101/pFRD84 expressing high levels of the wild-type enzyme and purified by the method of [Dickie and Weiner (1979) Can. J. Biochem. 57:813–821; Lemire and Weiner (1986) Meth. Enzymol. 126:377–386]. All lanes had the equivalent concentration of protein loaded.

As shown in FIG. 4A, (compare lanes 8 and 9 to lanes 4 and 5) significant amounts of DmsA and DmsB accumulated in the periplasm only when the DmsC subunit was absent. As a control for this experiment, plasmids carrying the intact frdABCD (pFRD84) (not shown) and truncated frdAB (pFRD117) [Lemire et al. (1982) J. Bacteriol. 152:1126–1131] lacking the anchor subunits of fumarate reductase were also expressed. As fumarate reductase does not have a twin-arginine signal amino acid sequence and assembles spontaneously in the membrane [Latour and Weiner (1987) J. Gen. Microbiol. 133:597–607] neither a Mtt mutation, nor loss of the anchor subunits, FrdC and FrdD, should result in secretion of FrdAB into the periplasm. This was confirmed (lanes 13 and 14). In FIG. 4B the same experiment is shown for strain D-43. As expected neither DmsA nor DmsB accumulated in the periplasm.

These results demonstrate that MttA is not involved in the translocation of DmsAB to the periplasm but in targeting them to the membrane. These results also suggest that the role of DmsC is to prevent translocation of DmsAB to the periplasm.

EXAMPLE 6

Plasmid Complementation of D-43 and Sequencing of the mttA Region

Complementation of the D-43 mutant with plasmid pDMS160 (which carries the wild-type DmsABC operon) was carried out to determine whether the mutation was located within or outside the DmsABC structural gene.

A. Plasmid Complementation of Mutant D-43

For initial complementation experiments, an *E. coli* DNA library was prepared by HindIII digestion of an *E. coli* HB101 chromosomal DNA preparation and ligated into the HindII site of pBR322. The ligation mixture was transformed directly into D-43. The transformants were grown anaerobically on glycerol/DMSO (Gly/DMSO) plates and incubated anaerobically at 37° C. for 72 hr. The complementing clone identified form this library, pDSR311, was isolated and restriction mapped. The map was compared with the integrated *E. coli* restriction map version 6 [Berlyn et al. (1996) Edition 9 in *Escherichia coli* and *Salmonella* 2:1715–1902, ASM Press, Washington D.C].

A second gene bank was prepared using random 5–7 kb Sau3a fragments of *E. coli* W1485 ligated into the BamHI site of pBR322. This *E. coli* gene bank was a gift from Dr. P. Miller, Parke-Davis Pharmaceuticals, Ann Arbor, Mich. D-43 was transformed with 2 μg of this library and transformants were plated onto Luria-Bertani (LB) broth plates containing 100 μg/ml$^{-1}$ ampicillin. After overnight growth at 37° C. the cells were washed off the plates into 5 ml of LB broth and 20 μl of this suspension was diluted with 10 ml of Minimal A medium [Miller (1992) in *A Short Course in Bacterial Genetics*, Cold Spring Harbor Laboratory Press] containing 100 μg/ml$^-$ampicillin and 10 μg/ml$^{-1}$ vitamin B1, proline and leucine and grown aerobically at 37° C. for 16 hr. The cells were washed twice in phosphate buffered saline (PBS) and samples were serially diluted into PBS buffer. Each dilution (100 μl) was plated on Gly/DMSO plates and incubated anaerobically at 37° C. for 72 hr. Colonies were further tested for anaerobic growth in 9 ml screw-top test tubes containing Gly/DMSO broth medium.

The location of the complementing clones in the *E. coli* chromosome obtained from both libraries was confirmed by DNA sequencing the ends of the clones using primers which flanked the HindIII and BamHI sites of pBR322. Subclones of the complementing clones from each of the libraries were constructed utilizing standard cloning methods [Sambrook et al. (1989)] and ligated into the cloning vector pTZ18R. DNA from subclones was restriction mapped to verify the insert. Positive subclones were tested for anaerobic growth in Gly/DMSO and Gly/Fumarate broth medium.

Figure 5:
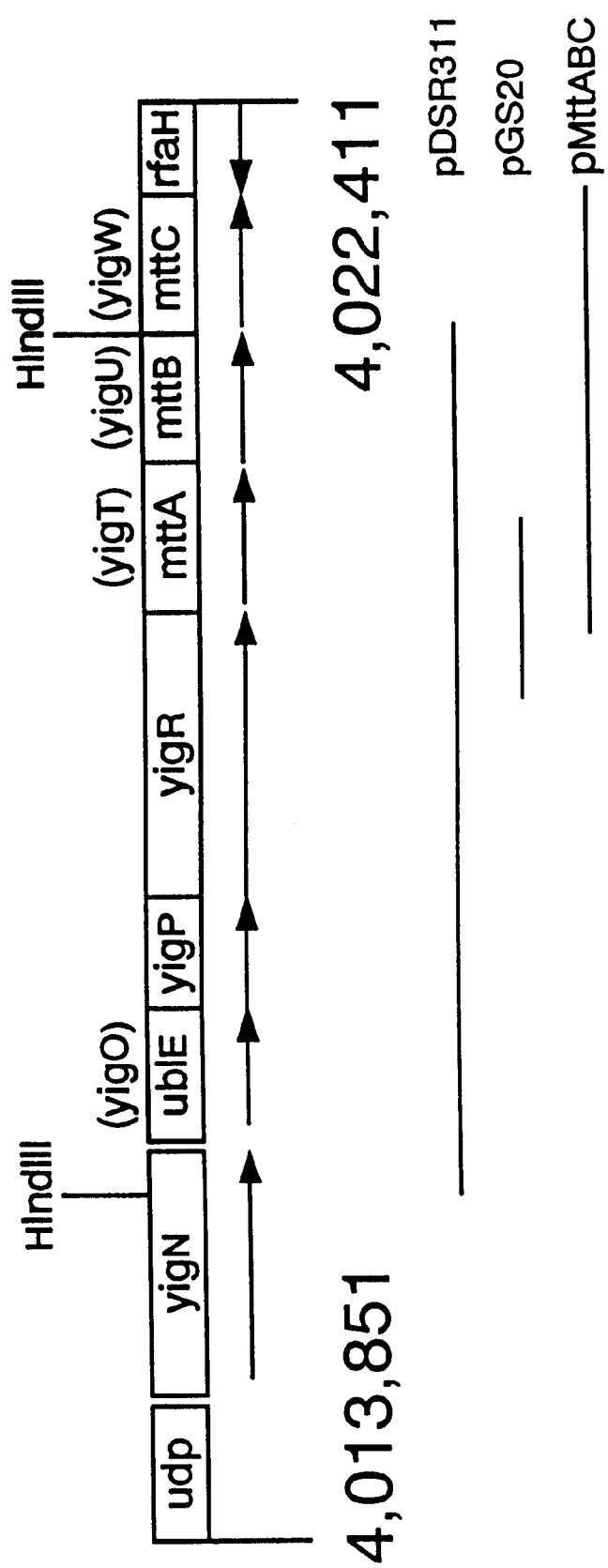
FIG. 5 shows a gene map of contig AE00459 noting the positions of the ORFs and the clones used in this investigation.

A single clone, pDSR311, which allowed growth on Gly/DMSO was identified. Through restriction map analysis and sequencing the ends of the insert, the clone was mapped to the 88 min region of the chromosome, within contig AE00459 covering the 4,013,851–4,022,411 bp region of the sequence of Blattner et al. [Blattner et al. (1997) Science 277:1453–1462]. The clone contained the previously undefined open reading frames yigO, P, R, T, and U (based on the original yig nomenclature for unidentified ORFs) (FIG. 5).

All attempts to use available restriction sites to subclone this region into ORF groups yigOP, yigR, yigRTU, and yigTU were unsuccessful. Therefore, a second library consisting of *E. coli* chromosomal DNA which had been partially-digested with Sau3a was ligated into BamHI-digested pB322. This library generated a number of complementing clones. The smallest was pGS20 which encoded the 3' end of yigR and approximately three quarters of yigT as shown in FIG. 5. This suggested that the products of the putative genes yigTUW were responsible for DmsA targeting to the membrane and Nap translocation to the periplasm and these genes were renamed mttABC (membrane targeting and translocation). This region was cloned from wild-type HB101 utilizing PCR as follows.

For PCR cloning of the mttABC region, the chromosomal DNA template for PCR was prepared from HB101. Bacteria from 1.5 ml of an overnight culture were pelleted in an Eppendorf tube and resuspended in 100 μl of water. The cells were frozen and thawed three times, pelleted by centrifugation and 5 μl of the supernatant was used as the PCR template.

The region of the putative mttABC operon was cloned utilizing PCR. The 5' primer was located at the end of the coding sequence for yigR(b3835) (position 5559–5573 of contig AE00459) and included the intervening sequence between yigR and mttA. The 3' primer hybridized immediately after the stop codon of mttC (position 8090–8110). The primers contained the restriction sites EcoRI and Sail to facilitate cloning into the phagemid pTZ18R and recombinants were screened in *E. coli* strain TGI. The ends of the clones were sequenced to verify the region cloned.

Clones of the ORF region mttABC were subcloned utilizing standard cloning methods [Sambrook et al. (1989)] and ligated into the vector pB322. Positive clones and subclones were transformed into D-43 and tested for anaerobic growth in Gly/DMSO and Gly/Fumarate broth medium.

The clone of mttABC was able to complement the D-43 mutation only when cloned into the lower copy number plasmid pB322 (pBRmttABC) and no complementation (or growth) was observed when mttABC was cloned into the high copy number plasmid pTZ18R (pTZmttABC).

The D-43 mutant could not be complemented with plasmid pDMS160 carrying the wild-type DmsABC operon suggesting that the mutation mapped outside the structural genes. Interestingly, the mutant expressed nearly normal levels of DMSO reductase activity but the activity was soluble rather than membrane-bound. This was surprising given that the membrane anchor, DmsC, was expressed in these cells (see below) and this suggested that the mutant was defective in membrane targeting or assembly.

B. Sequencing the mttA Region

We compared the sequence of clone pGS20 with the identical region of strain D-43 by PCR sequencing of both strands as follows. Chromosomal DNA from strains HB101 and D-43 was prepared as above. The 976 bp region which complements the D-43 mutation was amplified, the PCR products were sequenced directly and the DNA sequences of both strains were compared to the published sequence of *E. coli* [Blattner et al. (1997)]. As Taq DNA polymerase was used for PCR, two different reaction products, resulting from separately prepared templates, were sequenced to identify any mutations which may have resulted from the PCR reaction. Both strands were sequenced in the region of any identified mutations.

We identified only one nucleotide change altering a C to a T at position 743 of pGS20. When this region was compared to the sequence of contig AE00459 in the *E. coli* genome sequence [Blattner et al. (1997) Science 277:1453–1462], it appeared that the mutation mapped within the proposed ORF termed b3837. This ORF did not have a normal *E. coli* codon usage and so we determined the DNA sequence of this region of AE00459. Several differences were identified and a revised ORF map of this contig is shown in FIG. 5. This revision resulted in several changes: ORF b3836, b3837 and b3838 are no longer observed and are replaced by a polypeptide which is very similar throughout its length to the YigT protein of *H.influenzae* [Fleischmann et al. (1995) Science 269:496–512] (FIGS. 6A and 6B).

Figure 6A:
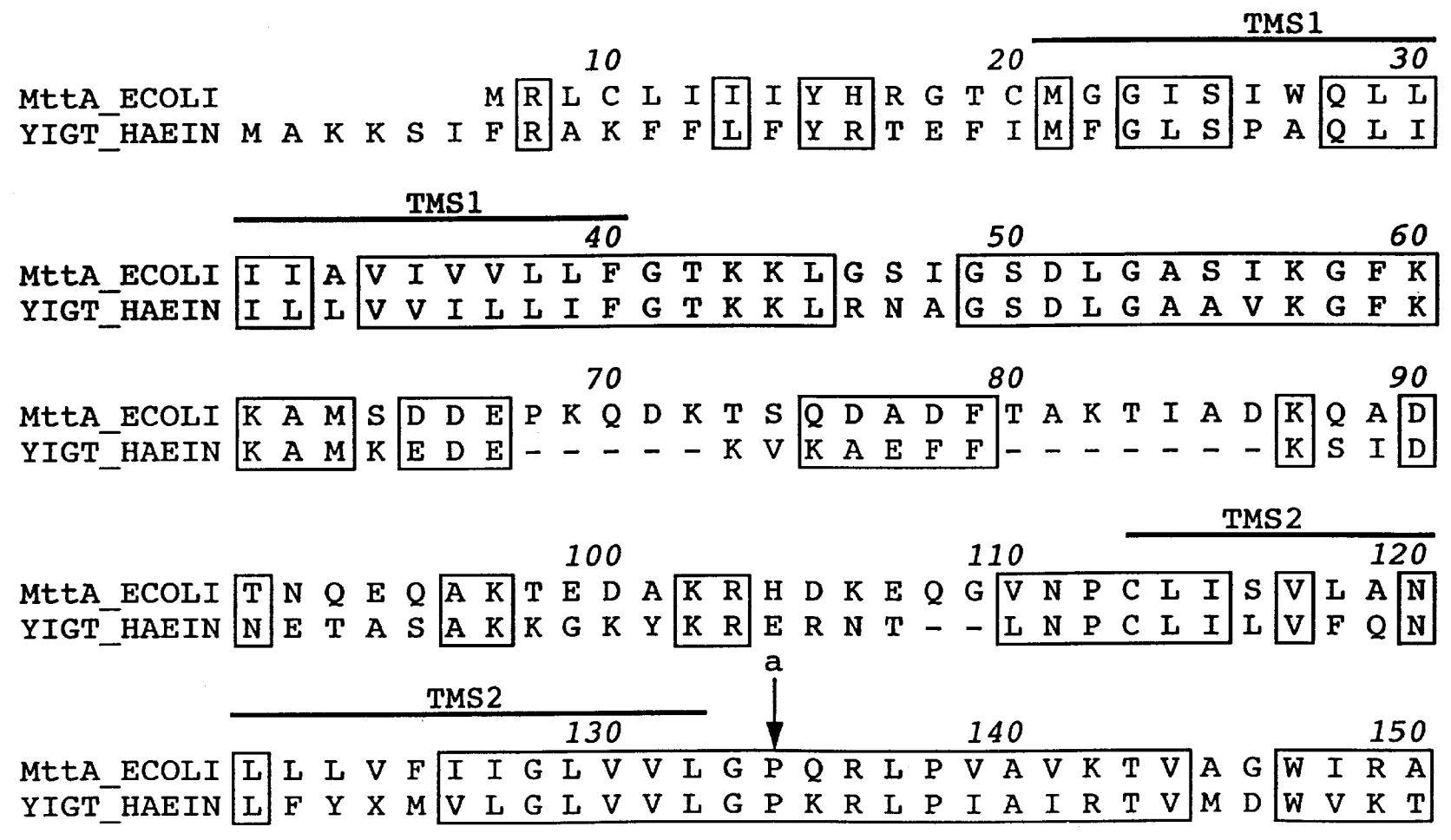

FIGS. 6A and 6B show the sequence (SEQ ID NO:1) of *E. coli* wild-type MttA aligned with YigT of *Haemophilus influenzae* (Fleischmann et al., 1995) (SEQ ID NO:2). The two potential transmembrane segments are denoted as TMS1 and TMS2, respectively. a) denotes the position of the mutation in which changes proline 25 to leucine. b) denotes the termination of MttA in clone pGS20. The potential α-helical region is indicated.

The mutation in D-43 resulted in the mutation of proline 128 of MttA2 to leucine. Interestingly, clone pGS20 did not encode the entire MttA polypeptide but terminated at amino acid 205. The MttA protein is composed of 277 amino acids and has a mass of –30.6 kDa. Without limiting the invention to any particular mechanism, the MttA protein has two potential transmembrane helices between residues 15–34 and 107–126. The most likely orientation is with the amino and carboxyl termini exposed to the periplasm. Residues 150 to 200 are predicted to form a very long α-helix. The mutation in D-43 altered the proline immediately after the second transmembrane helix and could disrupt this structure of the protein.

C. Proteins Homologous to the MttA Protein

A database search of sequences which are related to mttA (i.e., mttA1 and mttA2) identified a large family of related proteins whose function was previously unknown. In addition to the *Zea mays* protein of Settles et al. (1997) Science 278:1467–1470, related sequences were identified by BLAST searches in *Azotobacter chroococcum, Bacillus subtilis, Heamophilus influenzae, Helicobacter pylori, Mycobacterium leprae, Mycobacterium tuberculosis, Pseudomonas stutzerii, Rhodococcus erythropolis*, and Synechocystis PCC6803 as well as the Ybec sequence of *E. coli* (FIGS. 8A–8F).

EXAMPLE 7

*E. coli* mttB and mttC Form an Operon with mttA

A. The mttABC Operon

Examination of the DNA sequence adjacent to mttA suggested that the upstream gene, yigR, encodes an aminoglycosyl transferase (BLAST search of the non-redundant data base). A potential transcription terminator at position 5590–5610 of contig AE00459 [Blattner et al. (1997) Science 277:1453–1462] separates yigR from mttA.

To test whether the adjacent genes mttB and mttC form an operon with mttA, mRNA was isolated from aerobically grown HB101 and RT-PCR was used with a primer within mttC to make a cDNA product. This cDNA was then amplified by PCR with primers within mttA and mttB giving the expected product of 270 bp., and mttA and mttC giving a product of 1091 bp. confirming a single polycistronic mRNA for the mttA, mttB, and mttC genes. To ensure that the PCR products were not the result of contaminating chromosomal DNA, the mRNA preparation was extensively digested with DNase prior to PCR and a control omitting the RT-PCR step did not give any products after PCR amplification.

The nucleotide sequence (SEQ ID NO:45) of the mttABC operon is shown in FIGS. 11A–11E. FIGS. 7A–7J also show the nucleotide sequence of the three open reading frames, ORF RF[3], ORF RF[2] and ORF RF[1], and the encoded amino acid sequences of MttA (SEQ ID NO:1), MttB (SEQ ID NO:7) and MttC (SEQ ID NO:8), respectively.

B. Proteins Homologous to the MttB and MttC Proteins

A database search of sequences which are related to mttB and mttC identified a large family of related proteins which are organized contiguously in several organisms. In all cases the function of these proteins was previously unknown.

Figure 9A:
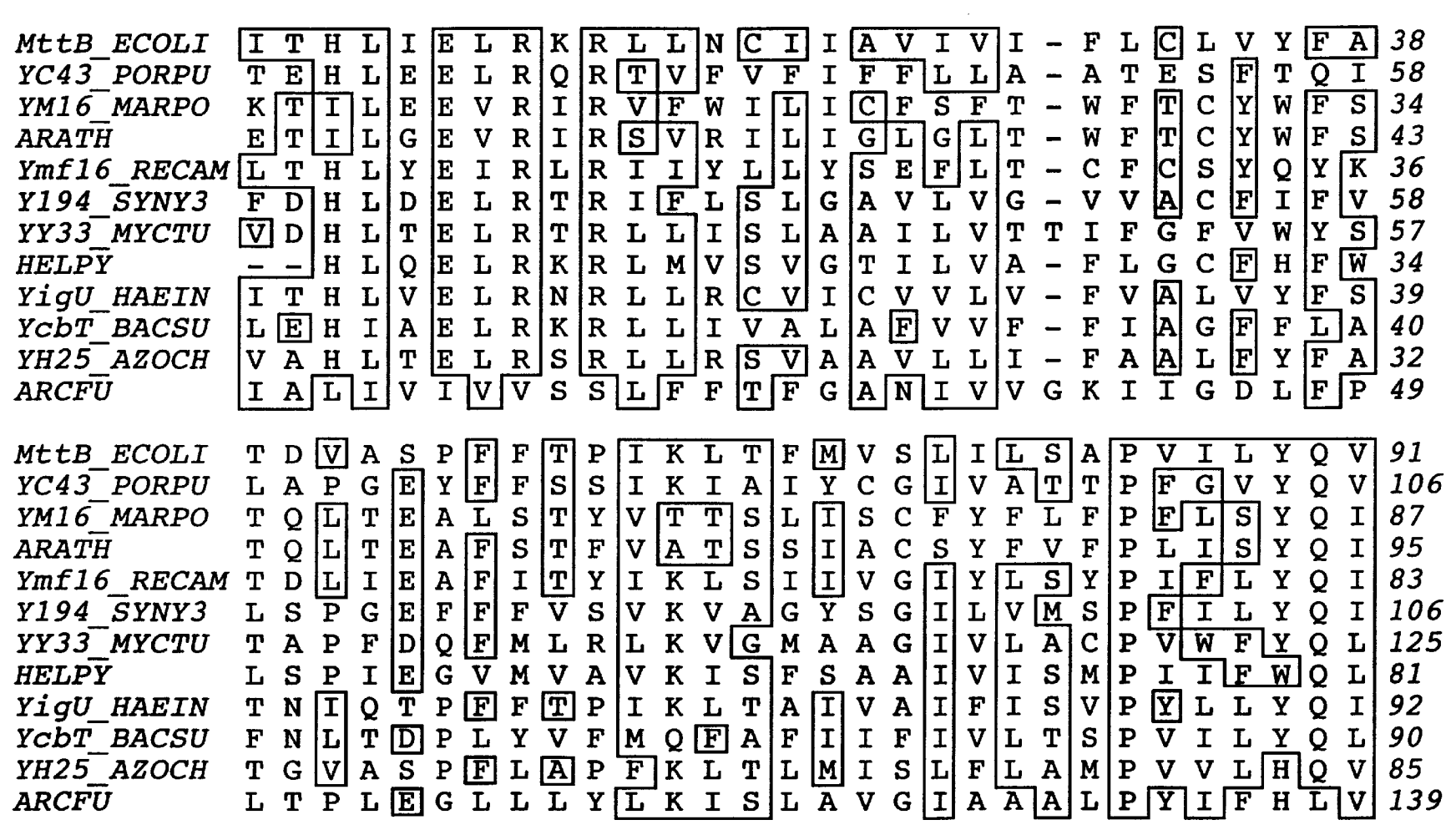
Figure 9B:
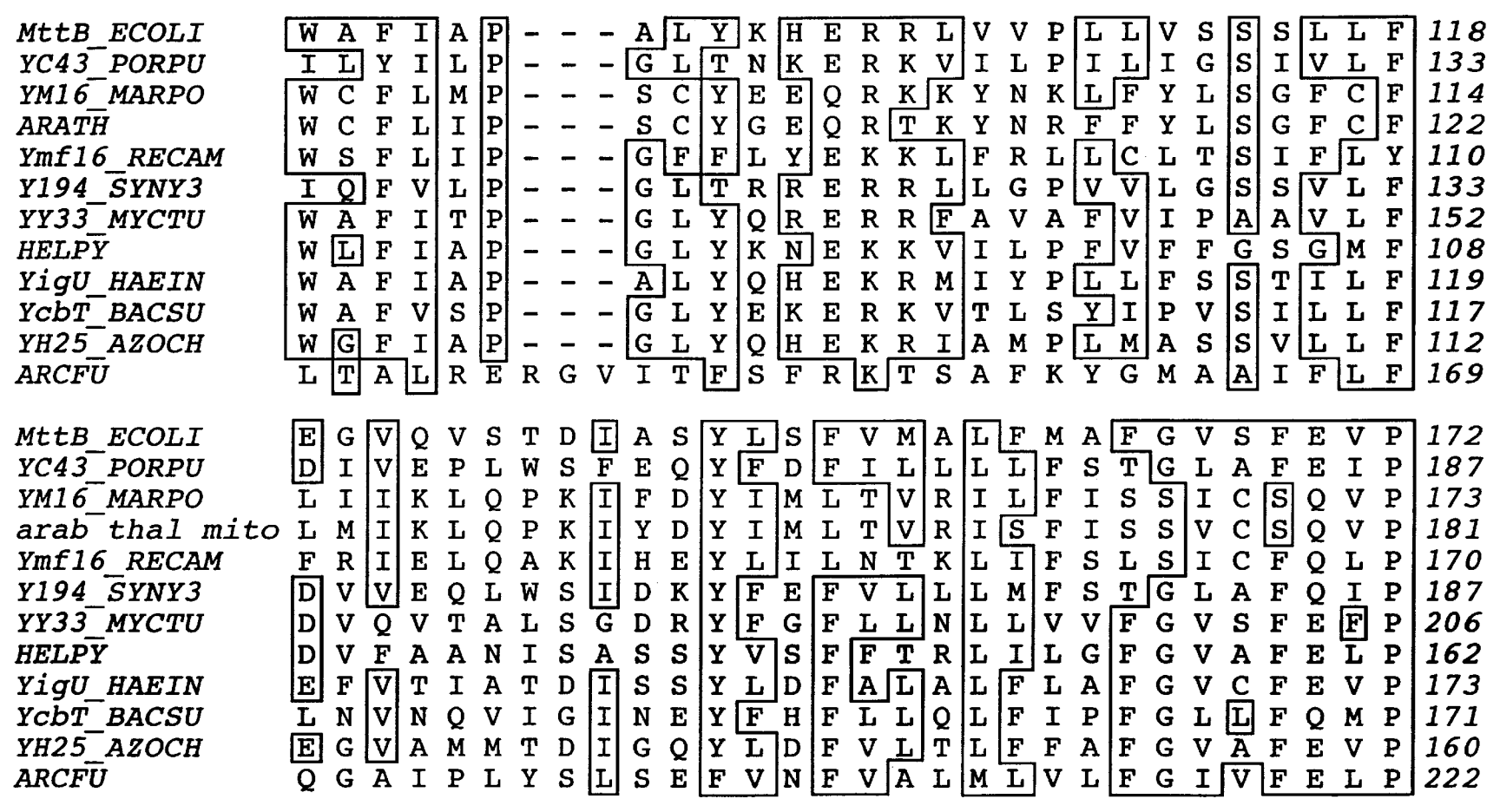

The nucleotide sequence of mttB (SEQ ID NO:)5 is shown in FIGS. 7A–7J. mttB encodes an integral membrane protein of 258 amino acids with six predicted transmembrane segments. A large number of related sequences was identified in a BLAST search extending from the archaebacteria (*Archeoglobus fulgidus*), through the eubacteria (*Azotobacter chroococcum, Bacillus subtilis, Heamophilus influenzae, Helicobacter pylori, Mycobacterium laprae, Mycobacterium tuberculosis*), cyanobacteria (Synechocystis PCC6803) to mitochondria of algae (*Reclimonas americana, Chondrus crispus*) and plants (*Arabidopsis thalania, Marchantia polymorpha*) as well as chloroplasts of *Porphyra purpurea* and *Odentella sinensis* (FIGS. 9A and 9B).

Figure 10A:
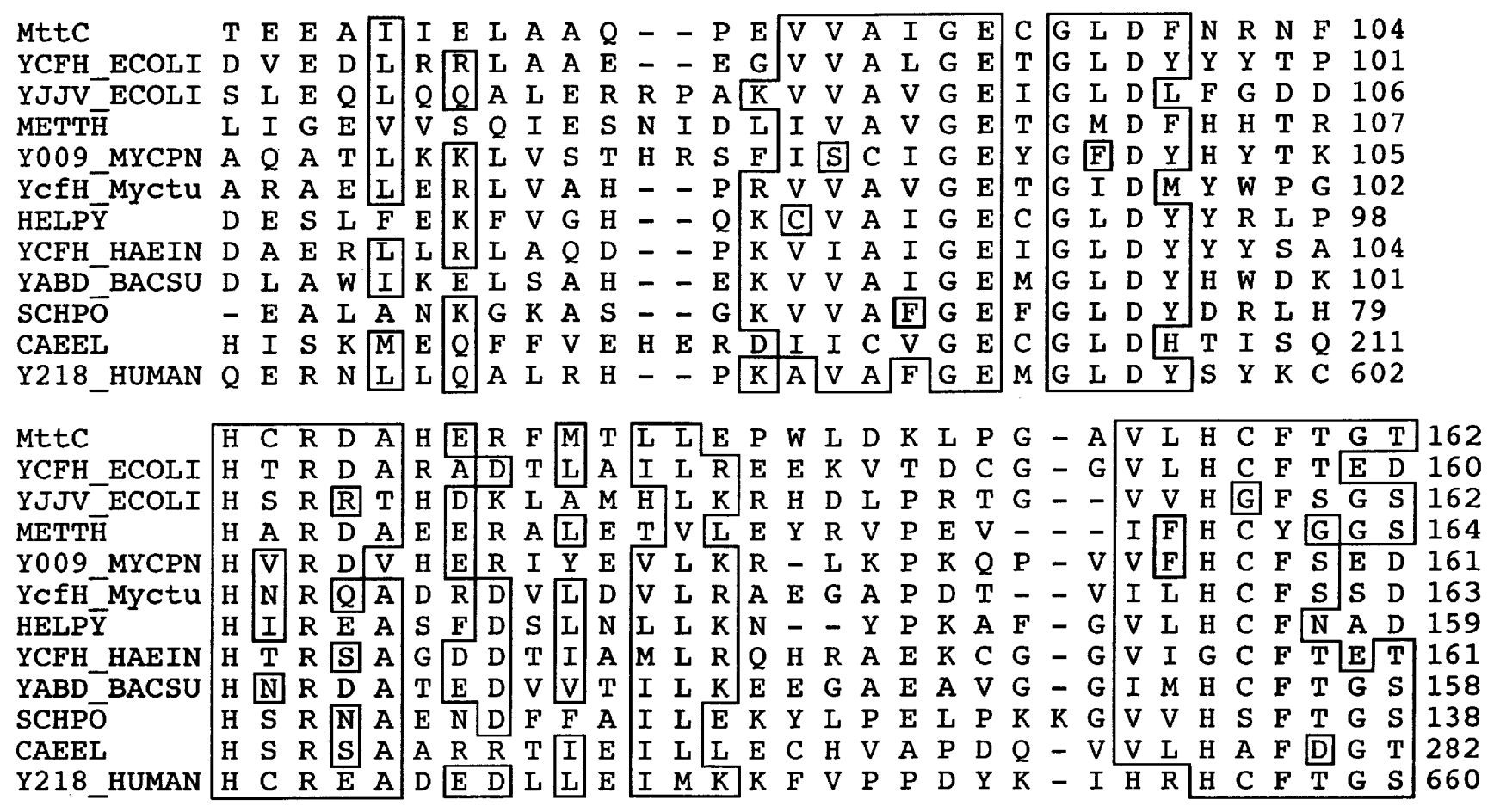

The nucleotide sequence of the neighboring gene mttC (SEQ ID NO:6) is shown in FIGS. 7A–7J. mttC encodes a polypeptide of 264 amino acids which is predicted to have at least one potential transmembrane segment (residues 24–41). The most likely orientation of this protein results in a large cytoplasmic domain extending from residue 41 to 264. Without limiting the invention to any particular mechanism, there is the possibility of a second transmembrane domain at residues 165–182. This possibility may be confirmed by a blaM gene fusion analysis. Like MttA and MttB, the MttC protein also is a member of a very large family of homologous proteins which includes two homologous sequences in *E. coli* (Ycfh and Yjjv) as well as homologous sequences in archaebacteria (*Methanobacterium thermoautotrophicum*), Mycoplasma (*Mycoplasma pneumoniae* and *Mycoplasma gentitaluium*), eubacteria (*Bacillus subtillis, Heamophilus influenzae, Helicobacter pylori, Mycobacterium tuberculosis*), cyanobacteria (Synechocytis PCC6803), yeast (*Schizosaccharomyces pombe* and *Saccharomyces cerevisae*), *C. elegans* and humans (FIGS. 10A and 10B). The human protein is notable in having a 440 amino acid extension at the amino terminus which is not found in the other proteins. This extension is not related to MttA or MttB.

EXAMPLE 8

Construction of Host Cells Containing a Deletion of at Least a Portion of the genes mttA, mttB and mttC The function of MttA, MttB and MttC proteins in a host cell is demonstrated by in vivo homologous recombination of chromosomal mttA, mttB and mttC as previously described [Sambasivarao et al (1991) J. Bacteriol. 5935–5943; Jasin et al (1984) J. Bacteriol. 159:783–786]. Briefly, the mttABC operon is cloned into vectors, and the gene whose function is to be determined (i.e., mttA, mttB or mttC) is mutated, e.g., by insertion of a nucleotide sequence within the coding region of the gene. The plasmids are then homologously recombined with chromosomal mttA, mttB or mttC sequences in order to replace the chromosomal mttA, mttB or mttC genes with the mutated genes of the vectors. The effect of the mutations on the localization of proteins containing twin-arginine amino acid signal sequences is compared between the wild-type host cells and the cells containing the mutated mttA, mttB or mttC genes. These steps are further described as follows.

A. Construction of Plasmids Carrying Deletions or Insertions in mttA, mttB and mttC Genes The mttABC operon (FIGS. 11A–11E) is cloned into pTZ18R and pB322 vectors. In pB322, the HindIII site in mttB is unique. The pB322 containing mttB is then modified by insertion of a kanamycin gene cartridge at this unique site, while the unique NruI fragment contained in mttC is replaced by a kanamycin cartridge.

B. Homologous Recombination and P1 Transduction

The modified plasmids are homologously recombined with chromosomal mttA, mttB and mttC in *E. coli* cells which contain either a recBC mutation or a recD mutation. The resulting recombinant is transferred by PI transduction to suitable genetic backgrounds for investigation of the localization of protein expression. The localization (e.g., cytoplasm, periplasm, cell membranes, extracellular medium) of expression of twin arginine containing proteins is compared using methods disclosed herein (e.g., functional enzyme activity and Western blotting) between homologously recombined cells and control cells which had not been homologously recombined. Localization of expressed twin arginine containing proteins extracellularly, in the periplasm, or in the cytoplasm of homologously recombined cells as compared to localization of expression in cell membranes of control cells demonstrates that the wild-type MttA, MttB or MttC protein whose function had been modified by homologous recombination functions in targeting expression of the twin arginine containing protein to the cell membrane. Similarly, accumulation of expressed twin arginine containing proteins in extracellular medium, in the cytoplasm, or in cell membranes of homologously recombined cells as compared to periplasmic localization of the expressed twin arginine containing protein in control cells which had not been homologously recombined indicates that the protein (i.e., MttA, MttB or MttC) whose function had been modified by homologous recombination functions in translocation of the twin arginine containing protein to the periplasm.

EXAMPLE 9

Wild-type and Mutant Twin-arginine Amino Acid Signal Sequences of PreDmsA are Cleaved to Release Mature DmsA In this Example, the following numbering system for DmsA has been used: the mature protein starts at Val 46; the leader extends from Met1 to Ala 45 and the double Arg signal is at residues 15–21. In order to determine whether preproteins which contain twin-arginine amino acid signal sequences are cleaved to release a mature polypeptide as suggested by Berks [Berks (1996)], the two alanine amino acids at the −1 and −3 positions of the twin-arginine amino acid signal sequences of wild-type DmsA preprotein were replaced with asparagine, and cleavage of both the wild-type and the mutated twin-arginine amino acid signal sequences was investigated.

A. Cell Culture Conditions

Cells were grown anaerobically in Luria Broth [Sambrook (1989)] and these cultures were used for a 1% inoculum into glycerol minimal medium with 0.167% peptone and vitamin B1, proline, leucine at final concentrations of 0.005%.

All manipulations of plasmids and strains were carried out as described by Sambrook et al. (1989)].

The upstream untranslated region of DmsA was examined using software from the Center for Biological Analysis (http://www.cbs.dtu.dk/) to identify potential leader peptidase I cleavage sites. This analysis indicated that mutation of both Ala43 and Ala45 was needed to inhibit cleavage. An additional secondary cleavage site with low probability was identified between Thr36 and Leu37. The two Ala mutated in this study were Ala43 and Ala45 which are underlined in the following DmsA leader sequence (SEQ ID NO:43) that contains the twin-arginine amino acid signal sequence:

```
1               15              30              43 45
MKTKIPDAVLAAEVSRRGLVKTTIAFFLAMASSALTLPFSRIAHAVDSAI
```

Mutants were generated by site-directed mutagenesis of single stranded DNA of plasmid pDMS223 [Rothery and Weiner (1991) Biochemistry 30:8296–8305] using the Sculptor kit (Amersham) and mutagenic primers to generate the mutants A43N and A43N,A45N. The mutagenic primer (SEQ ID NO:44) 5'-TTAGTCGGATTAAT(CACAATGTCGATAGCG-3' was used. Mutant DNA was subcloned into pDMS160 [Rothery and Weiner (1991)] using BglII and EcoRI restriction sites, and resequenced to confirm the mutation.

B. Expression Studies

Samples were removed from the cultures after 30–48 hours of anaerobic growth, the cells pelleted by centrifugation at 9500 g for 10 min., resuspended and everted envelopes prepared by French Press lysis. The cytoplasm and membrane fractions were separated by differential centrifugation. Membranes were washed twice with 50 mM MOPS pH7.0 prior to use. Membrane proteins were solubilized with 1% SDS and polyacrylamide gel electrophoresis was performed using the Bio-Rad minigel system with a discontinuous SDS buffer system [Laemmli (1970) Nature 227:680–685]. Western blotting was performed using affinity purified DmsA antibody with the ECL Western blotting detection reagents from Amersham Life Sciences.

The results (data not shown) demonstrated cleavage of both the preDmsA proteins which contained alanine and which contained asparagine in the twin-arginine amino acid signal sequence to release mature DmsA. These results suggest that twin-arginine amino acid signal sequences are cleaved by signal peptidase I which also cleaves Sec signal sequences. Alternatively, a signal peptidase which is different from signal peptidase I and signal peptidase II, and which has different specificity may be operative. This possibility is investigated by N-terminal amino acid sequencing.

C. N-terminal Amino Acid Sequencing

N-terminal amino acid sequencing is carried out as previously described [Bilous et al (1988) Molec. Microbiol. 2:785–795] in order to determine the cleavage site in preDmsA and other preproteins which contain twin-arginine amino acid signal sequences, e.g., preTorA, and preNapA. A signal peptidase I temperature sensitive mutant is used to determine if preDmsA, preTorA and preNapA are cleaved at the restrictive temperature. Amino terminal sequences are determined by automated Edman degradation on an Applied Biosystems Model 470A gas phase sequenator. Subunits are separated by SDS PAGE and electroblotted onto polyvinylidene fluoride membranes and electroeluted as described by Cole et al. [J. Bacteriol. 170:2448–2456 (1988)].

The above-presented data shows that mttA1, mttA2, mttB and mttC encode proteins MttA1, MttA2, MttB and MttC which are essential in a Sec-independent pathway, and which function in targeting twin arginine containing proteins to cell membranes and in translocating twin arginine containing proteins to the periplasm and extracellular medium. The above-disclosed data further demonstrates that disruption of the function of any one or more of MttA1, MttA2, MttB and MttC results in translocation of twin arginine containing proteins to the periplasm, to extracellular medium, or to cellular compartments other than those compartments in which the twin arginine containing proteins are translocated in cells containing wild-type MttA1, MttA2, MttB and MttC. These results demonstrate that mttA1, MttA2, MttB and mttC are useful in translocating twin arginine containing proteins to the periplasm and extracellular medium. Such translocation is particularly useful in generating soluble proteins in a functional form, thus facilitating purification of such proteins and increasing their recovery.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art and related fields are intended to be within the scope of the following claims.

What is claimed is:

1. A method for expressing a nucleotide sequence of interest in a host cell to produce a soluble polypeptide sequence, said nucleotide sequence of interest when expressed in the absence of an operably linked nucleic acid sequence encoding a twin-arginine signal amino acid sequence produces an insoluble polypeptide, comprising:
  a) providing:
    i) said nucleotide sequence of interest encoding said insoluble polypeptide;
    ii) said nucleic acid sequence encoding said twin-arginine signal amino acid sequence; and
    iii) said host cell, wherein said host cell comprises at least a portion of an amino acid sequence selected from the group consisting of SEQ ID NO:47, SEQ ID NO:49, SEQ ID NO:7 and SEQ ID NO:8, wherein said at least a portion of said amino acid sequence has a biological activity selected from the group consisting of targeting of a fully-folded protein which contains a twin-arginine signal amino acid sequence to a cell membrane, translocating of a fully-folded protein which contains twin-arginine signal amino acid sequence to a periplasm, and translocating of a fully-folded protein which contains a twin-arginine signal amino acid sequence to an extracellular space.
  b) operably linking said nucleotide sequence of interest to said nucleic acid sequence encoding said twin-arginine signal amino acid sequence to produce a linked polynucleotide sequence; and
  c) introducing said linked polynucleotide sequence into said host cell under conditions such that said fused polynucleotide sequence is expressed and said soluble polypeptide is produced.

2. The method of claim 1, wherein said insoluble polypeptide is included in an inclusion body.

3. The method of claim 1, wherein said insoluble polypeptide binds a cofactor.

4. The method of claim 3, wherein said cofactor is selected from the group consisting of iron-sulfur clusters, molybdopterin, polynuclear copper, tryptophan tryptophylquinone, and flavin adenine dinucleotide.

5. The method of claim 1, wherein said soluble polypeptide is in the periplasm of said host cell.

6. The method of claim 1, wherein said host cell is cultured in medium, and wherein said soluble polypeptide is contained in said medium.

7. The method of claim 1, wherein said cell is *Escherichia coli*.

8. The method of claim 1, wherein said twin-arginine signal amino acid sequence is selected from the group consisting of SEQ ID NO:41 and SEQ ID NO:42.

9. A method for expressing a nucleotide sequence of interest encoding an amino acid sequence of interest in a host cell, comprising:
 a) providing:
  i) said host cell;
  ii) said nucleotide sequence of interest;
  iii) a first nucleic acid sequence encoding twin-arginine signal amino acid sequence; and
  iv) a second nucleic acid sequence encoding at least a portion of an amino acid sequence selected from the group consisting of SEQ ID NO:47, SEQ ID NO:49, SEQ ID NO:7 and SEQ ID NO:8, wherein said at least a portion of the amino acid sequence encoded by said second nucleic acid has a biological activity selected from the group consisting of targeting of a fully-folded protein which contains a twin-arginine signal amino acid sequence to a cell membrane, translocating of a fully-folded protein which contains twin-arginine signal amino acid sequence to a periplasm, and translocating of a fully-folded protein which contains a twin-arginine signal amino acid sequence to an extracellular space.
 b) operably fusing said nucleotide sequence of interest to said first nucleic acid sequence encoding a twin-arginine signal amino acid sequence to produce a fused polynucleotide sequence; and
 c) introducing said fused polynucleotide sequence and said second nucleic acid sequence into said host cell under conditions such that said at least portion of said amino acid sequence selected from the group consisting of SEQ ID NO:47, SEQ ID NO:49, SEQ ID NO:7 and SEQ ID NO:8 is expressed, and said fused polynucleotide sequence is expressed to produce a fused polypeptide sequence comprising said twin-arginine signal amino acid sequence and said amino acid sequence of interest.

10. The method of claim 9, wherein said expressed amino acid sequence of interest is contained in periplasm of said host cell.

11. The method of claim 10, wherein said expressed amino acid sequence of interest is soluble.

12. The method of claim 9, wherein said host cell is cultured in medium, and wherein said expressed amino acid sequence of interest is contained in said medium.

13. The method of claim 12, wherein said expressed amino acid sequence of interest is soluble.

14. The method of claim 9, wherein said second nucleic acid sequence encodes an amino acid sequences selected from the group consisting of SEQ ID NO:47, SEQ ID NO:49, SEQ ID NO:7, and SEQ ID NO:8.

* * * * *